(12) United States Patent
Wagner et al.

(10) Patent No.: US 8,227,573 B2
(45) Date of Patent: Jul. 24, 2012

(54) UTILITY OF PHYLLOPLANINS AS ANTIBIOTICS, SELECTIVE FUNGICIDES AND FOR ENHANCING MICROBIAL RESISTANCE IN PLANTS

(75) Inventors: George Wagner, Wilmore, KY (US); Ryan Shepherd, Berkeley, CA (US)

(73) Assignee: University of Kentucky Research Foundation, Lexington, KY (US)

( * ) Notice: Subject to any disclaimer, the term of this patent is extended or adjusted under 35 U.S.C. 154(b) by 1057 days.

(21) Appl. No.: 12/149,881

(22) Filed: May 9, 2008

(65) Prior Publication Data

US 2009/0215667 A1     Aug. 27, 2009

Related U.S. Application Data

(63) Continuation-in-part of application No. 11/304,528, filed on Dec. 15, 2005, now Pat. No. 7,528,232.

(60) Provisional application No. 60/682,814, filed on May 20, 2005.

(51) Int. Cl.
   C07K 14/00         (2006.01)
   A61K 38/00         (2006.01)

(52) U.S. Cl. .............................. 530/350; 530/370; 514/2

(58) Field of Classification Search ........................ None
   See application file for complete search history.

(56) References Cited

U.S. PATENT DOCUMENTS

2009/0281038 A1* 11/2009 Wagner et al. .................. 514/12

OTHER PUBLICATIONS

Shepherd et al., "Phylloplanins of Tobacco are defensive proteins deployed on aerial surfaces by short glandular trichomes", (Plant Cell, 2005, vol. 17, pp. 1851-1861).*
Ashkenazi, A., et al. "Protection against endotoxic shock by a tumor necrosis factor receptor immunoadhesin" PNAS USA, (1991). 88:10535.
Bird, C. R., et al. "The tomato polygalacturonase gene and ripening-specific expression in transgenic plants" Plant Molecular Biology, (1988)11:651-662.
Bird, R. E., et al. "Single-chain antigen-binding proteins" Science, (1988), 242:423.
Byrn, R. A., et al. "Biological properties of a CD4 immunoadhesion" Nature, (1990) 344:677.
Capecchi, M. R. "The new mouse genetics: Altering the genome by gene targeting" TIG, (1989).5:70.
Ausubel, F. M., et al., eds., John Wiley & Sons, Inc., sections 2.10 and 6.3-6.4.Short Protocols in Molecular Biology, Third Edition A Compendium of Methods from Current Protocols in Molecular Biology, (1995).
Devereux, J., et al."A comprehensive set of sequence analysis for the VAX" Nucl. Acids Res. (1984).12:387.
Diekman, J. and Robert L. Fischer "Interaction of a DNA binding factor with the 5'-flanking region of an ethylene-responsive fruit ripening gene from tomato" EMBO, (1988). 7:3315-3320.
Felgner, P.L. et al. "Lipofection: A highly efficient, lipid-mediated DNA-transfection procedure" Proc. Natl. Acad. Sci. USA, (1987) 84:7413-7417.
Gribskov, M. and Richard R. Burgess "Sigma factors from E. coli, B. subtilis, phage SP01, and phage T4 are homologous proteins" Nucl. Acids Res. (1986) 14:6745.
Saragovi, H. U., et al. "Loops and secondary structure mimetics: development and applications in basic science and rational drug design" Bio/Technology, (1992). 10:773-778.
Hollenbaugh, D. and Alejandro Aruffo, "Construction of Immunoglobulin Fusion Proteins", Current Protocols in Immunology, (1992). Suppl. 4, pp. 10.19.1-10.19.11.
Hopp, T. P., et al. "A short polypeptide marker sequence useful for recombinant protein identification and purification" Bio/Technology, (1988). 6:1204-1210.
Huse, W. D., et al. "Generation of a large combinatorial library of the immunoglobulin repertoire in phage lambda" Science, (1989). 246:1275-1281.
Huston, J. S., et al. "Protein engineering of antibody binding sites: Recovery of specific activity in an anti-digoxin single-chain Fv analogue produced in Escherichia coil" PNAS, (1988). 85:5879-5883.
Janeway, Jr., C.A. et al. Immunobiology, (1996). 3:9, Garland Publishing Inc., 2nd ed.
Kaufman, R. J., "Use of recombinant DNA technology for engineering mammalian cells to produce proteins" Large Scale Mammalian Cell Culture, (1990) pp. 15-69.
Kaufman, R. J. et al. "Improved vectors for stable expression of foreign genes in mammalian cells by use of the untranslated leader sequence from EMC virus" Nucleic Acids Res, (1991). 19:4485-4490.
Kaufman, R. J. "Vectors used for expression in mammalian cells" Meth. In Enzymology, (1990). 185:487-511.
Li, W., et al. "Saturated Blast: an automated multiple intermediate sequence search used to detect distant homology" Bioinformatics, (2000) 16(12):1105-1110.
Luckow, V. A. and Max D. Summers "Trends in the development of baculovirus expression vectors" Bio/Technology, (1988). 6:47-55.
Newton, D. L., et al. "Angiogenin single-chain immunofusions: Influence of peptide linkers and spacers between fusion protein domains" Biochemistry, (1996). 35:545-553.
Pear, J. R., et al. "Isolation and characterization of a fruit-specific cDNA and the corresponding genomic clone from tomato" Plant Molecular Biology, (1989). 13:639-651. Kaufman, R. J., "Selection and coamplification of heterologous genes in mammalian cells" Methods in Enzymology, (1990) 185, 537-566.
McDowell, R. S. and Thomas R. Gadek, "Structural studies of potent constrained RGD peptides" J. Amer. Chem. Soc., (1992). 114(24):9245-9253.
Wu, U. et al., eds., Recombinant DNA Methodology, Academic Press, Inc., San Diego (1989), pp. 189-196.

(Continued)

Primary Examiner — Anand Desai
(74) Attorney, Agent, or Firm — Crowell & Moring LLP

(57) ABSTRACT

The present invention relates to plant proteins produced by a plant's epidermal layer that contribute to the innate pest/disease resistance of the plant ("phylloplanins"), compositions comprising the phylloplanins and methods of using them. In particular the methods relate to inhibiting or preventing microbial, e.g., fungal or bacterial, growth on a subject, organism or surface by administering a phylloplanin. The invention also relates to transformed host cells that produce phylloplanins, and to transgenic plants producing phylloplanins conferring increased resistance to microbial infections/growth.

21 Claims, 14 Drawing Sheets

OTHER PUBLICATIONS

Saiki, R. K., et al. "Primer-directed enzymatic amplification of DNA with a thermostable DNA polymerase" *Science*, (1988). 239:487-491.

Sambrook, et al. *Molecular Cloning: A Laboratory Manual, Cold Spring Harbor Laboratory Press*, Cold Spring Harbor, N.Y., (1989) chapters 9 and 11.

Schimke, R. T., et al. "Amplification of genes in somatic mammalian cells" *Methods in Enzymology*, (1987) 151:85-104.

Urlaub, G., et al. "Isoloation of Chinese hamster cell mutants deficient in dihydrofolate reductase activity" *Proc. Natl. Acad. Sci. USA*, (1980) 77:4216-4220.

Ward, E. S., et al. "Binding activities of a repertoire of single immunoglobulin variable domains secreted from *Escherichia coli*" *Nature*, (1989). 341:544-546.

Whitlow, M., et al. "An improved linker for single-chain Fv with reduced aggregation and enhanced proteolytic stability" *Protein Engineering*, (1993) 6 (8):989-995.

Wootton, J. C. and Scott Federhen "Analysis of compositionally biased regions in sequence databases" *Methods in Enzymol*, (1996) 266:554-571.

\* cited by examiner

```
                                                            M   A   S
AACACAATTTCTTACAGCAATAACTATCACATATAACAATAACTGCC ATG GCT TCA       56

A   K   I   F   L   I   F   L   L   A   A   L   I   A   T
GCA AAA ATT TTC TTG ATT TTC CTT TTG GCT GCA TTA ATC GCA ACC      101
                                        aa-N1
 P   A   A   F   A   I   L   V   P   T   L   V   S   T   H
CCC GCT GCA TTT GCC ATA CTT GTT CCA ACA CTT GTT TCA ACA CAT      146

I   S   G   L   V   F   C   S   V   N   G   N   L   D   V
ATA AGT GGG CTT GTA TTT TGC AGC GTT AAC GGC AAT TTA GAT GTC      191
                                                    aa-T1
 I   N   G   L   S   P   Q   V   F   P   N   A   S   V   Q
ATC AAC GGA CTC AGT CCC CAA GTT TTT CCT AAT GCA TCA GTG CAA      236
                        aa-T2
 L   R   C   G   A   T   N   V   I   S   S   T   I   T   N
TTG CGG TGT GGA GCA ACA AAT GTG ATA TCA AGT ACA ATA ACA AAT      281

G   S   G   A   F   S   L   A   V   N   T   F   P   L   L
GGA TCG GGA GCA TTT TCC TTG GCG GTG AAT ACT TTC CCA CTG CTA      326
                                    aa-T3
 N   C   N   L   V   V   A   T   P   L   S   T   C   N   A
AAC TGC AAT TTA GTG GTT GCA ACT CCA CTA TCA ACA TGT AAC GCG      371

T   L   Q   S   V   G   R   L   A   S   S   L   R   L   V
ACC TTA CAA TCG GTT GGG CGT TTG GCG TCA TCC TTG AGA CTT GTA      416
                                                aa-P1
 N   I   T   L   G   S   G   T   G   L   I   R   V   G   L
AAT ATC ACT CTT GGC AGT GGC ACC GGT CTT ATT AGA GTC GGT TTA      461
                                aa-T4
 A   P   T   G   F   I   L   N   L   N   I   N   * (SEQ ID NO:18)
GCT CCT ACT GGT TTT ATA CTT AAT CTT AAC ATC AAT TAA TATTGAAC     508
GAGCTAGCCTGCTGGTTCTTAATTAGTACTACTACTATGCATCAGCTAGTTAACTTTCTT     568
GGCCAGCTGCTTACTGCAAGAATAAGGACTGTTGTTTCCACTAGTGAATAAAGTGCAAAT     628
CATATTTGCAAGTCTAAAAAAAAAAAAAAAAAAAAAAAA     (SEQ ID NO:17)      666
```

Figure 3.

```
1   ------------------------IDVPTLV--------STH-ISGLVTCSVNGNLDVINGLSPQVFPNASVQI Nt Phylloplanin
1   QILPPPILPPTIIRP---------P----PILPPIVLPPPIVLNPVLN-VTGIVSCSVNATVNT---TTASPFPNBQVQI Sr BG525459
1   ---QLG-GLGGGLGG---------LG---MLGGITN--------IFN-IQCLLMCSVTGTVSTNNATAVSPFPNAGIVF Br CV545024
1   -------VLIAAQADE--------A----QGIPPITA--------AVN-ISCIVTCSVNGSAN------AGPPANBLVEL Ha CD847345
1   ---QLGLGGSGGLGGLIGGLVGGLGGLVGGLVGGILN--------LVN-INGVVTCSLNGAPS---STSTPAFABANBVBL At AAP75801
1   ----------QSGLGG------------------IN--------VPI-INGVLRCTINGAPLN--ETPABABANAVVQI At AAN28743
1   -------APPAQPPR---------------IQADVV--------VM--GYVPCNNGTISMK--SGSAFGPBIRVVQI Os XP_479490
1   -------------------------KIGRIV--------VT----GVVPCNTGSLID---IATSBAFFNBDVEL Os XP_479489
1   --------QIGG---------------LIGGILG--------PIS-IDGVLBCSLNGKIDVLNGATTIFPNBSVQI St CV502724
1   --------QIGG---------------LIGGILA--------PTS-IEGVLRCSLNGKIDVLNGATTIFPDBSVQI Le BP903020
1   ----------------------------------------GTPNGNIG-VNGTSTBVFPNABAMVQI Am 789767
1   ------APVAEAQIG-------------LIGGILG--------LIR-ICGTLFCTADGNIG-ANGTATBVFPBPLVQI Pt BU829351
1   --------QIG---------------ISGILG--------SVSNIQCTSKDNMG-VKGASVGVFPNBQVQI Gm BM527339
1   -------------------------KIGRIV--------VS----GVAPCNTGSLID---IATSBAFFNAEVEL Hv BM371086

42  RGGATN-VIS----STILNGSCAFSLAVNTFP-----LIN--CNLVVATPLSTCNATLQSVGRIAGSIRLWNITLGSGTG Nt Phylloplanin
64  RGGG-L-WVG----AMINQSBAGNIVVNEFLSTVANILS--GRVVVITPLADCRVTLPSTGTLQAPLGIVG----N--I Sr BG525459
56  QGIGQN--VS----STINANGVFSIPTIGLPFSPSTILSSGCRLVVITPLACNVSLFAAGLUMAPISLWGTAAGD--G Br CV545024
47  SGGG-N-BIA----SAVMNAQCVDNITVNBLRVTLNNMLSS-GRIDAITPLSNCNAILFTAGTLCSALGVACTFIRG--I Ha CD847345
66  CGGRQNRWVS----TAIINAAGLESLPTDSIQMLLSTILS-DCRIVVTIPLSPSSCDATLPSVGNLVSRIAMIGNSLIG--L At AAP75801
41  QGBNLNRWVA----ETIINIACLETFSTNGIQISLPTLLN-DCRIVYFIERSSCDATLESTGQLISQLNLVGSIVSG--L At AAN28743
43  QGAC-DAMAAVAAGSATIDGKGWRMAMNTTA-ALESVAG-GGSLVVITPIADCDAMPATGTLQSGIR----LLVS---- Os XP_479490
35  RGAG-KLVAG----AITINSNGSFAMEADLTS-GDAMIIG--GCKLVVDTPLIKCDANLFAAGSIVGYLQGPLTRLLG--- Os XP_479489
46  RGCAGH-WVS----STINGSCAFSLVLNEVQNILSSILS-NCNIVVITPLSTCNASLPSVGVIIQAPIGIVGRTTGG--- St CV502724
46  RGCAGH-WVS----STINGSCAFSLVTSFVQSLLSSILS-DCNIVVITPLSTCNALPSVGVLQAPLQIVEKTAGSGL- Le BP903020
25  CGGG-T-WVS----TTINGLCQFSMLLDFLNFVLSTIVS-GCRDVITPLDCNASLPSVGVIBTLQFVGSTVLG--L Am 789767
50  QGGG-H-WVS----TSINGSCMFSILLDELSYILSSILS-DCNLVQCTPLISCNSSBAVGGILSPLRFIGNTALGA-V Pt BU829351
45  VGGG-K-ELS----NAKINDDGTFSMMMDILLLDIASILS-GCNLAVATPLSNCNAKLPSTGCLISTINFAGITSVG--T Gm BM527339
35  RGAG-QVVAG-----AITINTNGSITMEADLTS-ALAAFIG-RCSLVADTPLIKCDACLEPAGRIVSYLQGPLTRLLG--- Hv BM371086

110 IRVGLAPTGSILNLNIN    (SEQ ID NO.: 18)    Nt Phylloplanin
130 INTLFAIPGQELYLQV     (SEQ ID NO.: 36)    Sr BG525459
128 IRNFSIVESAPGLVG      (SEQ ID NO.: 37)    Br CV545024
118 INNVNIVGIRER-LVV     (SEQ ID NO.: 38)    Ha CD847345
139 INIISIIPAGGLLN       (SEQ ID NO.: 39)    At AAP75801
114 INIVAILPTGSIPTI      (SEQ ID NO.: 40)    At AAN28743
113 -MVF--FBRGESYVV      (SEQ ID NO.: 41)    Os XP_479490
104 -GIFRIFPAGSFHAH      (SEQ ID NO.: 42)    Os XP_479489
117 --LVNIVTGVEQLIPLLN   (SEQ ID NO.: 43)    St CV502724
119 INIVKLVTGAPQLIN      (SEQ ID NO.: 44)    Le BP903020
96  INVGNIIPSGENFSANMNLN (SEQ ID NO.: 45)    Am 789767
122 ISVANIIPAGERFVPSN    (SEQ ID NO.: 46)    Pt BU829351
116 QTMANIIESGHFLPSI     (SEQ ID NO.: 47)    Gm BM527339
104 -GIFRIFPAGSFHSR      (SEQ ID NO.: 48)    Hv BM371086
```

Figure 8A

```
-1157 cccattccac tatgaacttc ccggaattca attctgacta tgcgtacaag tcataatgaa
-1097 gctgcacata gccttcatat cgctaaacga cgtgctaggt ctcaaaacga cctgtcgggg
-1037 tcgttacatt agaggtgatt aacttcgtgt atacttgtgc aagtgttcta taacaatttc
-977  aggccaacct agtaagagta gaaatagtga atggcacata acaaacgatc accacgaaat
-917  gtacatgata taactcacac aaggtaggca cgctactaga caattaccaa taacaacaat
-857  gcctaggaca tcacaagata tgaaaaatca atccttacta tcacggttga gttgtaacgt
-797  gtaagaatat ttcacacttt ttagggcact aagatcactc caccaacatt tcaagagaat
-737  cactggcact gccaaaaagc cctctacact gtagtgaatt tttgttagtt atctaaagtt
-677  aattattcac ttagtattct ttacattagg ttccccctt ctaggtcctg cacgtaacta
-617  gattgaatgg attggtccac tctattatta cagagtaatt attaaatttt tatttgacta
-557  ggcaacacta attgcactat caacaaagta ttagttctag ccttctgggt acttcatacc
-497  tatgcaaatg ataatttat ttaaaacaat agatgtacat ggatataaat acctatgaaa
-437  attaaataaa atataactaa gaaaaaaaat ttaaagttca ctcctaagat atcgggttat
-377  tacatgacca aacacaattt gtttatcaaa tactttcaaa agaatttgtc aaacgtaaat
-317  tatttttctc caaagtgact tatgaattac tatgttgata aaatactttt caaagtaact
-257  aatgtttaga agtcaaggat gggcttcttt tgattattga agtttgtagc aattgtatgt
-197  agttatagtc agggtgacca ccagcatctc atatagcaat acacaagtgg gttagcgtat
-137  ttgaaatttc aattagttca ttcaaatata cacgtaatag cattataagc cactttcaca
-77   acagatagat tagggttttt aaaatttcaa ccaatgatat ttactataaa ttgatcatgc
-17   acaaaccta attgagcaac acaatttctt acagcaataa ctatcacata taacaataac
       M  A  S  A  K  I  F  L  I  F  L  L  A  A  L ... (SEQ ID NO:49)
+44   tgccatggct tcagcaaaaa ttttcttgat tttccttttg gctgcatta (SEQ ID NO:50)
```

FIGURE 9

UTILITY OF PHYLLOPLANINS AS ANTIBIOTICS, SELECTIVE FUNGICIDES AND FOR ENHANCING MICROBIAL RESISTANCE IN PLANTS

CROSS-REFERENCE TO RELATED APPLICATIONS

This application is a continuation in part of application Ser. No. 11/304,528, filed Dec. 15, 2005, which claims priority under 35 U.S.C. §119 to U.S. Provisional Application Ser. No. 60/682,814, filed May 20, 2005, the disclosures of which are incorporated herein by reference.

TECHNICAL FIELD

Methods of producing and using compositions useful as antimicrobial agents are provided. More particularly, these compositions involve the use of phylloplanin proteins.

BACKGROUND

The need for new antimicrobial agents that prevent or treat plant and animal diseases increases as pathogens gain resistance to existing antimicrobials. In agriculture, available approaches for inhibiting and preventing crop and seed loss due to fungal diseases are inadequate in many cases. Fungi, e.g., basidiomycetes and ascomycetes, and fungi-like pathogens, e.g., oomycete, are significant causes of disease in many seeds and plants, including tobacco, grains, fruits, and vegetables, as well as grasses, e.g., turfgrass. In 1979, an epidemic of blue mold (caused by the oomycete *Peronospora tabacina*) caused an estimated $1.1 billion loss of tobacco crops in Ontario.

Furthermore, the use some currently marketed topical fungicides have drawbacks, e.g., some are thought to be hazardous to the environment, toxic to mammals, or raise other public concerns (e.g., concerns about the possible estrogenic properties of "natural" paraben preservatives in cosmetics). Thus there is a need for alternative natural antimicrobial agents that do not have these perceived disadvantages.

SUMMARY

This invention provides a family of phylloplanins, plant proteins produced by a plant's epidermal layer that contribute to the innate pest/disease resistance of the plant. Phylloplanins are produced by and secreted to the aerial surfaces of many higher plants and vary in molecular size and other properties. A phylloplanin described herein was first identified by washing *Nicotiana tabacum* leaves with water, lyophilizing the wash solution, resuspending the lyophilized material in water to give a leaf water wash (LWW) sample, and analyzing LWW by SDS-PAGE (FIG. 1). As described herein, phylloplanins from tobacco (Shepherd et al., The Plant Cell 17: 1851-1861, 2005; Trends in Plant Science 12: 51-56, 2007; Plant Physiology, 144), sunflower, e.g. *Helianthus annus*, and *Datura*, e.g., *Datura metel*, inhibit germination and growth of the blue mold pathogen (belonging to the oomycete, a fungus-like pathogen class), and *Pyricularia grisea*, a basidiomycete class fungus that causes grey leaf spot on turf grasses, and phylloplanins from tobacco and sunflower also inhibit the germination and growth of *Rhizctonia solani*, an ascomycete class fungus that causes Brown Patch disease on turf grasses and Target Spot disease on tobacco. Thus, phylloplanin polypeptides of this invention have broad-spectrum anti-fungal activity (active against pathogens from three of the 4 major classes of fungal pathogens).

This invention relates to phylloplanin polypeptides, substantially purified phylloplanin polypeptides and compositions comprising phylloplanin polypeptides, particularly phylloplanin polypeptides from broadleaf plants, e.g., tobacco, sunflower and *Datura*, that have antimicrobial activity, particularly a broad spectrum anti-fungal activity. Antifungal as used herein refers to inhibition of germination and/or growth of fungi, e.g., ascomycetes and basidiomycetes, and fungi-like organisms, e.g., oomycetes. In one aspect of this invention the phylloplanin polypeptides, in their natural state, are hydrophobic, basic and often glycosylated, and may have a molecular weight of from about 10 kD to about 75 kD, preferably about 10 kD to about 30 kD. The phylloplanin polypeptides of this invention isolated from plants and compositions comprising the phylloplanin polypeptides inhibit germination and/or growth of fungi and fungi-like organisms, preferably basidiomycetes, ascomycetes and/or oomycetes.

Also an aspect of this invention are compositions comprising the phylloplanin polypeptides or substantially purified phylloplanin polypeptides of this invention and variants or fragments thereof. Preferably the compositions of this invention comprise a polypeptide having the amino acid sequence set forth in SEQ ID NO:18, or a fragment of SEQ ID NO:18 having antimicrobial activity, for example the sequence encompassed by amino acids residues 22-150, 23-150 or 24-150 of SEQ ID NO:18. The compositions may also comprise a polypeptide having the amino acid set forth in SEQ ID NO: 38 or a fragment of SEQ ID NO:18 having antimicrobial activity. The compositions may also comprise a variant of these phylloplanin polypeptides or fragment thereof. The phylloplanin polypeptides, substantially purified phylloplanin polypeptides and compositions comprising phylloplanin polypeptides or fragments or variants thereof having antimicrobial activity are suitable for suppressing microbial growth on a subject, an organism or a surface that is susceptible to fungal infection (e.g., plants and animals).

The phylloplanin polypeptides, substantially purified phylloplanin polypeptides and compositions comprising the phylloplanin polypeptides of this invention, or fragments or variants thereof having antimicrobial activity, may be used to inhibit microbial growth, particular germination or growth of a fungus and a fungus-like organism, on plants or their seeds, that are susceptible to infection by the microbes. Thus, also an aspect of this invention are compositions useful for treating plants that are susceptible to microbial infections wherein the compositions comprise proteins consisting essentially of phylloplanins having anti microbial, particularly anti-fungal, activity and preferably phylloplanins of tobacco, sunflower or *Datura*. The plants may be treated prior to, or subsequently, to infection with the microbe to inhibit progression of the disease.

A variant of the polypeptides of this invention may contain conservative substitutions of amino acids within the sequence, but is at least 80% identical, preferably greater than 80% identical, more preferably at least 90% identical and most preferably at least 95% identical, to SEQ ID NO:18, or to a fragment of SEQ ID NO:18, having antimicrobial activity (for example the sequences encompassed by amino acids residues 22-150, 23-150 or 24-150 of SEQ ID NO:18), and is at least 50%, preferably at least 70%, more preferably at least 80% and most preferably at least 90% as effective as an equal molar amount of SEQ ID NO:18 in inhibiting germination and/or growth of a fungus or fungus-like organism, e.g., basidiomycetes, ascomycetes and/or oomycetes, on a subject, organism or surface, e.g., an animal or plant.

This invention also relates to an isolated nucleic acid molecule comprising the polynucleotide sequence set forth in SEQ ID NO: 17 or the portion of SEQ ID NO: 17 that encodes the amino acid sequence of residues 22-150, 23-150 or 24-150 of SEQ ID NO:18, or a homolog thereof with >80% identity preferably at least 90% identity and more preferably at least 95% identity. The invention further relates to a polypeptide encoded by the polynucleotide sequence of SEQ ID NO: 17 or a homolog thereof with >80% identity, preferably at least 90% identity and more preferably at least 95% identity e.g., SEQ ID NO:18, that have antimicrobial activity. The invention further relates to a polypeptide encoded by the polynucleotide sequence of SEQ ID NO: 17 or homologs thereof, that encodes the amino acid sequence of residues 22-150, 23-150 or 24-150 of SEQ ID NO:18.

The invention further relates to a method of inhibiting microbial proliferation in or on a plant, e.g., by overexpression of a phylloplanin gene in the plant, or contacting an infected plant with a phylloplanin polypeptide, and in or on a surface by contacting the surface with a phylloplanin polypeptide.

The invention further provides a novel promoter sequence that is useful for expression of a protein of interest in a host cell, e.g., a plant cell. In accordance with the invention, a nucleic acid construct is provided comprising a non-coding regulatory domain isolated from a phylloplanin gene, wherein said non-coding regulatory domain is operably associated with a nucleic acid molecule having a sequence which encodes a protein of interest, wherein said nucleic acid molecule is heterologous to said non-coding regulatory domain, and wherein the non-coding regulatory domain comprises a sequence at least 80% identical to the sequence set forth in SEQ ID NO:34. The construct comprises a transcriptional and translational initiation region and translational termination region functional in plants.

The invention further relates to plants selected from the group consisting of corn, soybean, tobacco, potato, tomato, pepper, *Datura*, alfalfa, cucumber, *medicago*, *vitis* sp and grasses, e.g., turf grasses and the like, genetically modified by a polypeptide of the invention.

The invention further relates to a method of inhibiting microbial proliferation in or on an organism comprising administering a therapeutically effective amount of a phylloplanin polypeptide.

The invention further relates to a method of screening endogenous proteins from a plant leaf surface for antimicrobial properties, the method comprising a) washing the plant leaf surface with an aqueous solution; b) collecting the aqueous solution after washing; and c) analyzing the solution for proteins having antimicrobial, e.g., antibacterial or antifungal, properties.

The invention further relates to methods of screening endogenous plant proteins for antimicrobial activity, comprising obtaining the proteins from a plant, e.g., the leaf surfaces, for antimicrobial activity. Preferably the proteins are obtained from of a species selected from the group consisting of *Medicago* sp., *Trifolium* sp., *Ulmus* sp., *Pyrus malus*, *Prunus armeniaca*, *Cynara acolymus*, *Asparagus officinale*, *Hordeum* sp., *Galium* sp., *Beta vulgaris*, *Prunus serotina*, *Vigna sinensis*, *Nyssa sylvatica*, *Quercus* sp., *Artocarpus altilis*, *Brassica* sp., *Andropogon scoparius*, *Fagopyrum sagittatum*, *Manihot esculenta*, *Apium graveolens*, *Agropyron desertorum*, *Cornus florida*, *Phaseolus* sp., *Triticum* sp., *Oenothera caespitosa*, *Carya* sp., *Lactuca* sp., *Impatiens* sp., *Helianthus* sp., *Ledum decumbens*, *Astragalus pattersoni*, *Setaria italica*, *Vaccinium mytrillus*, *Avena sativa*, *Petroselinum crispum*, *Pastinaca sativa*, *Pisum* sp., *Prunus* sp., *Pyrus communis*, *Musa paradisiaca*, *Astragalus preussii*, *Raphanus sativus*, *Secalse cereale*, *Sassafras albidum*, *Atriplex confertifolia*, *Tillandsia usneoides*, *Spinacia oleracea*, *Liquidambar styraciflua*, *Linaria triphylla*, *Liriodendron tulipfera*, *Vicia* sp., *Citrullus vulgaris*, *Melilotus* sp., *Salix* sp., *Rhus copallina*, *Nicotiana* sp., *Vitis* sp., *Datura* sp., *Medicago* sp., *Lycopersicon* sp., *Solanum* sp., *Capsicum* sp., *Cucumis* sp., *Fragaria* sp., *Petunia* sp., *Geranium* sp., *Coleus* sp., *Stevia* sp., *Oryza* sp., *Nepeta* sp., *Zea mays*, *Glycine max*, and assayed for antimicrobial activity, preferably anti-fungal activity, and more preferably for the ability to inhibit germination and/or growth of an oomycetes, a basidiomycetes or an ascomycetes, e.g., *P. tabacina*, *Pyricularia grisea*, and *Rhizctonia solani*.

Phylloplanins are persistent on leaf surfaces and therefore do not appear to be light sensitive.

Although we do not know if the phylloplanins of this invention are toxic to animals, surface proteins occur on many vegetables, which are consumed fresh (lettuce, cabbage) by mammals, and several spice species that are used as fresh and dry-leaf food additives without adverse effects. The toxicity of phylloplanins for mammals and other animals may be readily assayed using conventional techniques and if they are found to be toxic, suitable precautions may easily be instituted to reduce exposure of mammals or other animals to the phylloplanins.

The invention provides phylloplanin polypeptides, substantially pure phylloplaninin polypeptides and variants and fragments thereof, having antimicrobial activity, preferably anti-fungal activity, and methods of using such polypeptides and compositions comprising such polypeptides, to enhance microbial, preferably fungal, resistance in plants. In addition, the invention demonstrates that the phylloplanin polypeptides of this invention are antimicrobial proteins useful in molecular farming products. Phylloplanins have the potential to be used as antibiotics against human and animal microorganisms. Overexpression of phylloplanin genes in plants such as corn, soybean, tobacco, tomato, potato, pepper, *Datura*, alfalfa, cucumber, *medicago*, *vitis* sp, grasses, e.g., turfgrass, and the like enhances plant resistance to fungal and bacterial microorganisms. In addition, the phylloplanin polypeptides of this invention can be used as a topical fungicide.

Other aspects of the invention are described throughout the specification.

Figure 1:
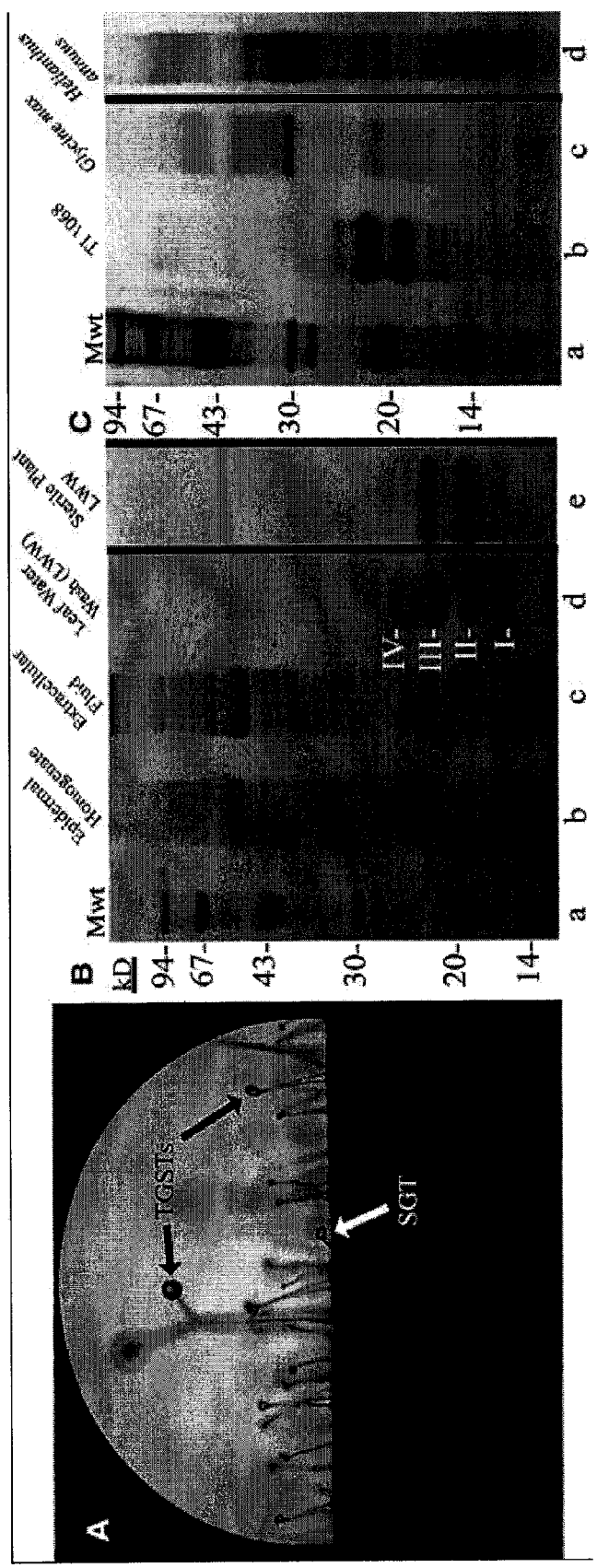
FIG. 1A-C depicts data demonstrating proteins present on plant leaf surfaces. A: 40× magnification of TI 1068 phylloplane with tall glandular secreting trichomes (TGSTs) and short glandular trichome (SGTs) identified. B: Coomassie-stained SDS-PAGE of TI 1068-derived samples. Phylloplanins I-IV are identified. Loaded volumes of leaf water wash (LWW) (B,d) and sterile-grown plant LWW (B,e) represent 25 cm$^2$ leaf surface area. Mwt (B,a) denotes protein standards. C: Silver-stained SDS-PAGE of LWWs from field-grown TI 1068 (C,b; 10 cm$^2$), *G. max* (C,c; 30 cm$^2$), and *H. annuus* (C,d; 6 cm$^2$). Mwt (C,a) denotes protein standards.

Arrow marks residual, soluble ProtK. B: *P. tabacina* leaf infection assay of Petite Havana. a, water+spores ($10^4$ spores/ml). A sporulating lesion is indicated with arrow. b, TI 1068 LWW (diluted to 50 ng/µl)+spores ($10^4$ spores/ml).

FIG. 3 provides a nucleotide sequence (SEQ ID NO:17) and predicted amino acid sequence (SEQ ID NO:18) of TI 1068 Phylloplanin. Nucleotides are numbered on right. Start and stop codons are underlined, and the signal sequence is bold-faced. Segments corresponding to peptides amino acid-N1, amino acid-T1, amino acid-T2, amino acid-T3, amino acid-T4, and amino acid-P1 are marked by lines above the amino acid sequence and labeled.

FIG. 4A-D demonstrates *E. coli*-expressed TI 1068 phylloplanin inhibition of *P. tabacina* spore germination. Coomassie-stained SDS-PAGE (sds), western blots with 1:10,000 phylloplanin antiserum (w), and *P. tabacina* spore germination assays (Pt). a: *E. coli* expressed MBP-PhyllP (M-P; 160 ng/μl total protein) treated with Factor-Xa. Arrow indicates released PhyllP. b: *E. coli* expressed MBP-PhyllP (160 ng/μl total protein) treated with Factor-Xa and Proteinase-K (ProtK). Volume used was equivalent to (a). c: *E. coli* expressed MBP (M; 200 ng/μl total protein treated with Factor-Xa. d: *E. coli* expressed MBP (200 ng/μl total protein) treated with Factor-Xa and ProtK Volume used was equivalent to (c).

FIG. 5A-C shows that the phylloplanin promoter directs protein expression in short glandular trichomes (SGTs). A: Magnification of X-gluc stained plantlet leaf from TI 1068 with GUS under control of phylloplanin promoter. Tall glandular secreting trichomes (TSGTs) are also indicated. B: X-gluc stained SGT on TI 1068 plantlet expressing GUS under control of phylloplanin promoter. Surface structures are indicated. C: Fluorescent magnification/detection of TI 1068 plantlet with GFP under control of phylloplanin promoter. GFP was present only in SGT gland cells. The yellow arrows indicate constrictions between gland cells that may be "pores" to release protein to the leaf surface.

FIG. 6 depicts growth curves of *E. coli* BL21 cultures expressing *N. tabacum* PR-5a and *A. thaliana* AAP75801 with the pET-30 system. Induction with IPTG, if performed, occurred at 2.25 hrs. The IPTG-induced PR-5a expressing culture continued logarithmic growth along with control BL21 cells and non-IPTG-induced cultures. The IPTG-induced AAP75801 expressing culture seemed to stop growing. This suggests that the induced AAP75801 protein product was toxic towards the culture.

FIG. 7 depicts inhibition of *P. tabacina* Spore Germination and Leaf Infection by T-Phylloplanins in LWW. For both assays, the results of a single experiment that is representative of three separate experiments are shown. Open circles, spore germination; closed squares, leaf infection.

FIG. 8A-B depicts multiple alignment and phylogenetic analysis of T-phylloplanin and similar sequences in other plants (SEQ ID NOs: 18 and 36-48, respectively). A: The amino acid sequence of T-phylloplanin was aligned against sequences giving significant BLAST similarity scores using the ClustalW algorithm of DNASTAR (Lasergene Software, Madison, Wis.). Amino acids conserved between any six sequences are indicated in reverse contrast. B: Unrooted phylogenetic tree showing the evolutionary relationships between the sequences in (A). Bootstrap values of >50% are given on the respective branches. The first two letters of the acronyms indicate the species (Am, *Antirrhinum majus*; At, *Arabidopsis thaliana*; Br, *Brassica rapa*; Gm, *Glycine max*; Ha, *Helianthus annuus*; Le, *Lycopersicon eschulentum*; Nt, *Nicotiana tabacum*; Os, *Oryza sativa*; Pt, *Populus tremuloides*; Sr, *Stevia rebaudiana*; St. *Stevia tuberosum*). The GenBank accession numbers of the sequences follow the species identifiers. Tissue localizations of ESTs and cDNAs are indicated beneath the acronyms.

FIG. 9 depicts the promoter sequence of the gene Phylloplanin (SEQ ID NOS:49 and 50). A putative TATA box (2-33 to −30) and a putative CAAT box (−47 to −43) are bold-faced. The phylloplanin transcription start site (+1) is bold-faced and underlined. The phylloplanin start codon (+48) is underlined. A portion of the phylloplanin amino acid sequence is indicated.

FIG. 10A-E depicts the effects of spraying LWW containing T-phylloplanin on grasses prior to inoculation with mycelia of *Pyricularia grisea* (A, B) or *Rhizctonia solani* (C, D, E). AR is annual rye grass (*Lolium multiflorum*) (B), PR is perennial rye grass (*Lolium perenne*) (A, D), and CB is creeping bentgrass (*Agrostis palustris*) (C). T-phyllo is tobacco LWW containing T-phylloplanin. Pots labeled "a" (left) are phylloplanin treated, Pots labeled "b" (center) are ProteinaseK digested phylloplanin treated, and Pots labeled "c" (right) are ProteinaseK control treated (no phylloplanin). Note the healthy growth in the left-most pots of each set, and deterioration in the center and right situated pots where phylloplanin was protease pre-treated, or protease control was applied. Insets show symptoms of diseases on leaf blades of pot c, and healthy leaf blades in pot a.

FIG. 11A-E depicts the effects of spraying LWW containing S-phylloplanin on grasses prior to inoculation with mycelia of *Pyricularia grisea* (A, B) or *Rhizctonia solani* (C, D, E). Designations are as described in the legend of FIG. 10.

FIG. 12A-D: In vitro, petri-plate, filter-paper-disc assays of T-phylloplanin effects (A and B) and S-phylloplanin effects (C and D) on growth of *Pyricularia grisea* (A and C), or *Rhizctonia solani* (B and D). Pristine™ (upper disc) was used as a positive inhibition control. Water (lower disc) was used as a solution control. LWWs containing T-, or S-phylloplanins were applied in water. Phylloplanin pre-treated with ProteinaseK to destroy phylloplanins is at the left in each case, and phylloplanin not treated with ProteinaseK is at the right. ProteinaseK controls showed no inhibition (not shown). A clear zone of inhibition (arrows) was observed with Pristine™ and T-, or S-phylloplanin containing LWW in all cases.

FIG. 13: Protease sensitivity of tobacco, jimson weed, sunflower and soybean phylloplanins. Lane 1 contains $M_r$ markers. Lanes 2 and 3, tobacco LWW, + and − Proteinase K, respectively; lanes 4 and 5, sunflower LWW, + and − Proteinase K, respectively; lanes 6 and 7, jimson weed LWW, + and − ProteinaseK, respectively; lanes 8 and 9, soybean LWW, + and − ProteinaseK, respectively. Protein bands at approximately 32 kD in lanes 2, 4, 6, and 8 are soluble ProteinaseK released during digestions. All samples contained 15 $cm^2$asae of LWW.

DETAILED DESCRIPTION

The invention is directed to phylloplanin polypeptides having antimicrobial, preferably antifungal, activity and to compositions comprising the phylloplanin polypeptides. The invention also relates to methods of using the phylloplanin polypeptides to inhibit microbial, preferably fungal and fungus-like, infection and disease of plants and animals, preferably humans, and to inhibit the germination and growth of fungus and fungus like organisms in or on the surface of materials that are susceptible to infection by e.g., bacteria, fungus or fungus-like organisms.

DEFINITIONS

To facilitate understanding of the invention set forth in the disclosure that follows, a number of terms are defined below.

The term "innate immunity" refers to a defense system that inhibits growth of microorganisms at their first point of contact.

The term "phylloplane" refers to a plant's epidermal layer that contributes to the innate pest/disease resistance of the plant.

The term "phylloplanins" refers to proteins produced by a plant's epidermal layer that contribute to the innate pest/disease resistance of the plant.

The term "TGSTs" refers to the tall glandular secreting trichome.

The term "SGTs" refers to the short glandular trichome.

The term "LWW" refers to leaf water washes.

T-phylloplanin as used herein refer phylloplanins from tobacco.

S-phylloplanin as used herein refer phylloplanins from sunflower.

D-phylloplanin as used herein refer phylloplanins from *Datura*.

The meaning of other terminology used herein should be easily understood by someone of ordinary skill in the art.

Fungicides are commonly used to inhibit fungal disease in plants, and are commercially available and used for preventing crop loss. Examples of such fungicides are listed in the following table.

| FRAC CODE[1] | TARGET SITE[2] | GROUP NAME[3] | CHEMICAL GROUP[4] | COMMON NAME[5] | COMMENTS[6] |
|---|---|---|---|---|---|
| 1 | mitosis: β-tubuline assembly | MBC - fungicides (Methyl Benzimidazole Carbamates) | benzimidazoles benomyl carbendazim thiophanates | Fuberidazole thiabendazole thiophanate thiophanate-methyl | Resistance common in many fungal species. Several target site mutations, mostly E198A/G/K, F200Y Positive cross resistance between the group members. Negative cross resistance to N-Phenylcarbamates High risk. See FRAC Benzimidazole Guidelines for resistance management. |
| 2 | NADH cytochrome c reductase in lipid peroxidation (proposed) | decarboximides | | chlozolinate iprodione procymidone vinclozolin | Resistance common in *Botrytis cinerea* and found in some other fungal species. Several mutations found in OS1 histidine kinase (Daf 1), mostly 1365S Cross resistance common between the group members. Medium to high risk. See FRAC Dicarboximide Guidelines for resistance management. |
| 3 | C14-demethylation in sterol biosynthesis | DMI-fungicides (DeMethylation Inhibitors) (SBI: Class I) | imidazoles<br><br>piperazines pyridines pyrimidines<br><br>triazoles | imazalil pefurazoate prochloraz triflumizole triforine pyrifenox fenarimol nuarimol azaconazole bitertanol bromuconazole cyproconazole difenoconazole diniconazole epoxiconazole fenbuconazole fluquinconazole flusilazole flutriafol hexaconazole imibenconazole ipconazole metconazole | There are great differences in the activity spectra of the different DMI fungicides. Resistance is known in various fungal species. Several resistance mechanisms known incl. target site mutation YI36F, ABC transporters and others. |

| FRAC CODE[1] | TARGET SITE[2] | GROUP NAME[3] | CHEMICAL GROUP[4] | COMMON NAME[5] | COMMENTS[6] |
|---|---|---|---|---|---|
| | | | | myclobutanil penconazole propiconazole prothioconazole simeconazole tebuconazole tetraconazole triadimefon triadimenol triticonazole | Generally wise to accept that cross resistance is present between fungicides active against the same fungus. DMI fungicides are Sterol Biosynthesis Inhibitors (SBI's) but show no cross resistance to other SBI classes. Medium risk. See FRAC SBI Guidelines for resistance management. |
| 4 | RNA polymerase I | PA - fungicides (PhenylAmides) | acylalanines | benalaxyl furalaxyl metalaxyl metalaxyl-M (=mefenoxam) oxadixyl ofurace | Resistance and cross resistance well known in various Oomycetes but mechanism unknown. High risk. See FRAC Phenylamide Guidelines |
| | | | oxazolidinones butyrolactones | | |
| 5 | $\Delta_{14}$-reductase and $\Delta_8$-$\Delta_7$ isomerase in sterol biosynthesis | Amines ("Morpholines") (SBI: Class II) | morpholines | Aldimorph dodemorph fenpropimorph tridemorph | Decreased sensitivity described for powdery mildews. Cross resistance within the group generally found but not to other SBI classes. Low to medium risk. See FRAC SBI Guidelines for resistance management. |
| | | | piperidines | fenpropidin piperalin | |
| | | | spiroketalamines | spiroxamine | |
| 6 | phospholipid biosynthesis, methyltransferase | phosphorothiolates | | edifenphos iprobenfos (IBP) pyrazophos isoprothiolane | Resistance known for specific fungi. Low to medium risk. Resistance management required if used for risky pathogens. |
| | | dithiolanes | | | |
| 7 | complex II in fungal respiration (succinate-dehydrogenase) | carboxamides | | benodanil boscalid carboxin fenfuram flutolanil furametpyr mepronil oxycarboxin thifluzamide | Resistance know for specific fungi.. Target site mutation H257L. Medium risk. Resistance management required if used for risky pathogens. |
| 8 | adenosine-deaminase | hydroxyl-(2-amino-) pyrimidines | | bupirimate dimethirimol thirimol | Medium risk. Resistance and cross resistance known in powdery mildews. Resistance management required. |
| 9 | methionine biosynthesis | AP - fungicides (Anilino- | | cyprodinil mepaniprim | Resistance known in |

| FRAC CODE[1] | TARGET SITE[2] | GROUP NAME[3] | CHEMICAL GROUP[4] | COMMON NAME[5] | COMMENTS[6] |
|---|---|---|---|---|---|
| | (proposed) | Pyrimidines) | | pyrimethanil | Botrytis and sporadically in Venturia, mechanism speculative (CGS). Medium risk. See FRAC Anilinopyrimidine Guidelines for resistance management |
| 10 | mitosis: β-tubulin assembly | N-phenyl carbamates | | diethofencarb | Resistance known. Target site mutation E198K. Negative cross resistance to benzimidazoles. High risk. Resistance management required. |
| 11 | complex III of fungal respiration: ubiquinol oxidase, Qo site | QoI-fungicides (Quinone outside Inhibitors) | methoxy-acrylates Methoxy-carbamates Oximino acetates Oximino-acetamides Oxazolidine-diones dihydro-dioxazines imidazolinones | Azoxystrobin picoxystrobin Pyraclostrobin Kresoxim-methyl trifloxystrobin metominostrobin Famoxadone fluoxastrobin fenamidone | Resistance known in various fungal species. Target site mutations G143A, F129L and additional mechanisms. Cross resistance shown between all members of the QoI group. High risk. See FRAC QoI Guidelines for resistance management. |
| 12 | MAP protein kinase in osmotic signal transduction | PP-fungicides (PhenylPyrroles) | | fenpicolonil fludioxonil | Resistance found sporadically, mechanism speculative (OS-2 kinase). Low to medium risk. Resistance management required. |
| 13 | G-proteins in early cell signalling (proposed) | quinolines | | quinoxyfen | Resistance known. Medium risk. Resistance management required. |
| 14 | lipid peroxidation (proposed) | AH-fungicides (Aromatic Hydrocarbons) (chlorophenyls, nitroanilines) heteroaromatics | 1,2,4-thiadiazoles | biphenyl chloroneb dicloran quintozene (PCNB) tecnazene (TCNB) tolclofos-methyl etridiazole | Resistance known to some fungi. Low to medium risk. Cross resistance patterns complex due to different activity spectra. |
| 15 | cell wall sythesis (proposed) | cinnamic acids | | dimethomorph | Low to medium risk. Resistance management required. |
| 16.1 | reductase in melanin biosynthesis | MBI-R (Melanin Biosynthesis Inhibitors - Reductase) | isobenzofuranone pyrroloquinolinone triazolobenzo-thiazole | fthalide pyroquilon tricyclazole | Resistance not known |
| 16.2 | dehydratase in melanin biosynthesis | MBI-D (Melanin Biosynthesis Inhibitors - | cyclopropane-carboxamide carboxamide | carpropamid diclocyme fenoxani | Resistance known. Medium risk. |

-continued

| FRAC CODE[1] | TARGET SITE[2] | GROUP NAME[3] | CHEMICAL GROUP[4] | COMMON NAME[5] | COMMENTS[6] |
|---|---|---|---|---|---|
| | Dehydratase) | | propionamide | | Resistance management required. |
| 17 | 3-keto reductase during C4 demethylation in sterol biosynthesis | hydroxyanilides (SBI: Class III) | | fenhexamid | Low to medium risk. Resistance management required. |
| 18 | squalene epoxidase in sterol biosynthesis | (SBI: class IV) | thiocarbamates allylamines | pyributicarb naftifine terbinafine | Resistance not known. Herbicide and fungicide. Medical fungicides |
| 19 | chitin synthase | polyoxins | peptidyl pyrimidine nucleoside | polyoxin | Resistance known. Medium risk. Resistance management required. |
| 20 | cell division (proposed) | phenylureas | | pencycuron | Resistance not known |
| 21 | complex III of fungal respiration: ubiquinone reductase, Qi site | QiI - fungicides (Quinone inside Inhibitors) | cyanoimidazole | cyazofamid | Resistance risk unknown but assumed to be medium to high (mutations at target side known in model organisms). Resistance management required. |
| 22 | mitosis β-tubulin assembly | benzamides | | zoxamide | Low to medium risk. Resistance management required. |
| 23 | protein synthesis | enopyranuronic acid antibiotic | | blasticidin-S | Low to medium risk. Resistance management required. |
| 24 | protein synthesis | hexopyranosyl antibiotic | | kasugamycin | Medium risk. Resistance known. Resistance management required. |
| 25 | protein synthesis | glucopyranosyl antibiotic | | streptomycin | Bactericide. Resistance known. High risk. Resistance management required. |
| 26 | trehalase and/or inositol-biosynthesis | glucopyranosyl antibiotic | | validamycin | Resistance not known |
| 27 | unknown | cyanoacetamide-oximes | | cymoxanil | Resistance claims described. Low to medium risk. resistance management required. |
| 28 | cell membrane permeability, fatty acids (proposed) | carbamates | | iodocarb propamocarb prothiocarb | Low to medium risk. Resistance management required. |
| 29 | uncoupler of oxidative phosphorylation | | dinitrophenyl crotonates pyrimidinone-hydrazones 2,6-dinitro-anilines | binapacryl dinocap ferimzone fluazinam | Resistance not known Resistance not known Low risk. However, resistant isolates of Botrytis claimed to exist in Japan in 2000 |

-continued

| FRAC CODE[1] | TARGET SITE[2] | GROUP NAME[3] | CHEMICAL GROUP[4] | COMMON NAME[5] | COMMENTS[6] |
|---|---|---|---|---|---|
| 30 | inhibitors of oxidative phosphorrylation, ATP synthases | organo tin compounds | tri phenyl tin compounds | fentin acetate fentin chloride fentin hydroxide | Some resistance cases known. Low to medium risk |
| 31 | DNA topoisomerase type II (gyrase) | carboxylic acids | | oxolinic acid | Bactericide. Resistance known. Resistance management required. |
| 32 | DNA/RNA synthesis (proposed) | heteroaromatics | isoxazoles isothiazolones | hymexazole octhilinone | Resistance not known |
| 33 | unknown | phosphonates | ethyl phosphonates | fosetyl-Al phophorous acid | Miscellanous compounds, mode of action generally not known |
| 34 | unknown | phthalamic acids | | teclofthalam (Bactericide) | |
| 35 | unknown | benzotriazines | | triazoxide | |
| 36 | unknown | benzene-sulfoanamides | | | |
| 37 | unknown | pyridazinones | | diclomezine | Use over several years has not revealed major resistance problems. Risk assumed to be low. No cross resistance between group members |
| P | host plant defense induction | P1 salicylic acid pathway P2 | benzo-thiadiazole BTH benzisothiazole | acibenzolar-S-methyl probenazole (also antibacterial and antifungal activity) | Resistance not known |
| U | cell wall synthesis (proposed) ATP production in respiration (proposed) complex I of respiration (proposed) unknown Unknown | U1 U2 U3 U4 U5 | amino acid amide carbamates thiophene-carboxamides pyrimidinamines thiocarbamate thiazole-carboxamides | benthiavalicarb iprovalicarb silthiofam Diflumetorim methasulfocarb ethaboxam | Mode of action and resistance risk unknown. No log term experience available. Resistance management required if high risk oraganisms are targeted. No cross resistance between group members |
| M | multi-site contract acitivty | M1 M2 M3 M4 M5 M6 M7 M8 | inorganics dithio-carbamates and relatives phthalimides chloronitriles (phthalonitriles) sulphamides guanidines triazines quinones | Copper (different salts) Sulphur ferbam mancozeb maneb metriram propineb thiram zineb ziram captan captafol folpet chlorothalonil dichlofluanid tolylfluanid dodine guazatine iminoctadine anilazine dithianon | Gerally considered a low risk group with no signs of resistance developing to the majority of fungicides. No cross resistance between Group members. |

| FRAC CODE[1] | TARGET SITE[2] | GROUP NAME[3] | CHEMICAL GROUP[4] | COMMON NAME[5] | COMMENTS[6] |
|---|---|---|---|---|---|
| | | M9 | (enthraquinoes) inorganics | | |
| | | | | Copper (different salts) Sulphur | |

Source: www.frac.info/publications/frac_list01
[1]FRAC Code. Numbers and letters are used to distinguish the fungicide groups. The numbers were assigned primarily according to the time of product introduction to the market. The letters refer to P = host plant defense inducers, M = multi-site inhibitors, and U = recent molecules with unknown mode of action.
[2]Target Site of Action. If available the biochemical mode of action is given. In many cases the precise target site is not known. However, a grouping can be made due to cross resistance profiles within a group or in relation to other groups.
[3]Group Name. The Group Names listed are widely accepted in literature. They are based on different sources (mode of action, first important representative, chemical group).
[4]Chemical Group. Sub-grouping due to chemical considerations.
[5]Common name. Accepted (or proposed) common name for an individual active ingredient expected to appear on the product label as definition of the product.
[6]Comments on Resistance. If field resistance is known to one member of the Group, it is most likely but not exclusively valid that cross resistance to other Group members will be present. There is increasing evidence that cross resistance may not be clearly visible between Group members and that the degree of the effect can differ both between group members and fungal species or even within species. The intrinsic risk for resistance evolution to a # given fungicide group is estimated to be low, medium or high according to the principles described in FRAC Monographs 1 and 2. A similar classification list of fungicides was published recently also by T. Locke on behalf of FRAC - UK (Fungicide Resistance, August 2001) and by P. Leroux (Classification des fongicides agricoles et resistance, Phytoma, La Defense des Vegetaux, No. 554, 43-51, November 2002).

Phylloplanins

Phylloplanins are expressed in crop plants such as corn, soybean, tobacco, tomato, potato, pepper, sunflower, *Datura*, alfalfa, cucumber, *vitris* sp, *medicago*, and the like. Typical biological activities or functions associated with this family of polypeptides, particularly those isolated from broadleaf plants, e.g., tobacco, sunflower and *Datura*, as described herein, include, e.g., inhibition of fungal spore germination. In one aspect of the invention phylloplanin polypeptides include oligomers or fusion polypeptides comprising at least one domain portion of one or more phylloplanin, or fragments of any of these phylloplanin that have antimicrobial activity, and preferably are capable of inhibiting fungal germination.

This invention provides a family of polypeptides, termed phylloplanins, and the utility of these polypeptides and homologous polypeptides (>80% homology, commonly >90% homology, more typically >95% homology) from other species as antimicrobials (e.g., antifungals and antibacterials) against human and animal pathogens.

A phylloplanin polypeptide of the invention includes a polypeptide that shares a sufficient degree of amino acid identity or similarity to a polypeptide having a sequence as set forth in SEQ ID NO:18 or the amino acid sequence of residues 22-150, 23-150 or 24-150 of SEQ ID NO: 18, such that it is likely to share particular structural domains, have biological activities in common with the phylloplanin polypeptides of this invention, and/or bind to antibodies that also specifically bind to phylloplanins comprising SEQ ID NO: 18 or the amino acid sequence of residues 22-150, 23-150 or 24-150 of SEQ ID NO: 18. The phylloplanin polypeptides of the invention may be isolated from naturally occurring sources, e.g., from broadleaf plants, e.g., tobacco leaves, sunflower leaves, or *Datura* leaves. Alternatively, the phylloplanin polypeptides may be recombinantly produced and have the same structure as a naturally occurring phylloplanin polypeptide, or may be produced to have structures that differ from naturally occurring phylloplanins but retain a significant amount of antimicrobial activity. Polypeptides derived from any phylloplanin polypeptide of the invention by any type of alteration (for example, but not limited to, insertions, deletions, or substitutions of amino acids, preferably conservative substitutions, changes in glycosylation of the polypeptide, refolding or isomerization to change its three-dimensional structure or self-association state, and changes to its association with other polypeptides or molecules) are also phylloplanin polypeptides for the purposes of the invention. Therefore, the polypeptides provided by the invention include polypeptides characterized by amino acid sequences similar to those of the phylloplanin polypeptides or similar to phylloplanin polypeptides described herein, preferably a phylloplanin comprising the amino acid sequence set forth in SEQ ID NO:18 or the amino acid sequence of residues 22-150, 23-150 or 24-150 of SEQ ID NO: 18, but into which modifications are naturally provided or deliberately engineered. A polypeptide that shares biological activities in common with members of the phylloplanin polypeptide family is a polypeptide having antimicrobial activity, preferably antifungal activity.

Figure 8B:
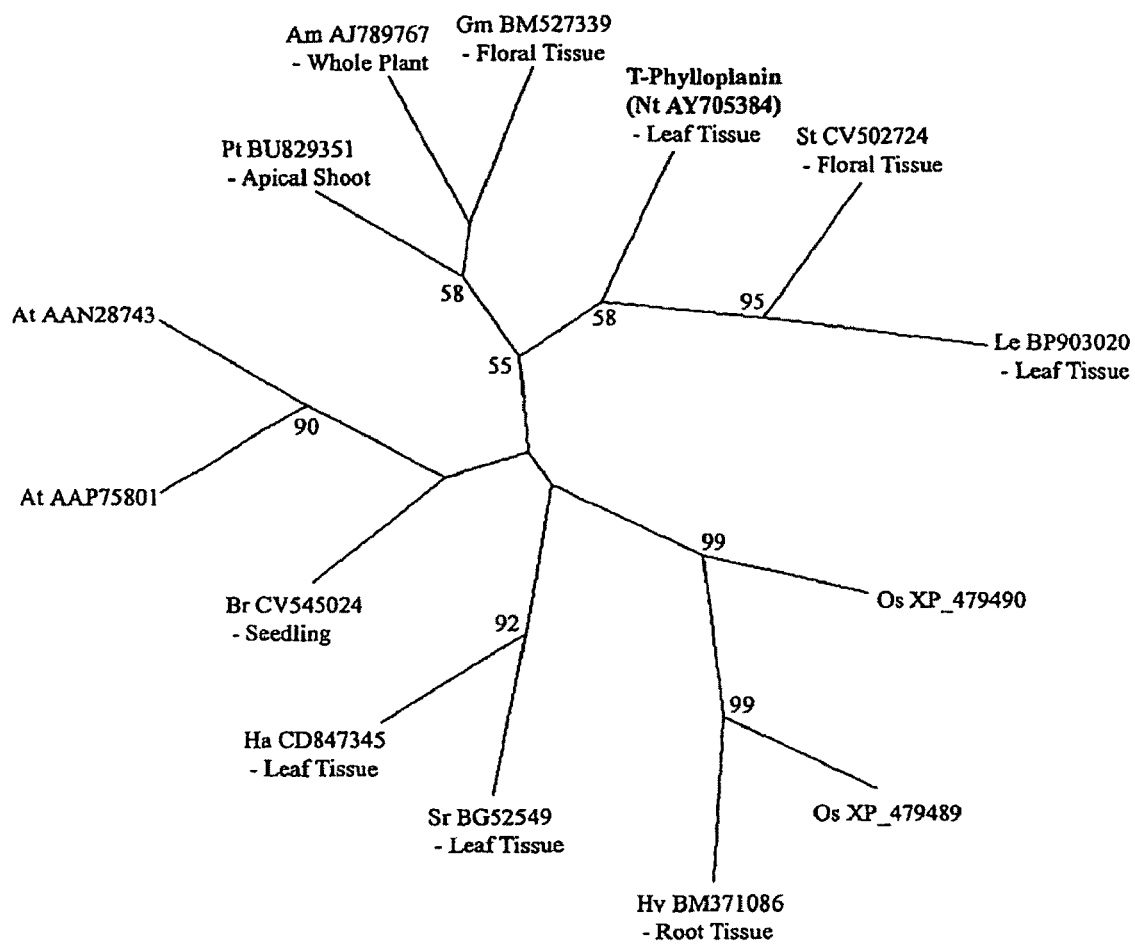

Amino acid substitutions and other alterations (deletions, insertions, and the like) to the phylloplanin amino acid sequences (e.g., SEQ ID NO:18 or the amino acid sequence of residues 22-150, 23-150 or 24-150 of SEQ ID NO: 18) that change the consensus residues of the amino acid sequences, see FIGS. 8A and B, and particularly substitutions of an amino acid with one of dissimilar structure (e.g., such as substitution of any one of the aliphatic residues—Ala, Gly, Leu, Ile, or Val—with another non-aliphatic residue), or substitution or alteration of a residue that is conserved among phylloplanins, are predicted to be more likely to alter or disrupt phylloplanin polypeptide activities. Conversely, a substitution of a residue at a position in the alignment that is not conserved among phylloplanin and phylloplanin-like sequences, is less likely to affect the function of the altered phylloplanin polypeptide. The invention provides phylloplanin polypeptides and fragments of phylloplanin polypeptides, comprising altered amino acid sequences. Altered phylloplanin polypeptide sequences share at least 75% identity, preferably at least 85% to at least 95%, or most preferably at least 99%, identity with the phylloplanin amino acid sequences set forth in SEQ ID NO:18 or the amino acid sequence of residues 22-150, 23-150 or 24-150 of SEQ ID NO: 18.

The invention provides both full-length and mature forms of phylloplanin polypeptides. Particularly preferred "full-length" polypeptides are those having the complete amino acid sequence of the polypeptide as encoded by SEQ ID NO:17. The amino acid sequences of full-length polypeptides can be obtained, for example, by translation of the complete open reading frame ("ORF") of a cDNA molecule (e.g., SEQ ID NO:17). Several full-length polypeptides may be encoded by a single genetic locus if multiple mRNA forms are produced from that locus by alternative splicing or by the use of multiple translation initiation sites. An example of a full length polypeptide of the invention includes the sequence as set forth in SEQ ID NO:18, from amino acid 1 to amino acid 150. The "mature form" of a polypeptide refers to a polypeptide that has undergone post-translational processing steps such as cleavage of the signal sequence or proteolytic cleavage to remove a prodomain. Multiple mature forms of a particular full-length polypeptide may be produced, for example by cleavage of the signal sequence at multiple sites, or by differential regulation of proteases that cleave the polypeptide. The mature form(s) of such polypeptide may be obtained by expression, in a suitable plant cell or other host cell, of a polynucleotide that encodes the full-length polypeptide. The sequence of the mature form of the polypeptide may also be determinable from the amino acid sequence of the full-length form, through identification of signal sequences or protease cleavage sites. An example of a mature form of the polypeptide of the invention is SEQ ID NO:18, from amino acid residue $X_1$ to amino acid residue 150, wherein $X_1$ is an amino acid between and including residues 22, 23 and 24 (e.g., amino acids 22-150, 23-150 or 24-150 of SEQ ID NO:18). The phylloplanin polypeptides of the invention also include those that result from post-transcriptional or post-translational processing, events such as alternate mRNA processing which can yield a truncated but biologically active polypeptide. Also encompassed within the invention are variations attributable to proteolysis such as differences in the N- or C-termini upon expression in different types of host cells, due to proteolytic removal of one or more terminal amino acids from the polypeptide (generally from about 1 to 5 terminal amino acids).

The invention further includes phylloplanin polypeptides with or without associated native-pattern glycosylation. Polypeptides expressed in yeast or plant expression systems (e.g., COS-1 or CHO cells) can be similar to or significantly different from a native polypeptide in molecular weight and glycosylation pattern, depending upon the choice of expression system. Expression of polypeptides of the invention in bacterial expression systems, such as E. coli, typically provides non-glycosylated molecules. Further, a given preparation can include multiple differentially glycosylated species of the polypeptide. Glycosyl groups can be removed through conventional methods, in particular those utilizing glycopeptidase (Boehringer Mannheim).

Species homologues of phylloplanin polypeptides and polynucleotides are also provided by the invention. As used herein, a "species homologue" is a polypeptide or polynucleotide with a different species of origin from that of a given polypeptide or polynucleotide, but with significant sequence similarity to the given polypeptide or polynucleotide. Species homologues may be isolated and identified by making suitable probes or primers from polynucleotides encoding the phylloplanin polypeptides provided herein and screening a suitable nucleic acid source from the desired species. Alternatively, homologues may be identified by screening a genome database containing sequences from one or more species utilizing a sequence (e.g., nucleic acid or amino acid) of a phylloplanin molecule of the invention. Such genome databases are readily available for a number of species (e.g., on the world wide web (www) at tigr.org/tdb; genetics.wisc.edu; stanford.edu/ about ball; hiv-web.lanl.gov; ncbi.nlm.nig.gov; and ebi.ac.uk; pasteur.fr/other/biology). Computer algorithms, which connects two proteins through one or more intermediate sequences, can be used to identify closely related as well as distant homologs. For example, an algorithm that repetitively uses the results of the previous query as new search seeds such as Saturated BLAST can be used. Starting with a protein sequence, Saturated BLAST runs a BLAST search and identifies representative sequences for the next generation of searches. The procedure is run until convergence or until some predefined criteria are met. Saturated BLAST is available on the world wide web (www) at: bioinformatics.burnham-inst.org/xblast (see also, Li et al. Bioinformatics 16(12):1105-1110, 2000).

The invention also encompasses allelic variants of phylloplanin polypeptides and polynucleotides; that is, naturally-occurring forms of such polypeptides and polynucleotides in which differences in amino acid or nucleotide sequence are attributable to genetic polymorphism.

Fragments of the phylloplanin polypeptides of the invention are encompassed by the invention and may be in linear form or cyclized using known methods, for example, as described in H. U. Saragovi, et al., Bio/Technology 10:773-778 (1992) and in R. S. McDowell, et al., J. Amer. Chem. Soc. 114:9245-9253 (1992). Phylloplanin polypeptides and fragments thereof, and the polynucleotides encoding them, include amino acid or nucleotide sequence lengths that are at least 25% (typically at least 50%, 60%, 70%, and, most commonly at least 80%) of the length of a phylloplanin polypeptide or polynucleotide and have at least 60% sequence identity (typically at least 70%, 75%, 80%, 85%, 90%, 95%, 97.5%, or at least 99%, and, most commonly at least 99.5%) with that phylloplanin polypeptide or polynucleotide, where sequence identity is determined by comparing the amino acid or nucleotide sequences when aligned so as to maximize overlap and identity while minimizing sequence gaps. Methods for determining identity are discussed in more details below. Also included in the invention are polypeptides and fragments, and polynucleotides encoding them, that contain or encode a segment comprising at least 8, or at least 10, or at least 15, or typically at least 20, or still more typically at least 30, or most commonly at least 40 contiguous amino acids, preferably of SEQ ID No:18. Such polypeptides and fragments may also contain a segment that shares at least 70% sequence identity (typically at least 75%, 80%, 85%, 90%, 95%, 97.5%, or at least 99%, and most commonly at least 99.5%) with any such segment of any of the phylloplanin polypeptides or polynucleotides, where sequence identity is determined by comparing the sequences of the polypeptide or polynucleotide when aligned so as to maximize overlap and identity while minimizing sequence gaps. Preferably the fragments of the phylloplanin polypeptides or polynucleotides of this invention comprise amino acid sequences set forth by amino acids 34-44, 57-84, and 92-123 of SEQ ID NO: 18 and amino acid sequences set forth by amino acids 22-150, 23-150 and 24-150 of SEQ ID NO:18, and the polynucleotide sequences that encode those amino acid sequences, or conservative variants thereof.

The percent identity can be determined by visual inspection and mathematical calculation. The percent identity of two amino acid sequences or two polynucleotide sequences can be determined by comparing sequence information using the GAP computer program, version 6.0 described by Devereux et al. (Nucl. Acids Res. 12:387, 1984) and available from the University of Wisconsin Genetics Computer Group. The default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Polypeptide Sequence and Structure, National Biomedical Research Foundation, pp. 353-358, 1979; (2) a penalty of 3.0 for each gap and an additional 0.10 penalty for each symbol in each gap; and (3) no penalty for end gaps. Other programs used by those skilled in the art of sequence comparison may also be used, such as, for example, the BLASTN program version 2.0.9, available for use via the National Library of Medicine website: www.ncbi.nlm.nih.gov/gorf/wblast2.c-gi, or the UW-BLAST 2.0 algorithm. Standard default parameter settings for UW-BLAST 2.0 are described at the following Internet webpage: blast.wustl.edu/blast/README. html#References. In addition, the BLAST algorithm typically uses the BLOSUM62 amino acid scoring matrix, and optional parameters that may be used are as follows: (A) inclusion of a filter to mask segments of the query sequence that have low compositional complexity (as determined by the SEG program of Wootton & Federhen (Computers and Chemistry, 1993); also see Wootton and Federhen, Methods Enzymol. 266:554-71, 1996) or segments consisting of short-periodicity internal repeats (as determined by the XNU program of Clayerie & States, Computers and Chemistry, 1993), and (B) a statistical significance threshold for reporting matches against database sequences, or E-score (the expected probability of matches being found merely by chance, according to the stochastic model of Karlin and Altschul (1990); if the statistical significance ascribed to a match is greater than this E-score threshold, the match will not be reported); preferred E-score threshold values are 0.5, or in order of increasing preference, 0.25, 0.1, 0.05, 0.01, 0.001, 0.0001, $10^{-5}$, $10^{-10}$, $10^{-15}$, $10^{-20}$, $10^{-25}$, $10^{-30}$, $10^{-40}$, $10^{-50}$, $10^{-75}$, $10^{-100}$.

The invention also provides for soluble forms of phylloplanin polypeptides comprising certain fragments or domains of these polypeptides. Preferably the fragments or domains retain a phylloplanin antimicrobial, preferably antifungal, activity that is at least about 50%, 70%, 80% or 90% of the activity of the phylloplanin providing the fragment or domain. Soluble polypeptides are polypeptides that are capable of being secreted from the cells in which they are expressed. Soluble phylloplanin also include those polypeptides which include part of the transmembrane region, provided that the soluble phylloplanin polypeptide is capable of being secreted from a cell, and typically retains phylloplanin polypeptide activity. Soluble phylloplanin polypeptides further include oligomers or fusion polypeptides comprising at least one phylloplanin polypeptide and fragments of any of these polypeptides that have phylloplanin polypeptide activity. A secreted soluble polypeptide may be identified (and distinguished from its non-soluble membrane-bound counterparts) by separating intact cells which express the desired polypeptide from the culture medium, e.g., by centrifugation, and assaying the medium (supernatant) for the presence of the desired polypeptide. The presence of the desired polypeptide in the medium indicates that the polypeptide was secreted from the cells and thus is a soluble form of the polypeptide. The use of soluble phylloplanin polypeptides are advantageous for many applications. Purification of the polypeptides from recombinant host cells is preferred, because soluble polypeptides are secreted from the cells and are generally more suitable than membrane-bound forms for parenteral administration.

In another aspect, the invention provides polypeptides comprising various combinations of polypeptide domains from different phylloplanin polypeptides. In one embodiment, a fusion construct comprising at least one phylloplanin domain are linked via a peptide linker.

This invention also relates to conservative variants of the phylloplanins described herein, preferably conservative variants of a polypeptide having the amino acid sequence set forth in SEQ ID NO: 18, SEQ ID NO: 38 or the amino acid sequence set forth by residues 22-150, 23-150 or 24-150 of SEQ ID NO: 18. Conservative variants have conservative substitutions, as described below, of one or more amino acids.

Preferably the conservative variants have amino acid lengths that are at least 25% (typically at least 50%, 60%, 70%, and, most commonly at least 80%) of the length of a phylloplanin polypeptide or polynucleotide and have at least 60% sequence identity (typically at least 70%, 75%, 80%, 85%, 90%, 95%, 97.5%, or at least 99%, and, most commonly at least 99.5%) with that phylloplanin polypeptide or polynucleotide. Those of skill in the art appreciate that certain amino acid residues may be substituted for other amino acid residues in a protein structure without appreciable loss of interactive capacity with structures such as, for example, substrate-binding regions. These changes are termed "conservative" in the sense that they preserve the structural and, presumably, required functional qualities of the starting molecule. Conservative amino acid residue substitutions generally are based on the relative similarity of the amino acid residue side-chain substituents, for example, their hydrophobicity, hydrophilicity, charge, size, and the like. An analysis of the size, shape and type of the amino acid residue side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine are defined herein as equivalent to each other; alanine, glycine and serine are defined herein as equivalent to each other; and phenylalanine, tryptophan and tyrosine are defined herein as equivalent to each.

In making such conservative substitutions, the hydropathic index of amino acid residues also may be considered. Each amino acid residue has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, J. Mol. Biol. 157, 105-132 (1982)). It is known that certain amino acid residues may be substituted for other amino acid residues having a similar hydropathic index or score and still retain a similar biological activity. In making changes based upon the hydropathic index, the substitution of amino acid residues whose hydropathic indices are within +/−2 is preferred, those which are within +/−1 are particularly preferred, and those within +/−0.5 are even more particularly preferred.

It also is understood in the art that conservative substitutions of like amino acid residues can be made effectively on the basis of hydrophilicity. U.S. Pat. No. 4,554,101, incorporated herein by reference, states that the greatest local average hydrophilicity of a protein, as governed by the hydrophilicity of its adjacent amino acid residues, correlates with its immunogenicity and antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0+/−1); glutamate (+3.0+/−1); serine (+0.3); asparagine (+0.2); glutamine (+0.2); glycine (0); threonine (−0.4); proline (−0.5+/−1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making conservative variants with substitutions based upon similar hydrophilicity values, the substitution of amino acid residues whose hydrophilicity values are within +/−2 is preferred, those which are within +/−1 are particularly preferred, and those within +/−0.5 are even more particularly preferred.

Additional variants within the scope of the invention include phylloplanin polypeptides that can be modified to create derivatives thereof by forming covalent or aggregative conjugates with other chemical moieties, such as glycosyl groups, lipids, phosphate, acetyl groups and the like. Covalent derivatives can be prepared by linking the chemical moieties to functional groups on amino acid side chains or at the N-terminus or C-terminus of a polypeptide. Conjugates comprising diagnostic (e.g., detectable) or therapeutic agents attached thereto are contemplated herein. Typically, such alteration, substitution, replacement, insertion or deletion retains the desired activity of the polypeptide or a substantial equivalent thereof.

Other derivatives include covalent or aggregative conjugates of the phylloplanin with other polypeptides, such as by synthesis in recombinant culture as N-terminal or C-terminal fusion polypeptides. Examples of fusion polypeptides are discussed herein in connection with oligomers. Further, fusion polypeptides can comprise peptides added to facilitate purification and identification. Such peptides include, for example, poly-His or the antigenic identification peptides described in U.S. Pat. No. 5,011,912 and in Hopp et al., Bio/Technology 6:1204, 1988. One such peptide is the FLAG™ peptide, which is highly antigenic and provides an epitope reversibly bound by a specific monoclonal antibody, by enabling rapid assay and facile purification of the expressed recombinant polypeptide. A murine hybridoma designated 4E11 produces a monoclonal antibody that binds the FLAG™ peptide in the presence of certain divalent metal cations, as described in U.S. Pat. No. 5,011,912. The 4E11 hybridoma cell line is available from the American Type Culture Collection under accession no. HB9259. Monoclonal antibodies that bind the FLAG™ peptide are available from Eastman Kodak Co., Scientific Imaging Systems Division, New Haven, Conn.

As used herein, a "chimeric polypeptide" or "fusion polypeptide" comprises a phylloplanin (including fragments having antimicrobial, preferably anti-fungal activity) polypeptide of the invention operatively linked to a second polypeptide. The second polypeptide can be any polypeptide of interest having an activity or function independent of or related to the function of a phylloplanin polypeptide. For example, the second polypeptide can have a related activity to a phylloplanin polypeptide and can be a domain of a related but distinct member of the phylloplanin family of proteins such as, for example, cytoplasmic or transmembrane domain of a related phylloplanin polypeptide. Within the fusion polypeptide, the term "operatively linked" is intended to indicate that a phylloplanin polypeptide and the second polypeptide are fused in-frame to each other. The second polypeptide can be fused to the N-terminus or C-terminus of a phylloplanin of the invention. Additional examples of polypeptides of interest include peptide linkers, Fc polypeptides, leucine zipper polypeptides, and the like.

Encompassed by the invention are oligomers or fusion polypeptides that contain a phylloplanin polypeptide, one or more fragments of phylloplanin polypeptides, or any of the derivative or variant forms thereof as disclosed herein. In particular embodiments, the oligomers comprise soluble phylloplanin polypeptides. Oligomers can be in the form of covalently linked or non-covalently-linked multimers, including dimers, trimers, or higher oligomers. Leucine zippers and polypeptides derived from antibodies are among the peptides that can promote oligomerization of the polypeptides attached thereto.

Preparation of fusion polypeptides comprising certain heterologous polypeptides fused to various portions of antibody-derived polypeptides (including the Fc domain) has been described (see, e.g., by Ashkenazi et al. PNAS USA 88:10535, 1991; Byrn et al. Nature 344:677, 1990; and Hollenbaugh and Aruffo, "Construction of Immunoglobulin Fusion Polypeptides", in Current Protocols in Immunology, Suppl. 4, pages 10.19.1-10.19.11, 1992).

In another aspect, a fusion polypeptide comprising multiple phylloplanin polypeptides, with or without peptide linkers (spacer peptides) is provided. Among the suitable peptide linkers are those described in U.S. Pat. Nos. 4,751,180 and 4,935,233. In some embodiments, a linker moiety separates the phylloplanin polypeptide domain and the second polypeptide domain in a fusion polypeptide. Such linkers are operatively linked to the C- and the N-terminal amino acids, respectively, of the two polypeptides. Typically a linker will be a peptide linker moiety. The length of the linker moiety is chosen to optimize the biological activity of the soluble phylloplanin and can be determined empirically without undue experimentation. The linker moiety should be long enough and flexible enough to allow a phylloplanin moiety to freely interact with a substrate or ligand. The linker moiety is a peptide between about one and 30 amino acid residues in length, typically between about two and 15 amino acid residues. One linker moiety is a -Gly-Gly- linker. The linker moiety can include flexible spacer amino acid sequences, such as those known in single-chain antibody research. Linking moieties are described, for example, in Huston, J. S., et al., PNAS 85:5879-5883 (1988), Whitlow, M., et al., Protein Engineering 6:989-995 (1993), and Newton, D. L., et al., Biochemistry 35:545-553 (1996). Other suitable peptide linkers are those described in U.S. Pat. Nos. 4,751,180 and 4,935,233, which are hereby incorporated by reference. A DNA sequence encoding a desired peptide linker can be inserted between, and in the same reading frame as, the heterologous sequences (e.g., a phylloplanin encoding nucleic acid) and a second polypeptide encoding nucleic acid, using any suitable conventional technique. For example, a chemically synthesized oligonucleotide encoding the linker can be ligated between the sequences encoding a phylloplanin polypeptide and a second polypeptide of interest. In particular embodiments, a fusion polypeptide comprises from two to four soluble phylloplanin polypeptides separated by peptide linkers.

A polypeptide of the invention may be prepared by culturing transformed and/or recombinant host cells under culture conditions suitable to express the recombinant polypeptide. The resulting expressed polypeptide may then be purified from such culture (i.e., from culture medium or cell extracts) using known purification processes, such as gel filtration and ion exchange chromatography. The purification of the polypeptide may also include an affinity column containing agents which will bind to the polypeptide; one or more column steps over such affinity resins as concanavalin A-agarose, Heparin-toyopearl™, or Cibacrom blue 3GA Sepharose™; one or more steps involving hydrophobic interaction chromatography using such resins as phenyl ether, butyl ether, or propyl ether; or immunoaffinity chromatography. Alternatively, the polypeptide of the invention may be expressed in a form that will facilitate purification. For example, it may be expressed as a fusion polypeptide comprising, for example, maltose binding polypeptide (MBP), glutathione-5-transferase (GST) or thioredoxin (TRX). Kits for expression and purification of such fusion polypeptides are commercially available from New England BioLab (Beverly, Mass.), Pharmacia (Piscataway, N.J.) and InVitrogen, respectively. The polypeptide can also be tagged with an epitope and subsequently purified by using a specific antibody directed to such epitope. One such epitope ("FLAG™") is commercially available from Kodak (New Haven, Conn.). Finally, one or more reverse-phase high performance liquid chromatography (RP-HPLC) steps employing hydrophobic RP-HPLC media, e.g., silica gel having pendant methyl or other aliphatic groups, can be employed to further purify the polypeptide. Some or all of the foregoing purification steps, in various combinations, can be employed to provide a substantially purified homogeneous recombinant polypeptide. A phylloplanin polypeptide thus purified is substantially free of other polypeptides and is defined in accordance with the invention as a "substantially purified polypeptide"; such purified polypeptides of the invention include purified antibodies that bind to a phylloplanin polypeptide, fragment, variant, binding partner and the like. A phylloplanin polypeptide of the invention may also be expressed as a product of transgenic animals or plants, e.g., as a component of the milk of transgenic cows, goats, pigs, or sheep which are characterized by somatic or germ cells containing a polynucleotide encoding the phylloplanin polypeptide of the invention.

It is also possible to utilize an affinity column comprising a polypeptide that binds a phylloplanin polypeptide of the invention, such as a monoclonal antibody generated against a phylloplanin polypeptide, to affinity-purify expressed polypeptides. Polypeptides can be removed from an affinity column using conventional techniques, e.g., in a high salt elution buffer and then dialyzed into a lower salt buffer or by changing pH or other components depending on the affinity matrix utilized, or be competitively removed using the naturally occurring substrate of the affinity moiety, such as a polypeptide derived from the invention. In this aspect of the invention, phylloplanin-binding polypeptides, such as the anti-phylloplanin antibodies of the invention or other polypeptides that can interact with a phylloplanin polypeptide of the invention, can be bound to a solid phase support such as a column chromatography matrix or a similar substrate suitable for identifying, separating, or purifying expressed polypeptides of the invention. Adherence of binding polypeptides (e.g., antibodies) to a solid phase contacting surface can be accomplished by any means; for example, magnetic microspheres can be coated with these binding polypeptides and held in the incubation vessel through a magnetic field.

A phylloplanin polypeptide may also be produced by known conventional chemical synthesis. Methods for constructing polypeptides by synthetic means are known in the art. The synthetically-constructed polypeptide, by virtue of sharing primary, secondary or tertiary structural and/or conformational characteristics with phylloplanin polypeptides, may possess biological properties in common therewith, including antimicrobial activity. Thus, they may be employed as biologically active or immunological substitutes for natural, purified polypeptides in screening assays, the development of antibodies, and in treating microbial infections.

The desired degree of purity depends on the intended use of the polypeptide. A relatively high degree of purity is desired when the polypeptide is to be administered in vivo, for example. In such a case, the polypeptides are purified such that no polypeptide bands corresponding to other polypeptides are detectable upon analysis by SDS-polyacrylamide gel electrophoresis (SDS-PAGE). It will be recognized by one skilled in the art that multiple bands corresponding to the polypeptide can be visualized by SDS-PAGE, due to differential glycosylation, differential post-translational processing, and the like. In one aspect, the polypeptide of the invention is purified to substantial homogeneity, as indicated by a single polypeptide band upon analysis by SDS-PAGE. The polypeptide band can be visualized by silver staining, Coomassie blue staining, or by autoradiography.

Antibodies that are immunoreactive with a phylloplanin polypeptide are provided herein. Such antibodies specifically bind to the polypeptide (e.g., a polypeptide consisting of SEQ ID NO:18 or fragment thereof) via the antigen-binding site of the antibody (as opposed to non-specific binding). In the invention, specifically binding phylloplanin antibodies are those that will specifically recognize and bind with phylloplanin polypeptides, homologues, and variants, but not with other molecules. Similarly, specifically binding anti-phylloplanin antibodies are those that will specifically recognize and bind with phylloplanin polypeptides, homologues, and variants, but not with other molecules. In one embodiment, the antibodies are specific for a phylloplanin polypeptide consisting of SEQ ID NO:18 or fragment thereof, e.g., amino acid residues 22-150, 23-150 or 24-150 of SEQ ID NO:18, and do not cross-react with other polypeptides including related phylloplanin. In this manner, the phylloplanin polypeptides, fragments, variants, fusion polypeptides, and the like, as set forth above can be employed as "immunogens" in producing antibodies immunoreactive therewith.

The antigenic determinants or epitopes of phylloplanins used for immunization can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon polypeptide folding (Janeway et al., Immunobiology 3:9 (Garland Publishing Inc., 2nd ed. 1996)). Because folded polypeptides have complex surfaces, the number of epitopes available is quite numerous; however, due to the conformation of the polypeptide and steric hinderances, the number of antibodies that actually bind to the epitopes is less than the number of available epitopes (Janeway et al., supra). Epitopes can be identified by methods known in the art. Thus, one aspect of the invention relates to the antigenic epitopes of phylloplanin polypeptides. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques known in the art such as solid-phase synthesis, chemical or enzymatic cleavage of a polypeptide, or using recombinant DNA technology.

Antigen-binding antibody fragments that recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the (ab')$_2$ fragments. Alternatively, Fab expression libraries may be constructed (Huse et al., 1989, Science, 246:1275) to allow rapid and easy identification of monoclonal Fab fragments with the desired specificity. Techniques described for the production of single chain antibodies (U.S. Pat. No. 4,946,778; Bird, 1988, Science 242:423; Huston et al., 1988, Proc. Natl. Acad. Sci. USA 85:5879; and Ward et al., 1989, Nature 334:544)

can also be adapted to produce single chain antibodies against phylloplanin gene products. Single chain antibodies are formed by linking the heavy and light chain fragments of the Fv region via an amino acid bridge.

The terms "polynucleotide" as used herein, refers to a polymeric form of nucleotides of at least 10 bases in length (smaller nucleotide sequences are typically referred to as oligonucleotides). The nucleotides can be ribonucleotides, deoxyribonucleotides, or modified forms of either type of nucleotide. The term includes single and double stranded forms of DNA or RNA. DNA includes, for example, cDNA, genomic DNA, chemically synthesized DNA, DNA amplified by PCR, and combinations thereof. The polynucleotides of the invention include full-length genes or cDNA molecules as well as a combination of fragments thereof.

By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant polynucleotide molecule, which is incorporated into a vector, e.g., an expression vector; into an autonomously replicating plasmid or virus; or into the genomic DNA of a prokaryote or eukaryote, or which exists as a separate molecule (e.g., a cDNA) independent of other sequences.

A phylloplanin polynucleotide of the invention comprises: (a) a polynucleotide that encodes a polypeptide comprising a sequence set forth in SEQ ID NO:18 from amino acid 1 to amino acid 150; (b) a polynucleotide encoding a polypeptide comprising a sequence as set forth in SEQ ID NO:18 from amino acid residue $X_1$ to amino acid residue 150, wherein $X_1$ is an amino acid between and including residues 22, 23 and 24 (amino acid sequences comprising amino acids 22-150, 23-150, or 24-150); (c) a sequence as set forth in SEQ ID NO:17 from nucleotide residue 1 to nucleotide residue 666, or a fragment thereof; (d) sequences complementary to a sequence as set forth in SEQ ID NO:17; (e) fragments of SEQ ID NO:17 from nucleotide residue $X_1$ to 666, wherein $X_1$ is a nucleotide residue between and including residues 66-72 (residues 66-666, 67-666, 68-666, 69-666, 70-666, 71-666 or 72-666), or their complements that specifically hybridize to the polynucleotide consisting of SEQ ID NO:17, under moderate to highly stringent conditions; and any of the foregoing wherein T can also be U (e.g., RNA sequences). Also encompassed by the invention are homologues of a phylloplanin polynucleotide of the invention. Polynucleotide homologues can be identified in several ways, including isolation of genomic or cDNA molecules from a suitable source, or computer searches of available DNA sequence databases.

Polynucleotides encoding a polypeptide of this invention, or fragment thereof, e.g., the nucleotide sequence set forth by SEQ ID NO: 17 or the nucleotides of SEQ ID NO: 17 that encode the amino acid sequences set forth by amino acid sequences set forth by amino acids 34-44, 57-84, and 92-123 of SEQ ID NO: 18, amino acids 45-51, 85-91, 124-132 or 144-150 of SEQ ID NO:18, or the complementary nucleotide sequence, can be used as probes or primers for the isolation of nucleic acids or as query sequences for database searches. Such probes or primers can be obtained by "back-translation" from the amino acid sequences, or by identification of regions of amino acid identity with polypeptides for which the coding DNA sequence has been identified. The polymerase chain reaction (PCR) procedure can be employed to isolate and amplify a polynucleotide encoding a phylloplanin polypeptide or a desired combination of phylloplanin polypeptide fragments. Oligonucleotides that define the desired termini of a combination of DNA fragments are employed as 5' and 3' primers. The oligonucleotides can additionally contain recognition sites for restriction endonucleases to facilitate insertion of the amplified DNA fragments into an expression vector. PCR techniques are described in Saiki et al., Science 239:487 (1988); Recombinant DNA Methodology, Wu et al., eds., Academic Press, Inc., San Diego (1989), pp. 189-196; and PCR Protocols: A Guide to Methods and Applications, Innis et. al., eds., Academic Press, Inc. (1990). The primer and probe sequences are presented in SEQ ID NOS:1-16 and 32-35.

Among the uses of the disclosed phylloplanin polynucleotides, and combinations of fragments thereof, is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence. The basic parameters affecting the choice of hybridization conditions and guidance for devising suitable conditions are set forth by Sambrook et al., (1989, Molecular Cloning: A Laboratory Manual, Cold Spring Harbor Laboratory Press, Cold Spring Harbor, N.Y., chapters 9 and 11) and are described herein. Using knowledge of the genetic code in combination with the amino acid sequences set forth above, sets of degenerate oligonucleotides can be prepared. Such oligonucleotides are useful as primers, e.g., in polymerase chain reactions (PCR). In certain embodiments, degenerate primers can be used as probes for non-human genetic libraries. Such libraries include, but are not limited to, cDNA libraries, genomic libraries, and even electronic EST (express sequence tag) or DNA libraries. Homologous sequences identified by this method would then be used as probes to identify phylloplanin homologues.

The invention also includes polynucleotides that hybridize under moderately stringent conditions or highly stringent conditions, to polynucleotides encoding phylloplanin polypeptides described herein. The basic parameters affecting the choice of hybridization conditions and guidance for devising suitable conditions are set forth by Sambrook et al.; 1989 and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA. One way of achieving moderately stringent conditions involves the use of a prewashing solution containing 5×SSC, 0.5% SDS, 1.0 mM EDTA (pH 8.0) at a temperature of about room temperature, and a hybridization buffer of about 50% formamide, 6×SSC, and a hybridization temperature of about 55° C. (or other similar hybridization solutions, such as one containing about 50% formamide, with a hybridization temperature of about 42° C.), and washing conditions of about 60° C., in 0.5×SSC, 0.1% SDS. Generally, highly stringent conditions are defined as hybridization conditions as above, but with washing at approximately 68° C., 0.2×SSC, 0.1% SDS. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete. The wash temperature and wash salt concentration can be adjusted as necessary to achieve a desired degree of stringency by applying the basic principles that govern hybridization reactions and duplex stability, as known to those skilled in the art and described further below (see, e.g., Sambrook et al. 1989). When hybridizing a nucleic acid to a target nucleic acid of unknown sequence, the hybrid length is assumed to be that of the hybridizing nucleic acid. When nucleic acid of known sequences are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 10° C. less than the melting temperature ($T_m$) of the hybrid, where $T_m$ is determined according to the following equations. For hybrids less than 18 base pairs in length, $T_m$ (° C.)=2(# of A+T bases)+4(# of G+C bases). For hybrids above 18 base pairs in length, T° C.)=81.5+16.6(log [Na$^+$])+0.41(% G+C)−(600/N), where N is the number of bases in the hybrid, and [Na$^+$] is the concentration of sodium ions in the hybridization buffer ([Na$^+$] for 1×SSC=0.165M). Each such hybridizing nucleic acid molecule has a length that is at least 15 nucleotides (or typically at least 18 to about 20 nucleotides, or at least 25 to about 30 nucleotides, or at least 40 nucleotides, or more commonly at least 50 nucleotides), or at least 25% (e.g., at least 50%, or at least 60%, or at least 70%, and most typically at least 80%) of the length of a polynucleotide of the invention to which it hybridizes, and has at least 60% sequence identity (e.g., at least 70% to about 75%, at least 80% to about 85%, at least 90% to about 95%, at least 97.5%, or at least 99%, and most commonly at least 99.5%) with a polynucleotide of the invention to which it hybridizes, where sequence identity is determined by comparing the sequences of the hybridizing nucleic acids when aligned so as to maximize overlap and identity while minimizing sequence gaps as described above.

The invention also provides genes corresponding to the polynucleotides disclosed herein. "Corresponding genes" are the regions of the genome that are transcribed to produce the mRNAs from which cDNA molecules are derived and may include contiguous regions of the genome necessary for the regulated expression of such genes. Corresponding genes may therefore include but are not limited to coding sequences, 5' and 3' untranslated regions, alternatively spliced exons, introns, promoters, enhancers, and silencer or suppressor elements. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. An "isolated gene" is a gene that has been separated from the adjacent coding sequences, if any, present in the genome of the organism from which the gene was isolated and includes both coding and non-coding regions.

Methods for making phylloplanin polypeptides are described below. Expression, isolation, and purification of the polypeptides and fragments of the invention can be accomplished by any suitable technique, including but not limited to the following methods.

An isolated polynucleotide of the invention may be operably linked to an expression control sequence such as, e.g., the pDC412 or pDC314 vectors (Microbix Biosystems Inc., Toronto, Canada), pMal-cVx (BioRad), or the pMT2 or pED expression vectors disclosed in Kaufman et al., Nucleic Acids Res. 19:4485-4490 (1991); and Pouwels et al. Cloning Vectors: A Laboratory Manual, Elsevier, N.Y., (1985), in order to produce a phylloplanin polypeptide recombinantly. Many suitable expression control sequences are known in the art. General methods of expressing recombinant polypeptides are also known and are exemplified in R. Kaufman, Methods in Enzymology 185, 537-566 (1990). As used herein "operably linked" means that a polynucleotide of the invention and an expression control sequence are situated within a construct, vector, or cell in such a way that the polypeptide encoded by a polynucleotide is expressed when appropriate molecules (such as polymerases) are present. In one embodiment, at least one expression control sequence is operably linked to a phylloplanin polynucleotide of the invention in a recombinant host cell or progeny thereof, the polynucleotide and/or expression control sequence having been introduced into the host cell by transformation or transfection, for example, or by any other suitable method. In another embodiment, at least one expression control sequence is integrated into the genome of a recombinant host cell such that it is operably linked to a polynucleotide encoding a phylloplanin polypeptide. In one embodiment of the invention, at least one expression control sequence is operably linked to a polynucleotide of the invention through the action of a trans-acting factor such as a transcription factor, either in vitro or in a recombinant host cell.

In addition, a polynucleotide encoding an appropriate signal peptide (native or heterologous) can be incorporated into expression vectors. The choice of signal sequence can depend on factors such as the type of host cells in which the recombinant polypeptide is to be produced. A DNA sequence for a signal sequence (secretory leader) can be fused in frame to a polynucleotide of the invention so that the DNA is initially transcribed, and the mRNA translated, into a fusion polypeptide comprising the signal peptide. A signal peptide that is functional in the intended host cells promotes secretion of the polypeptide. The signal peptide is cleaved from the polypeptide upon secretion of polypeptide from the cell. The skilled artisan will also recognize that the position(s) at which the signal peptide is cleaved can differ from that predicted by computer program, and can vary according to such factors as the type of host cells employed in expressing a recombinant polypeptide. A polypeptide preparation can include a mixture of polypeptide molecules having different N-terminal amino acids, resulting from cleavage of the signal peptide at more than one site. A phylloplanin polypeptide of the invention may comprise a signal peptide from amino acid 1-23. This can be substituted by heterogenous signal peptides using known recombinant DNA techniques.

Established methods for introducing DNA into cells have been described (Kaufman, Large Scale Mammalian Cell Culture, 1990, pp. 15-69). Additional protocols using commercially available reagents, such as Lipofectamine lipid reagent (Gibco/BRL) or Lipofectamine-Plus lipid reagent, can be used to transfect cells (Felgner et al., Proc. Natl. Acad. Sci. USA 84:7413-7417, 1987). Selection of stable transformants can be performed using methods known in the art such as, for example, resistance to cytotoxic drugs. Kaufman et al., Meth. in Enzymology 185:487-511, 1990, describes several selection schemes, such as dihydrofolate reductase (DHFR) resistance. A suitable strain for DH selection can be CHO strain DX-B11, which is deficient in DHFR (Urlaub et al., Proc. Natl. Acad. Sci. USA 77:4216-4220, 1980). A plasmid expressing the DHFR cDNA can be introduced into strain DX-B11, and only cells that contain the plasmid can grow in the appropriate selective media. Examples of selectable markers that can be incorporated into expression vectors include cDNAs conferring resistance to antibiotics, such as G418 and hygromycin B. Cells having the vector can be selected based on resistance to such compounds.

Alternatively, gene products can be obtained via homologous recombination, or "gene targeting" techniques. Such techniques employ the introduction of exogenous transcription control elements (such as the CMV promoter or the like) in a particular predetermined site on the genome, to induce expression of an endogenous phylloplanin of the invention.

The location of integration into a host chromosome or genome can be determined by one of skill in the art, given the known location and sequence of the gene. In one embodiment, the invention contemplates the introduction of exogenous transcriptional control elements in conjunction with an amplifiable gene, to produce increased amounts of the gene product. The practice of homologous recombination or gene targeting is explained by Chappel in U.S. Pat. No. 5,272,071 (see also Schimke, et al. "Amplification of Genes in Somatic Mammalian cells," Methods in Enzymology 151:85 (1987), and by Capecchi, et al., "The New Mouse Genetics: Altering the Genome by Gene Targeting," TIG 5:70 (1989)).

A number of cell types may act as suitable host cells for expression of a polypeptide of the invention. It may be possible to produce the polypeptide in lower eukaryotes such as yeast or in prokaryotes such as bacteria, and in plant cells. Potentially suitable yeast strains include *Saccharomyces cerevisiae, Schizosaccharomyces pombe, Kluyveromyces strains, Candida*, or any yeast strain capable of expressing heterologous polypeptides. Potentially suitable bacterial strains include *Escherichia coli, Bacillus subtilis, Salmonella typhimurium*, or any bacterial strain capable of expressing heterologous polypeptides. If the polypeptide is made in yeast or bacteria, it may be necessary to modify the polypeptide produced therein, for example by phosphorylation or glycosylation of the appropriate sites, in order to obtain the functional polypeptide. Such covalent attachments may be accomplished using known chemical or enzymatic methods. The polypeptides may also be produced by operably linking an isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac™ kit), or as described in Summers and Smith, Texas Agricultural Experiment Station Bulletin No. 1555 (1987), and Luckow and Summers, Bio/Technology 6:47 (1988). As used herein, a host cell capable of expressing a polynucleotide of the invention is "transformed." Cell-free translation systems could also be employed to produce polypeptides using RNAs derived from polynucleotide constructs disclosed herein. A host cell that comprises an isolated polynucleotide of the invention, typically operably linked to at least one expression control sequence, is a "recombinant host cell".

The polynucleotides encoding the phylloplanin polypeptides of the invention can be used for numerous diagnostic or other useful purposes. The polynucleotides of the invention can be used to express recombinant polypeptides for analysis, characterization or therapeutic uses; as markers for tissues in which the corresponding polypeptide is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in subjects to identify potential genetic disorders; as probes to hybridize and thus discover novel, related nucleic acid molecules; as a source of information to derive PCR primers for genetic fingerprinting; as a probe to "subtract-out" known sequences in the process of discovering other novel nucleic acids; for selecting and making oligomers for attachment to a "gene chip" or other support, including for examination of expression patterns; to raise anti-polypeptide antibodies using DNA immunization techniques; as an antigen to raise anti-DNA antibodies or elicit another immune response, and for gene therapy. Any or all polynucleotides suitable for these uses are capable of being developed into reagent grade or kit format for commercialization as products. For example, a kit of the invention will include one or more containers being compartmentalized and designed to hold primers and/or probes (e.g., SEQ ID NOs:1-16 and 32-35 to amplify phylloplanin), antibodies, polypeptides and related reagents (e.g., Taq polymerase and the like). Methods for performing these uses are known in the art. References disclosing such methods include, without limitation, "Molecular Cloning: A Laboratory Manual", 2d ed., Cold Spring Harbor Laboratory Press, Sambrook et al. eds., 1989, and "Methods in Enzymology: Guide to Molecular Cloning Techniques", Academic Press, Berger and Kimmel eds., 1987. The phylloplanin polypeptides can be employed in inhibiting microbial infections preferentially fungal infections in vitro or in vivo.

The polynucleotides encoding phylloplanin polypeptides, and the disclosed fragments and combinations of these polynucleotides can be used by one skilled in the art using known techniques to analyze abnormalities associated with the genes corresponding to these molecules. This enables one to distinguish conditions in which this marker is rearranged or deleted. In addition, polynucleotides of the invention or a fragment thereof can be used as a positional marker to map other genes of unknown location. The DNA can be used in developing treatments for any disorder mediated (directly or indirectly) by defective, or insufficient amounts of, the genes corresponding to the polynucleotides of the invention. The polynucleotides disclosed herein permit the detection of defective genes, and the replacement thereof with normal genes. Defective genes can be detected in in vitro diagnostic assays, and by comparison of a native nucleotide sequence disclosed herein with that of a gene derived from a person suspected of harboring a defect in this gene.

The phylloplanin polypeptides, fragments (including soluble fragments), variants, antibodies, and binding partners of the invention are useful to improve the disease-resistance or disease-tolerance of plants either during the life of the plant or for post-harvest crop protection. Such polypeptides are also useful for inhibiting germination, growth and proliferation of pathogens e.g., fungi and fungi-like organisms, Pathogens exposed to such polypeptides are growth-inhibited. The antifungal properties of a phylloplanin can eradicate a pathogen already established on the plant or may protect the plant from future pathogen attack. The eradicant effect of the phylloplanin polypeptides and fragments is particularly advantageous.

The phylloplanins of this invention, e.g., phylloplanins from tobacco, e.g., *Nicotiana tabacum*, sunflower e.g., *Helianthus annus*, and *Datura*, e.g. *Datura metel*, and compositions comprising the phylloplanins, e.g., LWWs of tobacco, sunflower, and *Datura*, can be used in methods to inhibit microbial growth and treat diseases, preferably diseases of plants caused by infection with a pathogenic fungus or fungus-like organisms, e.g.: an oomycetes, e.g. *P. tabacina*; a basidiomycete, such as e.g., *R. solani*, which causes Brown Patch in annual rye grass (*Lolium multiflorum*), perennial rye grass (*Lolium perenne*), and creeping bentgrass (*Agrostis palustris*), Target Spot in tobacco, and *Rhizctonia* seedling blight in sunflower, and; diseases caused by the ascomycete fungus *P. grisea*, which causes Grey Leaf Spot in annual and perennial rye grasses. Preferably the plants susceptible to disease caused by infection with the fungus or fungus-like organism are crop plants, e.g., corn, soybean, tobacco, tomato, potato, pepper, *Datura*, alfalfa, cucumber,

*vitis* sp and *medicago*, or grasses, e.g. turfgrasses, such as, e.g., annual and perennial rye grasses, and creeping bentgrass.

Exposure of a pathogen, e.g., a fungus, fungal like organism, to a phylloplanin polypeptide can be achieved in various ways, for example: (a) The isolated phylloplanin polypeptide may be applied to plant parts or to the soil or other growth medium surrounding the roots of the plants or to the seed of the plant before it is sown using standard agricultural techniques (such as, e.g., spraying). The phylloplanin polypeptide may have been isolated from plant tissue or chemically synthesized or extracted from micro-organisms genetically modified to express the peptide. The phylloplanin polypeptide may be applied to plants or to the plant growth medium in the form of a composition comprising the phylloplanin polypeptide in admixture with a solid or liquid diluent and optionally various adjuvants such as surface-active agents. Solid compositions may be in the form of dispersible powders, granules, or grains. (b) A composition comprising a micro-organism genetically modified to express a phylloplanin polypeptide may be applied to a plant or the soil in which a plant grows. (c) An endophyte genetically modified to express the phylloplanin polypeptide may be introduced into the plant tissue (for example, via a seed treatment process). An endophyte is defined as a micro-organism having the ability to enter into non-pathogenic endosymbiotic relationships with a plant host. A method of endophyte-enhanced protection of plants has been described in a series of patent applications by Crop Genetics International Corporation (for example, International Application Publication Number WO90/13224, European Patent Publication Number EP-125468-B1, International Application Publication Number WO91/10363, International Application Publication Number WO87/03303). The endophyte may be genetically modified to produce agricultural chemicals. International Patent Application Publication Number WO94/16076 (ZENECA Limited) describes the use of endophytes which have been genetically modified to express a plant-derived antifungal peptide. (d) DNA encoding a phylloplanin polypeptide may be introduced into the plant genome so that the polypeptide is expressed within the plant body (the DNA may be cDNA, genomic DNA or DNA manufactured using a standard nucleic acid synthesizer).

In practicing a method of treatment or use of the invention, a therapeutically effective amount of a therapeutic agent of the invention is contacted with a plant, subject or surface to inhibit, treat or ameliorate a microbial (e.g., a fungal) infection. "Therapeutic agent" includes without limitation any of the phylloplanin polypeptides, fragments, and variants; soluble forms of the phylloplanin polypeptides; antibodies to a phylloplanin polypeptide or fragment; phylloplanin polypeptide binding partners; complexes formed from the phylloplanin polypeptides, fragments, variants, and binding partners, and the like. As used herein, the term "effective amount" or "therapeutically effective amount" means the total amount of each polypeptide or therapeutic agent or other active component of the pharmaceutical composition or method that is sufficient to show a meaningful benefit, e.g., treatment, healing, inhibition, prevention or amelioration of microbial contamination or infection, or an increase in rate of treatment, healing, inhibition, prevention or amelioration of such contamination and infections. Preferably the meaningful benefit is a statistically significant as compared to a control. Contacting a subject, organism or surface with the phylloplanin polypeptides can be done in vitro or in vivo with an amount and for a time sufficient to reduce microbial infection or presence.

Compositions comprising a therapeutically effective amount of a phylloplanin polypeptide, or variant, conservative variant, fragment, or oligomer thereof, (from whatever source derived, e.g., recombinant and non-recombinant sources), in combination with other components such as a physiologically acceptable diluent, carrier, or excipient, are provided herein and can be used in the methods described herein. The term "pharmaceutically acceptable" means a non-toxic material that does not interfere with the effectiveness of the biological activity of the active ingredient(s).

An aspect of the invention is a phylloplanin-containing composition prepared by rinsing the surfaces of a plant, with an aqueous solution, and collecting the rinses forming "a leaf water wash" ("LWW"). The LWW may be concentrated and thus enriched for phylloplanins. The rinses may be concentrated by e.g. lyophilizing the rinses and then resuspending the lyophilate in an aqueous solution, or by filtration. Preferably the surface of the plant is a leaf surface and preferably the plant is a broad leaf plant, more preferably a *Nicotiana* sp, a *Helianthus* sp, or a *Datura* sp, most preferably a *Nicotiana tabacum*, a *Helianthus annus* or a *Datua metel*. Preferably the polypeptides of the LWW consist essentially of phylloplanins.

In one aspect of the invention the phylloplanin-containing composition comprises phylloplanins that are basic and hydrophobic having a molecular weight of about 10 kD to about 75 kD, preferably about 10 kD to about 30 kD. The composition may be an aqueous composition, e.g. a leaf water wash (LWW) comprising e.g., at least about 12.5 ng/μl, 25 ng/μl, or 50 ng/μl total proteins. Preferably the proteins of the LWW consist essentially of phylloplanins.

A phylloplanin polypeptide of the invention (including fragments) may be active in multimers (e.g., heterodimers or homodimers) or complexes with itself or other polypeptides. As a result, pharmaceutical compositions of the invention may comprise a polypeptide of the invention in such multimeric or complexed form. Such compositions contemplate the preparation of fragments of phylloplanin in any combination thereof as oligomers.

The invention further relates to gene promoter sequences isolated from a plant and their use to regulate chimeric gene expression in plants. In particular, the invention describes the isolation and use of DNA sequences which permit a high level of expression of foreign genes in transgenic plants.

The expression of genes in plants is controlled by a number of regulatory components, including nucleic acid and protein elements. Where the plant gene exists as double stranded DNA, the primary steps of expression involve the production of a messenger RNA by a polymerase enzyme. The initiation of this part of the expression process is controlled by a region commonly referred to as the "promoter". The promoter lies upstream (5') of the protein encoding region and may be constitutive or tissue-specific, developmentally-regulated and/or inducible.

Manipulation of plants, e.g. crop plants and grasses, to alter and/or improve phenotypic characteristics (such as productivity, quality, pathogen resistance) uses the expression of heterologous genes in plant tissues. Such genetic manipulation therefore relies on the availability of means to drive and to control gene expression as required; for example, on the availability and use of suitable promoters which are effective in plants and which regulate gene expression so as to give the desired effect(s) in the transgenic plant. It is advantageous to have the choice of a variety of different promoters so that the most suitable promoter may be selected for a particular gene, construct, cell, tissue, plant or environment.

Promoters (and other regulatory components) from bacteria, viruses, fungi and plants have been used to control gene expression in plant cells. Numerous plant transformation experiments using DNA constructs comprising various promoter sequences fused to various foreign genes (for example, bacterial marker genes) have led to the identification of useful promoter sequences. It has been demonstrated that sequences up to 500-1000 bases in most instances are sufficient to allow for the regulated expression of foreign genes. However, it has also been shown that sequences much longer than 1 kb may have useful features which permit high levels of gene expression in transgenic plants. A range of naturally-occurring promoters are known to be operative in plants and have been used to drive the expression of heterologous (both foreign and endogenous) genes in plants: for example, the constitutive 35S cauliflower mosaic virus promoter, the ripening-enhanced tomato polygalacturonase promoter (Bird et al, 1988, Plant Molecular Biology, 11:651-662), the E8 promoter (Diekman & Fischer, 1988, EMBO, 7:3315-3320) and the fruit specific 2A11 promoter (Pear et al, 1989, Plant Molecular Biology, 13:639-651) and many others.

As stated above, successful genetic manipulation relies on the availability of means to control plant gene expression as required. A scientist uses a suitable expression cassette (incorporating one or more promoters and other components) to regulate gene expression in the desired manner (for example, by enhancing or reducing expression in certain tissues or at certain developmental stages). The ability to choose a suitable promoter from a range of promoters having differing activity profiles is thus important.

In the invention, a phylloplanin gene promoter has been isolated and fully sequenced from the surface of plant leaves. The phylloplanin promoter essentially controls the production of the protein known as "phylloplanin" in plants. This phylloplanin protein is associated with the plant epidermal layer.

According to the invention, there is provided a polynucleotide phylloplanin promoter capable of driving gene expression in plants. Such polynucleotide may contain a segment that shares at least 70% sequence identity (typically at least 75%, 80%, 85%, 90%, 95%, 97.5%, or at least 99%, and most commonly at least 99.5%) with any such segment of any of the polynucleotide phylloplanin promoter sequence, where sequence identity is determined by comparing the sequences of the polynucleotide when aligned so as to maximize overlap and identity while minimizing sequence gaps. An example of a polynucleotide promoter of the invention includes the sequence as set forth in SEQ ID NO:34.

"Active variants" are DNA sequences partially homologous to SEQ ID NO:34 that retain promoter activity. It may be possible to alter the level or type of activity of these promoters by manipulating their sequences: for example, by altering the nucleotide sequence in key regulatory regions, by truncating the sequence or by deleting parts within the sequence.

The promoter of the invention is suitable for incorporation into polynucleotide constructs encoding any target gene or transcribable polynucleotide region so that the target gene or polynucleotide is expressed when the construct is transformed into a plant. The construct will typically contain a transcription termination signal.

The phylloplanin promoter may be synthesized ab initio using the sequence shown in SEQ ID NO:34 as a guide. Alternatively, the promoters may be isolated from plant genomic libraries using suitable probes derived from the sequences or the promoter may be isolated using a PCR approach.

In practice the promoter of the invention may be inserted as a promoter in a recombinant polynucleotide construct designed for use in a plant. The construct is then inserted into the plant by transformation. Any plant species may be transformed with the construct, and any suitable transformation method may be employed.

In another embodiment, the fusion construct comprises (a) a polynucleotide comprising a sequence that is at least 80% identity (typically at least 90%, 95%, or at least 98%) with SEQ ID NO:34; and (b) a polynucleotide comprising a coding region of a polypeptide of interest, wherein the polynucleotide of (a) is operably linked to the polynucleotide of (b).

In yet another aspect, the invention provides methods for producing a transgenic plant which expresses a nucleic acid segment encoding the phylloplanin protein of the invention. The process of producing transgenic plants is well-known in the art. In general, the method comprises transforming a suitable host cell, e.g., a corn, soybean, tobacco, tomato, potato, pepper, *Datura*, alfalfa, cucumber, *medicago* or grass, e.g., turfgrass, cell, with a DNA segment which contains a promoter operatively linked to a coding region that encodes a phylloplanin protein. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant phylloplanin protein expressed in a particular transgenic cell, the invention also provides for the expression of phylloplanin protein antisense mRNA. The use of antisense mRNA as a means of controlling or decreasing the amount of a given protein of interest in a cell is well-known in the art.

The invention further provides a transgenic plant, seed, cell, e.g., corn, soybean, tobacco, tomato, potato, pepper, *Datura*, alfalfa, cucumber, *vitis* sp, *medicago* or grass, e.g., turfgrass, plant, seed, cell, or any other form of regenerant, comprising a heterologous polynucleotide (>80% homology, commonly >90% homology, more typically >95% homology) selected from the group consisting of a) a polynucleotide comprising SEQ ID NO:17; b) a polynucleotide comprising a sequence selected from the group consisting of: from about nucleotide $X_1$ to 666 of SEQ ID NO:17 wherein $X_1$ is a nucleotide between residues 66-72; c) a polynucleotide that hybridizes under moderate to highly stringent conditions to a polynucleotide comprising the sequence of SEQ ID NO:17 and encoding a polypeptide that is a disease- or pest-resistant conferring protein; d) a nucleotide sequence complementary to a sequence of SEQ ID NO:17; and e) any of the nucleotide sequences of a) to d) wherein T can also be U.

In yet another aspect, the invention provides a transgenic plant, e.g., a transgenic corn, soybean, tobacco, tomato, potato, pepper, *Datura*, alfalfa, cucumber, *vitis* sp, *medicago* or grass, e.g. turfgrass such as e.g. annual rye grass (*Lolium multiflorum*), perennial rye grass (*Lolium perenne*), and creeping bentgrass (*Agrostis palustris*), comprising a heterologous promoter of a fusion construct comprising (a) a polynucleotide comprising a sequence that is at least 80% identical to SEQ ID NO:34; and (b) a polynucleotide comprising a coding region of a polypeptide of interest, wherein the polynucleotide of (a) is operably linked to the polynucleotide of (b).

EXAMPLES

SDS-PAGE analyses of LWW from greenhouse-grown TI 1068 leaves indicated the presence of four bands with molecular masses of 16 (I), 19 (II), 21 (III), and 25 (IV) kDa (FIG. 1B, lane d), which are collectively termed phylloplanins. Phylloplanins in LWW were relatively pure and abundant, compared to proteins present in leaf epidermal cells (FIG. 1B, lane b) or leaf extracellular fluid (FIG. 1B, lane c), suggesting selective deployment on the phylloplane. Sterile-grown TI 1068 LWW contained phylloplanins (FIG. 1B, lane e), indicating that these proteins were not from leaf surface microbes and were not induced by pathogen attack. From measurement of the protein concentration in LWW (BCA assay), it was estimated that the phylloplane of greenhouse-grown TI 1068 leaves contains 100-200 ng protein/square-cm leaf surface. Field-grown TI 1068 LWW also contained phylloplanins, indicating that leaf surface proteins are present under natural conditions (FIG. 1C, lane a), and phylloplanins were renewed after washing. *N. tabacum* cultivars TI 1112 and TI 1406 that lack TGSTs, or secretion, respectively, produce substantial phylloplanins, so diterpene/sugar ester producing TGSTs are not the site of phylloplanin biosynthesis. Field-grown soybean and sunflower LWWs contained varying amounts of proteins (FIG. 1C, lanes c-d), as did greenhouse-grown corn, tomato, soybean, and potato, but these proteins were not further characterized.

T-Phylloplanins Inhibit *P. tabacina* Spore Germination and Leaf Infection

*P. tabacina* is an oomycete pathogen that reproduces via airborne spores (Lucas, G. B. 1975), and initial host contact and spore deposition commences at the phylloplane (Svircev, A. M et al. (1989) Host-parasite relations: morphology and ultrastructure. In W E McKeen, ed, Blue Mold of Tobacco. APS Press, St. Paul, pp 43-104). LWW from greenhouse-grown TI 1068 plants inhibited *P. tabacina* spore germination (FIG. 2A, b; $LD_{50}$ about 15-20 ng/µl (50 spores/µl)), as did LWW from sterile-grown plants. Protein digestion by immobilized Proteinase K relieved inhibition of spore germination (FIG. 2A,c), indicating that proteins were necessary for inhibition. Spore germination was not affected by water, incubated with immobilized Proteinase K. Once spore germination was initiated, addition of LWW (100 ng/µl total protein) immediately arrested germination tube growth and development. Using GC, the levels of residual exudate diterpenes found in LWW were <1/10 of the $LD_{50}$ reported to inhibit *P. tabacina* germination (Kennedy, B. S. et al. 1992 J. Chem. Ecol. 18:1467-1479), and nicotine was not detected.

Figure 2:
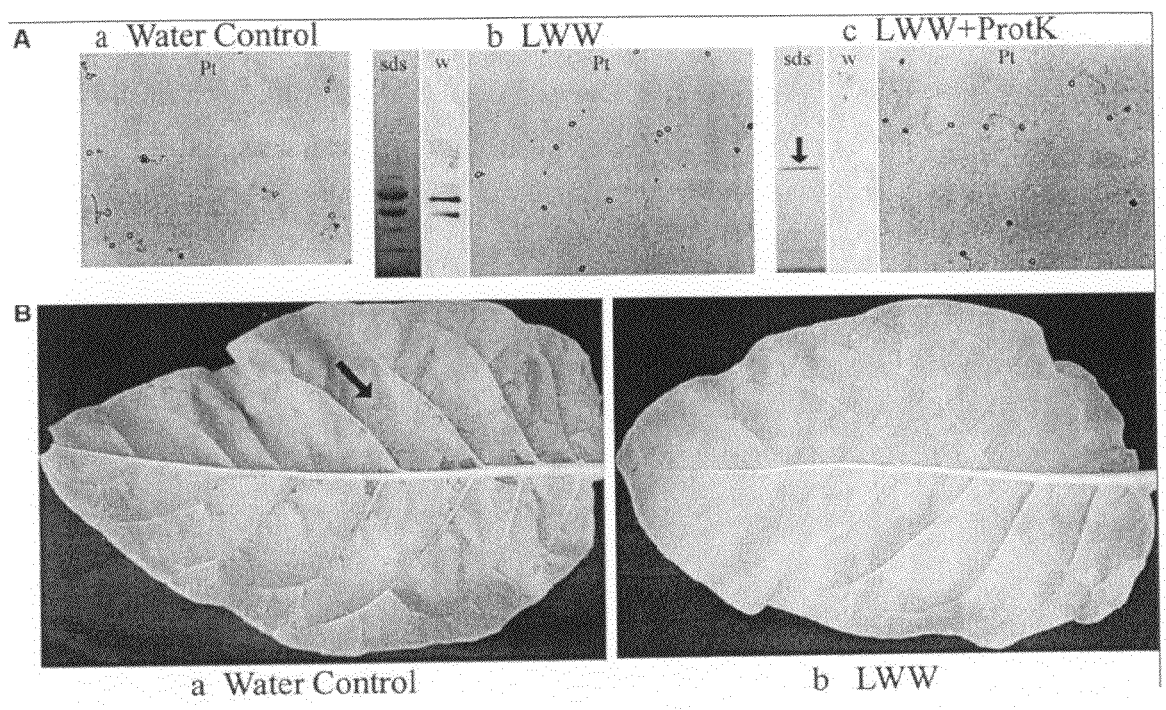
FIG. 2A-B depicts proteins in TI 1068 LWW that inhibit *P. tabacina* spore germination and leaf infection. A: *P. tabacina* spore germination assays (Pt), Coomassie-stained SDS-PAGE (sds), and western blots with 1:10,000 phylloplanin antiserum (w). a, water+spores. b, TI 1068 LWW (diluted to 100 ng/µl total protein)+spores. c, TI 1068 LWW (100 ng/µl total protein) digested with Proteinase K (ProtK)+spores.

Intact *N. tabacum* Petite Havana SR1 plants, considered susceptible to *P. tabacina*, were infected by applying spores (50 spores/µl in 4 µl water) to the leaf surface. After 5 days, sporulating lesions developed at sites of application (FIG. 2B,a). Phylloplanins in TI 1068 LWW, when mixed with spores at total protein concentrations of 50 ng/µl or higher, inhibited leaf infection by *P. tabacina* (FIG. 2B,b). At 25 ng/µl total protein, about 75% inhibition was observed, and no inhibition occurred with titrations below 12.5 ng/µ total protein. Similar results were observed in three independent experiments and in identical experiments using the susceptible cultivar KY 14. Like TI 1068, LWWs of Petite Havana and KY 14 contain a similar phylloplanin pattern, but unlike TI 1068, they produce much less trichome exudate. Other surface chemicals (e.g., surface lipids or trichome exudate components) may influence or accentuate phylloplanin activity, dispersion, or longevity, by acting as adducts or as solubilizing agents. Although it is difficult to estimate the role of a single component, such as the presence of phylloplanins, in blue mold susceptibility or resistance, outside the experimental conditions used here, phylloplanins appear to be a key component.

Isolation of the Novel T-Phylloplanin Gene

*N. tabacum* phylloplanins I, II, III, and IV share an identical N-terminal amino acid sequence (Table 1). Internal amino acid sequences were elucidated from peptides generated by trypsin digestion of Phylloplanins II and IV, and pepsin digestion of total LWW (Table 1). Degenerate, deoxyinosine-containing primers were synthesized and used in RT-PCR with cDNA generated from *N. tabacum* total leaf RNA as a template, and a 332 bp fragment was amplified. RLM-RACE was used to recover a full-length, *N. tabacum* Phylloplanin cDNA sequence (FIG. 3; Accession No. Genbank AY705384 (SEQ ID NO:17)) of 666 bp in length, encoding a hydrophobic, basic (50% hydrophobicity, estimated pI 9.3, Vector NTI) 15.4 kDa protein containing 150 amino acids (SEQ ID NO:18). Based on the N-terminus recovered from the mature phylloplanin (Ile-24) the first 23 amino acids comprise a signal sequence that targets the protein to the secretory pathway (Targetp version 1.0 (Emanuelsson, O. et al. 2000) J. Mol. Biol. 300:1005-1016). The molecular mass of the mature protein is estimated to be about 13 kDa. The protein of this mass from the leaf surface is not recovered, but instead recover four apparent bands of higher molecular masses. It is speculated that the molecular masses of native phylloplanins I-IV are increased due to the occurrence of complexes with cuticular lipids, or trichome exudate diterpenes or sugar esters. These complexes could serve to increase phylloplanin solubility in TGST exudate (diterpenes and sugar esters) and their subsequent dispersion on the leaf surface. Amphipathic sugar esters are known to solubilize largely hydrophobic diterpenes of TGST exudate. It is noted that highly hydrophobic, basic saposin-like proteins of animals (see below) also display anomalous migration in SDS-PAGE (Curstedt, T. et al. 1987 Eur. J. Biochem. 168:255-262), and it is suggested that phylloplanins may behave similarly. Putative sequences from *Arabidopsis thaliana* (Accession BAB02757) (SEQ ID NO:19) and from *Oryza sativa* (Accession BAC83536) (SEQ ID NO:20) have significant percent similarity to the Phylloplanin cDNA, as do unannotated ESTs from *N. sylvestris, Solanum tuberosum*, and *Lycopersicon esculentum*. The genomic structure of gene Phylloplanin was elucidated from *N. tabacum* genomic DNA using a Genomewalker kit. The gene contains two exons (1: 175 bp; 2: 278 bp) that are separated by a 508 bp intron.

TABLE 1

Amino acid sequences recovered from phylloplanin N-terminal analyses, trypsin digestion, and pepsin digestion

| Method | Peak (min) | Phylloplanin | Amino Acid Sequence | Name | | |
|---|---|---|---|---|---|---|
| N-terminus | N/A | I | ILVPTLVST | (SEQ ID NO: 21) | | |
| | N/A | II | ILVPTLVSTHISGLVFCSV | (SEQ ID NO: 22) | aa-N1 |
| | N/A | III | ILVPTLVSTHISGLVFCSV | (SEQ ID NO: 23) | aa-N1 |
| | N/A | IV | ILVPTLVSTHISGLVFCSV (major) | (SEQ ID NO: 24) | aa-N1 |

TABLE 1-continued

Amino acid sequences recovered from phylloplanin N-terminal analyses, trypsin digestion, and pepsin digestion

| Method | Peak (min) | Phylloplanin | Amino Acid Sequence | Name | |
|---|---|---|---|---|---|
| Trypsin | 36.2 | I | ASVQLR | (SEQ ID NO: 25) | aa-T1 |
|  | 59.8 | I | ILNLNI (major) | (SEQ ID NO: 26) | aa-T4 |
|  |  |  | CGATNVISSTIT (minor) | (SEQ ID NO: 27) | aa-T2 |
|  | 56.7 | III | LVVATPLSTCxATLxSVG | (SEQ ID NO: 28) | aa-T3 |
|  | 58.7 | III | ILNLNI (major) | (SEQ ID NO: 29) | aa-T4 |
|  |  |  | CGATxVxSSTIT (minor) | (SEQ ID NO: 30) | aa-T2 |
| Pepsin |  | I, II, III, IV | IRVGLAPTG | (SEQ ID NO: 31) | aa-P1 |

*Escherichia coli*-Expressed T-Phylloplanin

Figure 4:
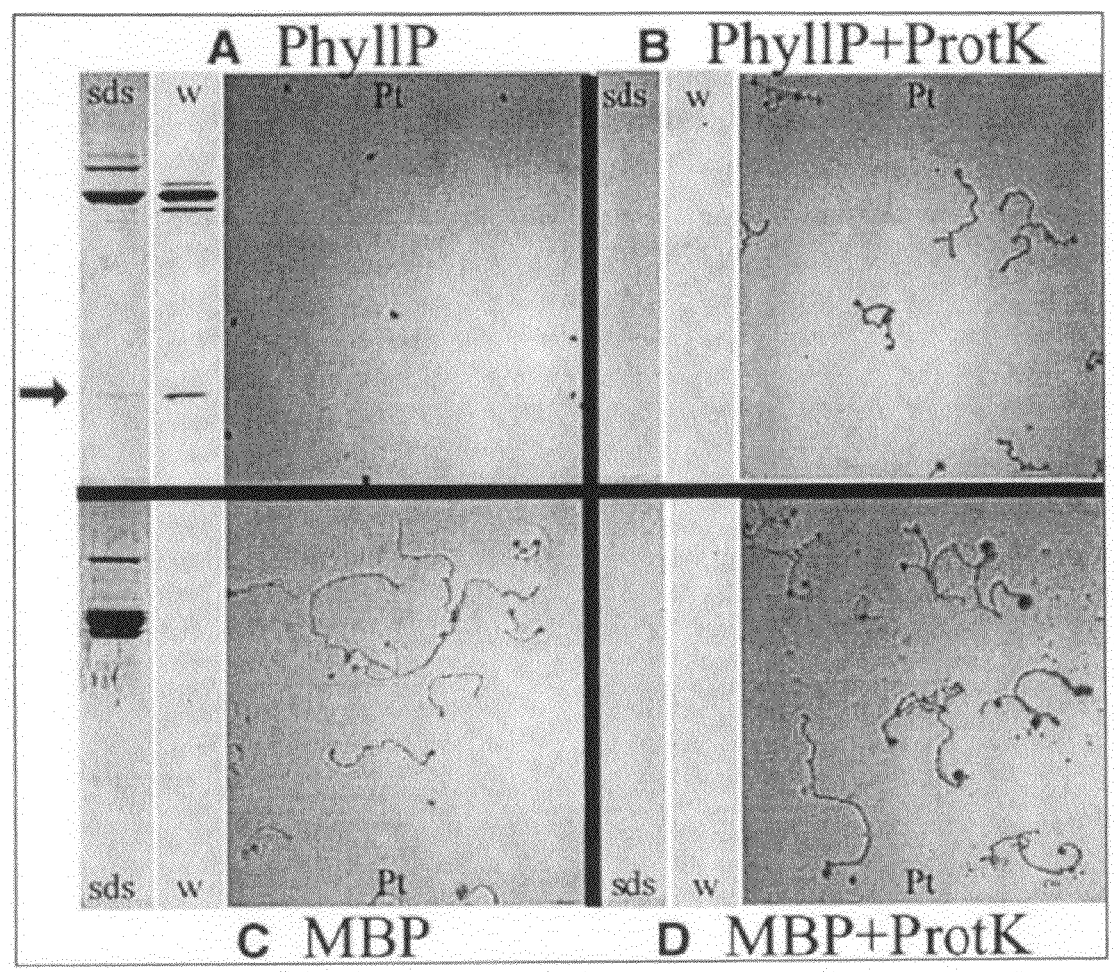

A 10.3 kDa portion of the Phylloplanin gene (PhyllP) was expressed in *E. coli* as a fusion protein with MBP. Soluble fusion protein (MBP-PhyllP) was purified on an amylose column, cut with the protease Factor Xa to release PhyllP, and desalted on a 3 kDa centrifugal filter. Both MBP-PhyllP and PhyllP reacted with the phylloplanin-specific antibody (FIG. 4). The sample containing PhyllP inhibited *P. tabacina* spore germination at total protein concentrations greater than 160 ng/µl (FIG. 4a). Protease digestion relieved PhyllP inhibition of spore germination (FIG. 4b). A control sample containing MBP alone, produced by an empty pMal-c2x vector and treated exactly as the PhyllP sample, had no effect on spore germination (FIG. 4c), nor did protease-treated MBP (FIG. 4d), at total protein concentrations ≦500 ng/µl. We note that no inhibition of spore germination was observed with MBP-PhyllP fusion protein not treated with Factor Xa. It was concluded that released PhyllP is responsible for the observed inhibition, and since it is evident (FIG. 4a, SDS gel) that released PhyllP is a minor component of the sample, the inhibitory concentration of PhyllP is considered <<160 ng/µl PhyllP was lost when purification from MBP and Factor Xa was attempted.

In leaf infection assays performed with KY 14 plants, PhyllP did not totally inhibit infection, but it greatly reduced necrotic leaf damage. MBP and uncut MBP-PhyllP fusion samples allowed successful infections. Lack of total inhibition with PhyllP may be due to insufficient protein concentration, or alternatively, adducts with lipids or trichome exudate components are essential for a native-protein like response.

Figure 5:
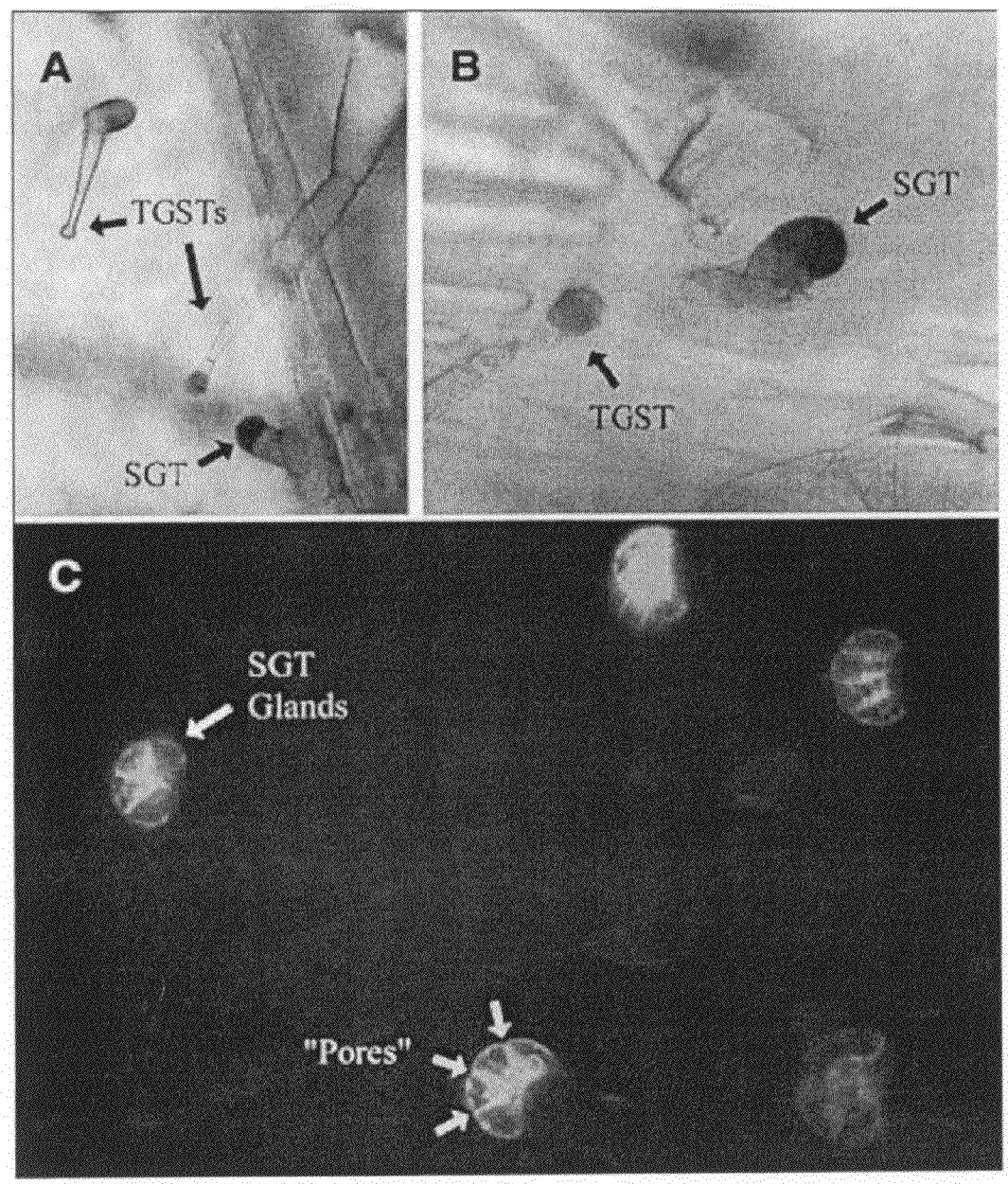
Figure 6:
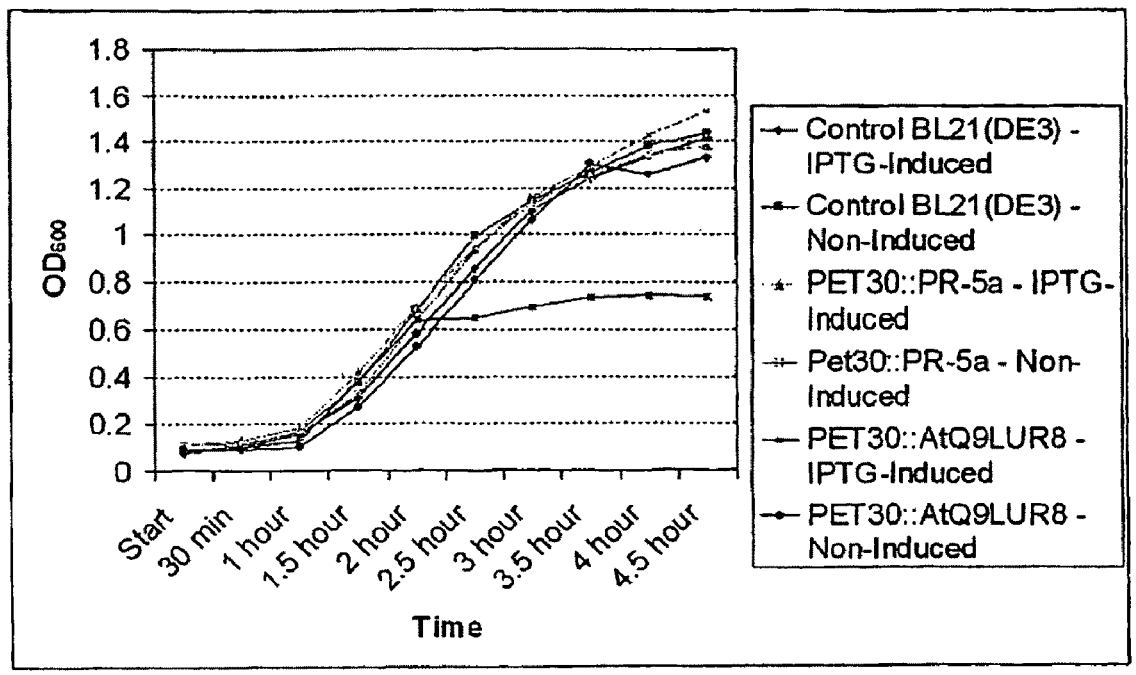
Figure 7:
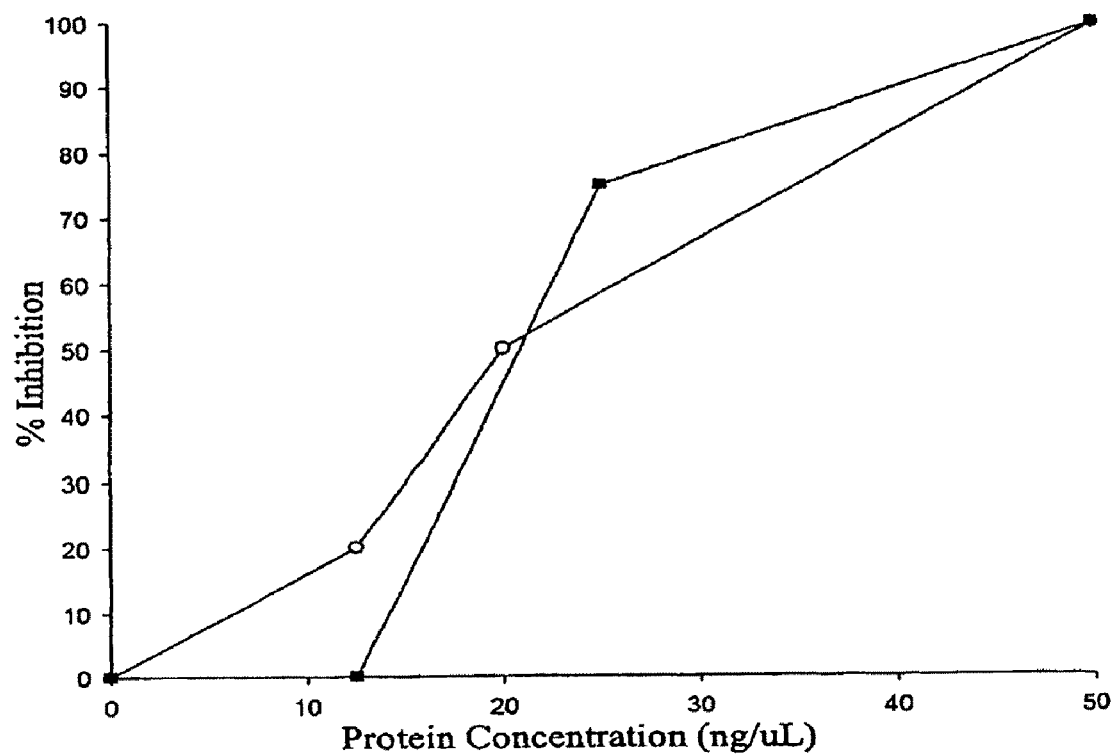

The T-Phylloplanin Promoter Region Directs Expression in Small Glandular Trichomes 1.8 kb of genomic DNA sequence was elucidated upstream from the Phylloplanin transcription start site. A 1.1 kb region of this DNA, as well as the 5'UTR and the Phylloplanin signal sequence, was fused in-frame with the reporter genes .beta.-glucuronidase (GUS) and Green Fluorescent Protein (GFP) and introduced into TI 1068 plants using *Agrobacterium* mediated plant transformation. GUS and GFP were expressed only in SGTs (FIG. 5), indicating activity of a SGT-specific promoter. TI 1068 SGTs are uniformly distributed over the leaf surface and protrude over surrounding epidermal cells (FIG. 1A). It appears that phylloplanins are biosynthesized locally in SGTs and are secreted to the leaf surface where, because of their hydrophobicity and basicity, phylloplanins dissolve in TGST exudate and are dispersed widely on the leaf surface during exudate flow, as exudate can reach about 17% of leaf dry weight in TI 1068. Certain animal saposin proteins are also hydrophobic and basic, are secreted by epithelial cells, and operate as components of innate immunity at the pulmonary air:water interface (Weaver, T. E. and Conkright, J. J. 2001 Ann. Rev. Physiol. 63:555-578).

Ultrastructural studies of Akers et al. (Akers, C. P. et al. 1978 J. Bot. 65:282-292) defined the structures of *N. tabacum* L. cv Xanthi SGTs and TGSTs. Glands of SGTs were observed to have about four cells separated by large intracellular spaces that contained substantial $OsO_4$ stained material, apparently destined for secretion outside the gland. The nature of the accumulated substance was not defined, and it is now concluded that this substance is phylloplanins, as phylloplanins have been found on all tobaccos during this investigation. The pattern of intracellular space disposition observed in that study is very similar to that observed here using the phylloplanin-promoter-GFP construct (FIG. 5C). It was concluded that phylloplanins are produced exclusively in SGT gland cells, secreted to gland extracellular spaces, and then transferred outside the glands through constrictions at termini of intracellular spaces which is presumed to be "secretory pores" (yellow arrows, FIG. 5C) of unknown structure.

The majority of plant pathogens are fungi. When airborne spores land on a leaf surface, germination is the initial step leading to host colonization. It is hypothesized that by rapidly inhibiting spore germination at the leaf surface, preformed plant proteins may suppress pathogen infection before induced defenses become functional, in a manner analogous to secreted surface proteins of animals. This hypothesis is supported by the observations that surface-accumulated *N. tabacum* phylloplanins I-IV and *E. coli-expressed* PhyllP inhibit *P. tabacina* spore germination in vitro and limit leaf infection in situ. This hypothesis is also supported by the observation that the phylloplanin promoter directs expression specifically in SGTs, and from this we propose that phylloplanins are secreted to the leaf surface. Three observations link the gene Phylloplanin to phylloplanin I-IV proteins collected from the leaf surface. First, all amino acid sequences recovered from leaf surface phylloplanins I-IV are present in the predicted protein sequence from Phylloplanin, representing 54% of the mature protein open reading frame. Secondly, a functional link is provided between the gene and the proteins by replicating LWW blue mold inhibition with *E. coli-*expressed PhyllP. The phylloplanin promoter is a third, critical link between the gene and the proteins, and implicates SGTs as the sites of phylloplanin biosynthesis and delivery to the surface.

Secreted phylloplanins represent a novel leaf surface defense in the plant kingdom, wherein protein biosynthesis in SGTs allows deposition and dispersion of phylloplanins on leaf aerial surfaces to deter pathogen establishment. Further study is needed to identify the post-translational modifications or biochemical adducts thought to be present in phylloplanins I-IV, and to elucidate the mechanisms of phylloplanin-mediated fungal inhibition. It is emphasized that this work shows that SGTs must be regarded as specialized biosynthetic structures akin to TGSTs. Further study is needed to understand details of how SGTs deliver phylloplanins to the leaf surface, and whether these surface-disposed "protein factories" can be utilized for molecular farming.

Biological Material and Growth Conditions.

Greenhouse plants (*Nicotiana tabacum* L. tobacco introduction (TI) 1068, TI 1112, TI 1406; cultivars KY 14 and Petite Havana SR1 [hereafter referred to by TI number or cultivar name]) were germinated and grown in soil under natural light at 22-24° C. with weekly fertilization (20-20-20, N-P-K). Plants were transplanted into 15-cm pots and treated with the insecticide Marathon (Olympic Horticultural Products, Mainland, Pa.) at 3-4 wk post-emergence. Field plants (TI 1068, *Glycine max*, *Helianthus annus*) were grown at a farm near Lexington, Ky. during the 2002 growing season.

To grow sterile TI 1068 plants, seeds were immersed in 10% (v/v) sodium hypochlorite for 10 min, rinsed briefly in 70% (v/v) ethanol, washed 4 times in sterile water, and germinated on Murashige-Skoog (MS) medium (Murashige, T. and Skoog, F. 1962) containing B5 vitamins (100 mg/l myo-inositol, 10 mg/l thiamine-HCl, and 1 mg/l each pyridoxine-HCl and nicotinic acid) in a 22° C. growth chamber under fluorescent illumination (light/dark 16/8 h daily). Individual plants were transferred to PlantCons (ICN Biomedicals, Aurora, Ohio) containing MS agar at 3 wks post-emergence.

*E. coli* strain ER2508 (New England Biolabs, Beverly, Mass.) was stored and propagated as described by the supplier. Spores of *Peronospora tabacina* (isolate KY-79) were harvested from sporulating lesions on KY 14 plants as described (Reuveni, M. et al. 1986 Physiol. Mol. Plant. Pathol. 30:441-451).

Phylloplanin Collection and SDS-PAGE.

Water-soluble phylloplane components were collected from mature, fully-expanded leaves of all greenhouse-grown and field-grown plants by washing freshly-detached leaves in 200 ml nanopure water (NANOpure water system D4751, Barnstead/Thermolyne, Dubuque, Iowa) for 15 s. Cut petioles or cut leaf surfaces were not exposed to wash solutions.

Water washes were filtered (No. 1 filter paper, Whatman, Clifton, N.J.), lyophylized to dryness, resuspended in 3 ml sterile water, and centrifuged at 12,000×g for 5 min at 21° C. The supernatants were filtered (13 mm/0.45 µm syringe filter, Corning Glass Works, Corning, N.Y.) to exclude bacteria and fungi, and are hereafter referred to as leaf water washes (LWW).

Proteins were separated by SDS/12%/glycine-PAGE (Laemmli, U. K. 1970) or SDS/15%/tricine-PAGE (Judd, R. C. 1994) using a Mini-Protean II electrophoresis system (Bio-Rad, Hercules, Calif.), according to the manufacturer's instructions, and visualized with Coomassie blue or silver staining.

Protein concentration was estimated using the bicinchoninic acid assay (Pierce Chemical, Rockford, Ill.) with BSA as a standard. Leaf surface areas were estimated by tracing leaves onto uniform-weight paper and weighing the cutouts.

Collection of epidermal peels and extracellular fluid (EF). Epidermal peels were prepared from greenhouse-grown TI 1068 plants as described (Kandra, L. et al. 1990 E. J. Biochem. 188:385-391), pulverized with liquid $N_2$, and proteins were analyzed by SDS-PAGE. EF was collected using a vacuum infiltration method (Terry, M. E. and Bonner, B. A. 1980 Plant Physiol. 66:321-325) and analyzed by SDS-PAGE.

GC Analysis.

Trichome exudate was collected from greenhouse-grown TI 1068 by immersing unwashed leaves for 15 s in 200 ml acetonitrile. The wash solutions were filtered (No. 1 filter paper, Whatman), dried, and trichome exudate was resuspended in 5 ml acetonitrile and quantified by GC (flame ionization detection) as trimethylsilyl derivatives prepared in dimethylformamide, as previously described (Wang, E. et al. 2001 Nat Biotechnol 19:371-374). To determine the amounts of trichome exudate biochemicals occurring in LWW, volumes equivalent to 200 $cm^2$ leaf surface areas were transferred to glass GC vials and dried in a vacuum oven (37° C.) overnight. Trichome exudate biochemicals were extracted at 21° C. with methylene chloride, dried, solubilized, derivatized, and analyzed by GC. The amount of residual trichome exudate biochemicals in LWW was assessed relative to total trichome exudate on an equivalent surface area basis.

Phylloplanin Amino Acid Sequencing.

Proteins in greenhouse-grown TI 1068 LWW were separated by SDS-PAGE, transferred to polyvinyldifluoride (Immobilon-psq, Millipore, Bedford, Mass.) using a Mini-Protean II electroblot apparatus (Bio-Rad), and visualized with Coomassie blue. Phylloplanin bands were subjected to N-terminal sequencing using automated Edman degradation (Matsudaira, P. 1987 J. Biol. Chem. 262:10035-10038) at the University of Kentucky Macromolecular Structure Analysis Facility (Lexington, Ky.). To recover internal aa sequence information, LWW from greenhouse-grown TI 1068 was separated by SDS-PAGE, stained with Coomassie, and 21 kDa and 19 kDa bands were excised and digested with trypsin. Total proteins in TI 1068 LWW were also digested with pepsin. Resulting tryptic or peptic peptides were separated by reversed-phase HPLC (Aquapore RP-300 7 µm particle size octyl reversed-phase column [Applied Biosystems, San Jose, Calif.]), manually collected based on absorbance at 214 nm, and samples were reduced in volume under vacuum to about 50 µl. Amino acid sequence analyses of tryptic peptides were performed as above. For peptic peptides, similar analyses were performed at The Protein Facility of Iowa State University (Ames, Iowa).

*A. thaliana* AAP75801 cloning and expression in *E. coli* Total RNA was isolated from *A. thaliana* leaf tissue (100 mg FW) using an RNaqueous isolation kit. cDNA was synthesized from 5 µg total RNA using a Qiagen Omniscript RT kit, according to the manufacturer's protocol. The PCR amplification reaction (50 µl volume) was performed using PCR master mix (Promega), 2 µl cDNA template and 0.2 µM each of a primer pair designed from the GenBank *A. thaliana* AAP75801 mRNA sequence, RS102-s (5'-ATGGGGGAA-GACACTTTATCACATCCAAAAC-3') (SEQ ID NO:32) and RWS102-as (5'-TCAGTTAAGAAGACCAAAGCCG-GCAGG-3') (SEQ ID NO:33). The PCR product was size-fractionated by electrophoresis in a 1.0% (w/v) agarose gel, isolated using a gel extraction kit (Qiagen Qiaex II), cloned into a pGem-T vector (Promega), and the purified plasmid (pGemT::AAP75801) was sequenced.

To overexpress AAP75801 in *E. coli*, the coding sequence was amplified from pGemT::AAP75801 using the primers RWS109-s (5'-GACGACGACAAGATGGGGGAAGACACTTTAT CACA-3' (SEQ ID NO:34); the underlined section is for ligation independent cloning (LIC), the bold text is the start codon) and RWS 109-as (5'-GAGGAGAAGCCCGGT-CAGTTAAGAAGA CCAAAGCC-3' (SEQ ID NO:35); the underlined section is for LIC, the bold text is the stop codon). Amplification was performed for 32 cycles using the following thermal profile: 95° C. for 45 s, 60° C. for 45 s, 72° C. for 45 s, followed by a final 5 min extension at 72° C. The PCR product was size-fractionated by electrophoresis in a 1.0% (w/v) agarose gel, and isolated using a gel extraction kit. The product was then annealed with the pET-30 Ek/LIC vector (Novagen), according to the manufacturer's ligation independent protocol, and cloned into E. coli BL21 (DE3) competent cells. Cultures (ranging in volumes from 100 ml to 1000 ml) were incubated at 37° C. (or 28° C. for low-temperature experiments) with shaking (250 rpm). When $OD_{600}$ reached 0.6, isopropyl-beta-D-thiogalactoside (ITPG) was added to a final concentration of 0.1 mM, and the culture was incubated with shaking for another 2 hours. Immediately after IPTG induction of protein expression, the Pet30:AAP75801 culture stopped growing (Fig. X). We were unable to prepare any heterologous AAP75801 from induced cultures, even using 1 L culture volumes and His-tag binding resin mediated column chromatography. These results indicate that the AAP75801 gene product is antibacterial.

Degenerate RT-PCR, RLM-RACE, and Elucidation of Genomic Structure. Total RNA was extracted from TI 1068 leaf tissue (100 mg fresh weight (FW)) with an RNeasy kit (Qiagen, Chatsworth, Calif.), and cDNA was synthesized from 5 μg total RNA using an Omniscript RT kit (Qiagen). PCR was performed using PCR master mix (Promega, Madison, Wis.) containing 3 μl cDNA template and 4 μM of each primer in a 50 μl volume. Successful amplification of a PCR product occurred with the primers 5'-ACWTTIGTITCI-ACWCATATYTCIGGICTIGTYTTTTG-3'(SEQ ID NO:1) and 5'-AARAAICCIGTIGGIGCIARICCIACYCTAAT-3' (SEQ ID NO:2) where I=Inosine, W=A or T, Y=C or T, and R=A or G. Amplification was for 46 cycles using the following thermal profile: 95° C. for 45 s, 50° C. for 45 s, 72° C. for 1 min, followed by a final 4 min extension at 72° C. The PCR product was size-fractionated by electrophoresis in a 1% (w/v) agarose gel, extracted using a Qiaex II kit (Qiagen), cloned into a pGem-T vector (Promega), and sequenced.

For RNA ligase mediated rapid amplification of cDNA ends (RLM-RACE), total RNA was extracted from TI 1068 leaf tissue, as above. A GeneRacer kit (Invitrogen, Grand Island, N.Y.) containing SuperScript III was used to generate cDNAs, according to the manufacturer's instructions. Successful amplification of a 3'RACE product occurred with the GeneRacer 3'Primer and the gene-specific primer 5'-CTCAGTCCCCAAGTTTTTCCTAATGCATCAG-3'(SEQ ID NO:3). Successful amplification of a 5'RACE product occurred with the GeneRacer 5'Primer and the gene-specific primer 5'-GGCCAAGAAAGTTAACTAGCTGATGCATA-3'(SEQ ID NO:4). PCR cycling parameters were according to the GeneRacer protocol.

Phylloplanin genomic structure was elucidated using a GenomeWalker kit (Clontech, Palo Alto, Calif.), according to the manufacturer's protocol, using genomic DNA isolated from TI 1068 leaf tissue (100 mg FW) with a DNeasy plant kit (Qiagen). Primary PCR reactions were performed with a sense outer adaptor primer AP1, provided in the kit, and the antisense Phylloplanin-specific primer (5'-TGGAACAAG-TATGGCAAATGCAGCGGGG-3') (SEQ ID NO:5). Primary PCR cycling parameters were 7 cycles of 25 s at 94° C. and 3 min at 72° C., followed by 32 cycles of 25 s at 94° C. and 3 min at 67° C., with a final extension of 7 min at 67° C. Products of primary PCR were diluted 1:25 and 1 μl was used in nested PCR reactions with a sense inner adaptor primer (AP2), provided in the kit, and a nested antisense Phylloplanin-specific primer (5'-GGGGGTTGCGATTAATGCAGC-CAAAAGGAAAA-3') (SEQ ID NO:6). Nested PCR cycling parameters were 5 cycles of 25 s at 94° C. and 3 min at 72° C., followed by 20 cycles of 25 s at 94° C. and 3 min at 67° C., with a final extension of 7 min at 67° C. Amplified PCR products were amplified, size fractionated by gel electrophoresis, gel-extracted, cloned into pGem-T, and sequenced.

Expression vector construction and fusion protein purification. To overexpress the Phylloplanin gene in E. coli, a 10.3 kDa portion of the coding sequence (His33-Gly142, termed PhyllP) and the full-length mature protein coding sequence (Ile24-Asn150) were amplified incorporating XbaI and PstI restriction sites (PhyllP-sense: 5'-AGCTTCTAGA-CATATTTCGGGGCTGGTTTT (SEQ ID NO:7); PhyllP-antisense: 5'-AGCTCTGCAGTTAGCCGGTGGGGG CGAG-GCC-3' (SEQ ID NO:8); Full-sense: 5'-AGCT TCTAGAATACTTGTT CCAACACT-3' (SEQ ID NO:9); Full-antisense: 5'-AGCTCTGCAGTTAATTGATG TTAAGA-3' (SEQ ID NO:10); restriction sites underlined). The PCR products were digested with XbaI and PstI and cloned into the pMal-c2x expression vector (New England Biolabs) to create a translation fusion between the gene inserts and malE (which encodes Maltose Binding Protein (MBP)). Protein expression was induced at 0.5 $OD_{600}$ by the addition of 0.1 mM isopropyl-beta-D-thiogalactoside. Cells were harvested and resuspended in column binding buffer (20 mM Tris-HCl, pH 7.4, 200 mM NaCl, 1 mM EDTA) containing 1 mg/ml lysozyme. Cell lysate was centrifuged at 10,000×g for 10 min and the resulting supernatant was collected. Fusion protein was purified using amylose-mediated column chromatography (New England Biolabs) according to the manufacturer's instructions and examined by SDS-PAGE. Fractions containing purified fusion protein were pooled and concentrated to about 1 mg/ml using a 3 kDa centrifugal filter (Microsep 3K Omega, Pall Laboratories, Ft. Myers, Fla.). Factor Xa (New England Biolabs) was added and samples were incubated for 48 h at 21° C. Salts and buffer components were removed using a 3 kDa centrifugal filter, and protein concentration was adjusted to 1 mg/ml with the addition of sterile water.

Phylloplanin antibody and western blots. TI 1068 LWW was separated by SDS-PAGE and stained with Coomassie Blue. Phylloplanin III was excised and used to generate a rabbit polyclonal antibody (Strategic Biosolutions, Newark, Del.). Immunodetection was performed using a 1:10,000 dilution of phylloplanin antiserum and a 1:10,000 dilution of horseradish peroxidase-coupled anti-rabbit secondary antibody (Sigma, St. Louis, Mo.).

Protease treatment. Insoluble Proteinase K (ProtK) affixed to acrylic beads (100 mg; P0803, Sigma) was placed into mini-spin filters (732-6027, Bio-Rad). The filters containing beads were placed into empty 1.5 ml Eppendorf tubes, and the filters were washed with sterile water (700 μl; 2600 g for 1 min). The flow-through was discarded, and washing was repeated five times. The spin filters were transferred to empty 1.5 ml Eppendorf tubes. Samples were added to filters containing protease beads and incubated at 37.°. C. for 4 h, with periodic inversion to mix. The tubes were then centrifuged at 2600. x .g for 10 min, and the flow-through from each was collected and analyzed by SDS-PAGE or used in blue mold assays.

*Peronospora tabacina* spore germination and leaf infection assays. Freshly-collected *P. tabacina* spores were mixed with various concentrations of TI 1068 LWW, ProtK-treated TI 1068 LWW, or water incubated with ProtK, and germinated for 16 h in dark, humidified chambers as water drops (4 drops; 50 μl spores/μl) on microscope slides. The spores were then inspected visually at 100× magnification for germination. The absence of a germination tube after 16 h indicated inhibition. Similar experiments were performed with PhyllP, MBP, ProtK-treated PhyllP, and ProtK-treated MBP. To assess the immediacy of germination tube arrest by LWW, spores were observed after 3 h.

For the leaf infection assay, 6-wk-old, greenhouse-grown Petite Havana SR1 plants were pre-conditioned by incubation in a 21° C. growth room (14 h light) for 5 days. Dilution series (1, 5, 12.5, 25, 50, 75, 100 ng protein/µl) of TI 1068 LWW were prepared and mixed with freshly-collected *P. tabacina* spores immediately before inoculation. For each LWW dilution, 8-10 drops (4 µl drops; 100 spores/µl) were applied to one leaf of pre-conditioned plants. Plants were placed in dark, humidified chambers for 16 h to provide optimal conditions for infection, and then returned to the growth room. Treated leaves were excised 5 days after inoculation, placed in dark, humid chambers for 16 h, and then inspected for sporulation. The formation of *P. tabacina* sporulating lesions indicated successful leaf infection.

Elucidation of phylloplanin promoter sequence and activity. Genomic DNA was isolated from TI 1068 leaf tissue (100 mg FW) using a DNeasy plant mini kit (Qiagen). The DNA sequence upstream of the Phylloplanin gene was recovered using a GenomeWalker kit (Clontech), according to the manufacturer's protocol. Briefly, about 4 μg genomic DNA was digested to completion (36 h) in four separate reactions with restriction enzymes that generated blunt ends (Dra I, EcoR V, Pvu II, Stu II). The resulting 'libraries' were purified by phenol/chloroform extraction and precipitation. Digested genomic DNA in each library were then ligated to 5'GenomeWalker Adaptor molecules and purified again. A primary PCR reaction for each library was performed with a sense outer adaptor primer AP1, provided in the kit, and the antisense Phylloplanin-specific primer (5'-TGGAACAAGTATGGCAAA TGCAGCGGGG-3') (SEQ ID NO:5). Primary PCR cycling parameters were seven cycles of 25 s at 94° C. and 3 min at 72° C., followed by 32 cycles of 25 s at 94° C. and 3 min at 67° C., with a final extension of 7 min at 67° C. Products of primary PCR were diluted 1:25 and 1 μl was used in nested PCR reactions with a sense inner adaptor primer AP2, provided in the kit, and a nested antisense Phylloplanin-specific primer (5'-GGGGGTTGCGATTAATGCAGCCAAAAGGAAAA-3') (SEQ ID NO:6). Nested PCR cycling parameters were five cycles of 25 s at 94° C. and 3 min at 72° C., followed by 20 cycles of 25 s at 94 C.° and 3 min at 67° C., with a final extension of 7 min at 67° C. A 1.8 kB product was amplified from the Stu II-based library, and gel-extracted, cloned into pGem-T, and sequenced.

PCR using a Phylloplanin promoter-specific sense primer (5'-TGCTCCCACCACTAGAATCACCA-3') (SEQ ID NO:11) and a Phylloplanin-specific antisense primer with an Xba I cut site (5'-AGCTTCTAGATGTTGGAA CAAGTATGG-3' (SEQ ID NO:12); Xba I site underlined) was then used to amplify the region of *N. tabacum* genomic DNA that included the first 25 amino acids of the phylloplanin protein (which included the signal sequence), the 5' UTR, and a further 1.1 kB upstream. The PCR product was then cut with Xba I and HinD III (at a restriction site endogenous to the promoter) and cloned into the HinD III/Xba I-sites of pBIMC (kindly provided by D. Falcone, pBIMC is a variant of pBI121 modified to include a polylinker in place of the GUS gene) to replace the CaMV-35S promoter and create the vector pBI-PhylloProm. To analyze the spatial expression of the promoter, the reporter genes GUS and sGFP (kindly provided by D. Falcone) were PCR-amplified with primers that incorporated Xba I and Xho I restriction sites (GUS-sense: 5'-AGCT TCTAGAATGTTACGTCCTGTAGAAACCCCA-3' (SEQ ID NO:13); GUS-antisense: 5'-AGCT CTCGAGTCATTGTTTGCCTCCCTGCT-3' (SEQ ID NO:14); sGFP-sense: 5'-AGCT TCTAGAATGGTGAGCAAGGGCGAGGA-3' (SEQ ID NO:15); sGFP-antisense: 5'-AGCT CTCGAGGCTTTACTTGTACAGCTCGT-3' (SEQ ID NO:16); restriction sites underlined). The PCR products were gel-extracted, cut with Xba I and Xha I, and ligated between Xba I/Xho I sites in the polylinker of pBI-PhylloProm to create in-frame fusions with the Phylloplanin start codon and signal sequence. These constructs were transformed into *Agrobacterium tumefaciens* GV3101 by triparental mating, and introduced into TI 1068 using the leaf disk method (Horsch, R. B. et al. 1985 Science 227:1229-1231). Kanamycin-resistant plantlets were derived from kanamycin-resistant callus tissue and transferred to soil. Leaf disks from pBI-PhylloProm:GUS explants were stained for GUS activity by incubation with 0.1% X-gluc (Jefferson, R. A. 1987) and photographed. Leaf disks from pBI-PhylloProm:GFP explants were magnified and photographed using a Zeiss Axioplan-2 imaging system.

Sequence data have been deposited with the EMBL/GenBank data libraries under accession number AY705384.

Bioinformatic Analysis

Homologous open reading frames of selected cDNA or EST sequences giving significant (e-value cutoff $10^{-4}$) BLASTn, BLASTp, and tBLASTx (Altschul et al., 1990 J. Mol. Biol. 215:403-410) scores against T-Phylloplanin nucleotide and amino acid sequences were first analyzed for the presence of signal peptides using TargetP. A multiple alignment of protein sequences with the predicted signal peptides removed was performed using the CLUSTALW algorithm (DNASTAR Lasergene Software, Madison, Wis. (See FIG. 8A)).

The identity of the sequences compared to that of TI 1068 Phylloplanin cDNA (Genbank Accession No. AY705384) are as follows:

| Genbank Accession No. | Species |
|---|---|
| BG525459 | *Stevia rebaudiana* (SEQ ID NO: 36) |
| CV545024 | *Brassica rapa* (subspecies *pekinensis*) (SEQ ID NO: 37) |
| CD847345 | *Helianthus annuus* (SEQ ID NO: 38) |
| AAP75801 | *Arabidopsis thaliana* (SEQ ID NO: 39) |
| AAN28743 | *Arabidopsis thaliana* (subspecies *thalecress*) (SEQ ID NO: 40) |
| XP479490 | *Oryza sativa* (SEQ ID NO: 41) |
| XP479489 | *Oryza satvia* (SEQ ID NO: 42) |
| CV502724 | *Solanum tuberosum* (SEQ ID NO: 43) |
| BP903020 | *Lycopersicon esculentum* (SEQ ID NO: 44) |
| AJ789767 | *Antirrhinum majus* (SEQ ID NO: 45) |
| BU829351 | *Populustremula* x *populus tremuloides* (SEQ ID NO: 46) |
| BM527339 | Soybean clone ID Gm-c1061-3715 (SEQ ID NO: 47) |
| BM371086 | *Hardeum vulgare* (SEQ ID NO: 48) |

All of the foregoing accession numbers are incorporated by reference.

An unrooted phylogenetic tree was constructed using the maximum parsimony algorithm PROTPARS in the PHYLIP version 3.63 software package (Felsenstein, 2004), and tree robustness was estimated with 1000 bootstrapped data sets. The tree was displayed with the TREEVIEW version 3.2 software (Page, 1996). (See FIG. 8B).

We have surveyed about 45 different plants and have shown that surface proteins occur on most species tested, but the amounts, number and size (as determined by protein electrophoresis—SDS-PAGE) of the surface proteins present varies greatly with species. The phylloplanins analyzed herein are hydrophobic, basic, and, in their natural state, highly glycosylated. They have amphipathic solubility properties and can be washed from leaf surfaces with water.

T-phylloplanins are shown to be produced by a specific trichome (leaf hair) type (short glandular trichome, 1). The most extensively characterized phylloplanin is T-phylloplanin, however our current focus is on S-phylloplanins, obtained from sunflower (*Helianthus annum*). We have shown that T-phylloplanins inhibit *Peronospora tabacina* spore germination and on-plant disease of this obligate biotrophic oomycete that causes blue mold disease on *N. tabacum*.

Experimental tobacco (*Nicotiana tabacum*) 'T.I.1068', sunflower (*Helianthus annus*) 'Dove Hybrid', jimson wee (*Datura metel*), and solybean (*Glycine max*) var. *Harsoy* were grown in the greenhouse under natural light at 22° C. to 24° C. with weekly fertilization with 20:20:20 NPK, primarily between September and July. To determine leaf area, leaves were traced onto uniform-weight paper and areas were determined by weighing tracings. LWWs, obtained by washing leaves in distilled water for 20 s with gentle agitation, were lyolphilized, resuspended in distilled water and centrifuged at 12,000 g for 5 min before supernatants were used. Quantification of LWWs was made on the basis of leaf surface area from which they were obtained (assuming most phylloplanin to be in the adaxial surface) because standard protein assays using the Bio-Rad (Bio-Rad Laboratories) and bicinchoninic acid (Pierce Chemical Company) did not provide reliable results. LWW quantity is described as $cm^2$asae. SDS-12% Glycine-PAGE and silver staining was as previously described Shepherd et al. 2005). The glycoprotein nature of phylloplanins was assessed using the Glyco-Profile III. Fluorescent glycoprotein detection kit (Sigma-Aldrich). Glycosylation indicator controls included the use of the relatively highly glycosylated proteins ovalbumin and RNAse B and bovine serum albumin and β-casein, proteins lacking glycosylation. And parallel experiments were; made with and without periodic aid reagent. To assess distribution of T-phylloplanins on the adaxial versus abaxial surfaces, leaves were gently sprayed with distilled water using a fine airbrush sprayer, first the adaxial surface than the abaxial surface. Three consecutive sprayings were made of each surface were collected separately, lyophilized and analyzed.

Tobacco, sunflower and soybean have very high, moderate and low levels of phylloplanins respectively, based on SDS-PAGE analysis or similar surface area equivalents of LWWs. These LWWs were assayed for their ability to inhibit *P. tabacina* spore germination and leaf infection and compared (Kroumova et al. Plant Physiology (August 2007) 144:1843-181 incorporated herein in its entirety by reference). The assays were essentially as described above using 400 spores/4 μl in both assays. *P. tabacina* susceptible tobacco 'KY14' was used for leaf infection inhibition assays of plant LWWs.

Figure 13:
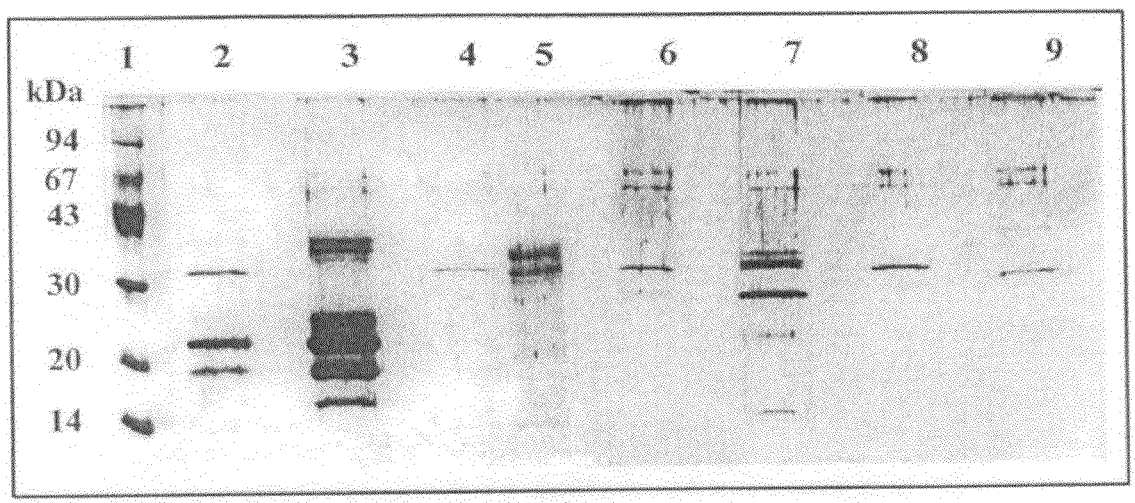

LWW phylloplanins of sunflower and jimson weed like T-phylloplanins of tobacco, were sensitive to proteolysis. Treatment with insoluble Proteinase K resulted in the loss of major LWW polypeptides in each case. See e.g., FIG. 13.

We isolated the T-phylloplanin gene and its promoter (Shepherd et al. 2007 The Plant Cell 17:1851-1861) and recently showed, using reverse genetics, that knockdown of the gene results in susceptibility of a normally resistant experimental *N. tabacum* type to blue mold (Kroumova et al., Plant Physiology (August 2007) 144:1843-1851 incorporated herein in its entirety by reference). As demonstrated above S-phylloplanins from *Helianthus annuus* and D-phyllopanins from *Datura metel* also inhibit *P. tabacina* spore germination and disease, even though *P. tabacina* does not cause blue mold disease on these plants.

The foregoing demonstrates that the phylloplanins of this invention have a broad spectrum anti-fungal activity.

To convey the amount of leaf material needed to prepare a phylloplanin containing LWW capable of inhibiting by 100% *P. tabacina* spore germination and on-leaf, blue mold disease (where spores and LWW are mixed and applied as a 4 μl spot to leaves of a susceptible *N. tabacum*), we note the surface area equivalents of phylloplanins in LWWs required. The equivalents for *N. tabacum, Helianthus annuum*, and *Datura metel* are: 0.25, 0.05, and 1.5 $cm^2$, respectively. Clearly, it is not difficult to prepare large amounts of these compounds from greenhouse or field grown plants. We have shown antifungal activities of LWWs from both.

Inhibition of *Pyricularia grisea* and *Rhizctonia solani* growth by LWWs containing T-phylloplanin or S-phyllopanin.

Figure 10:
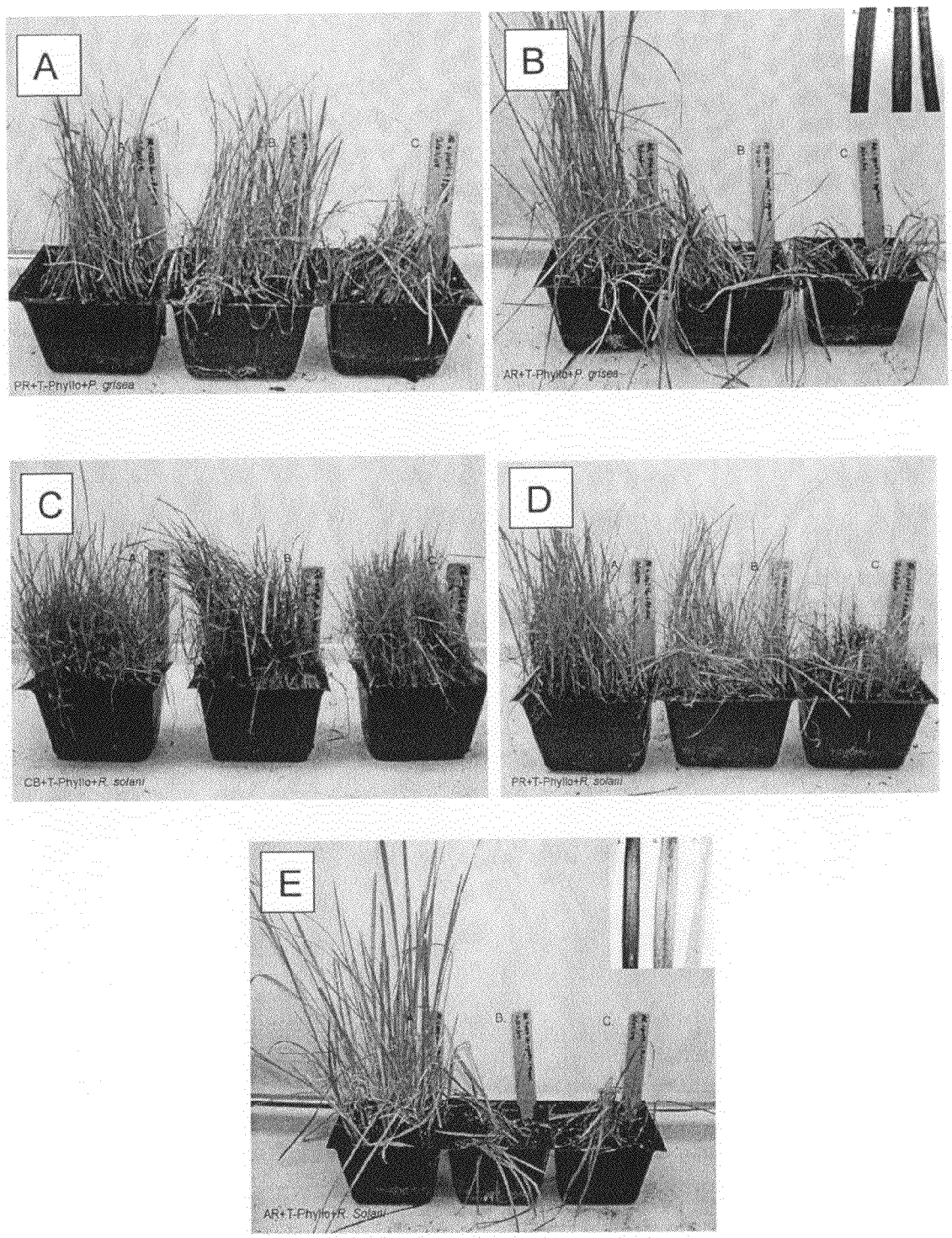
Figure 11:
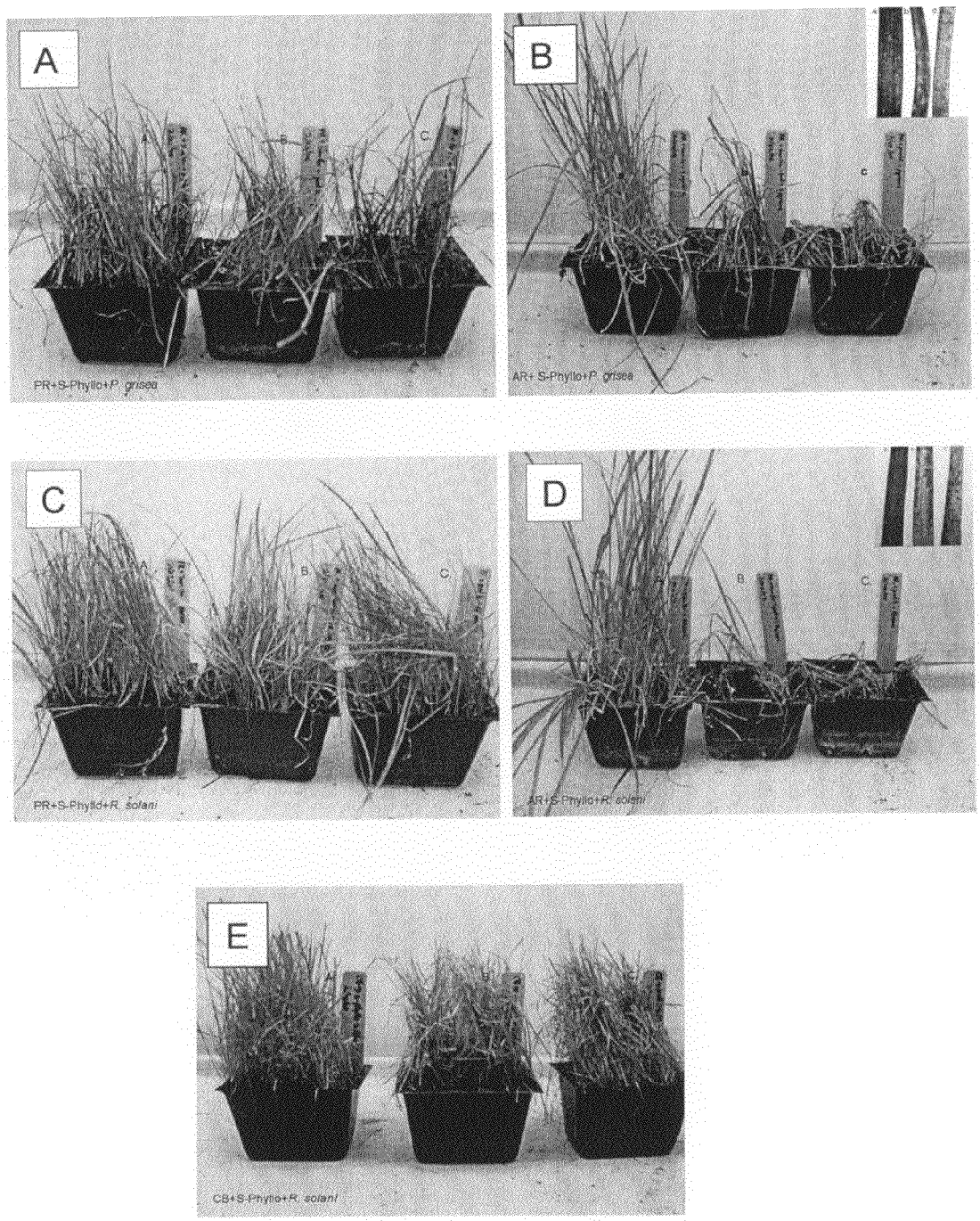
Figure 12:
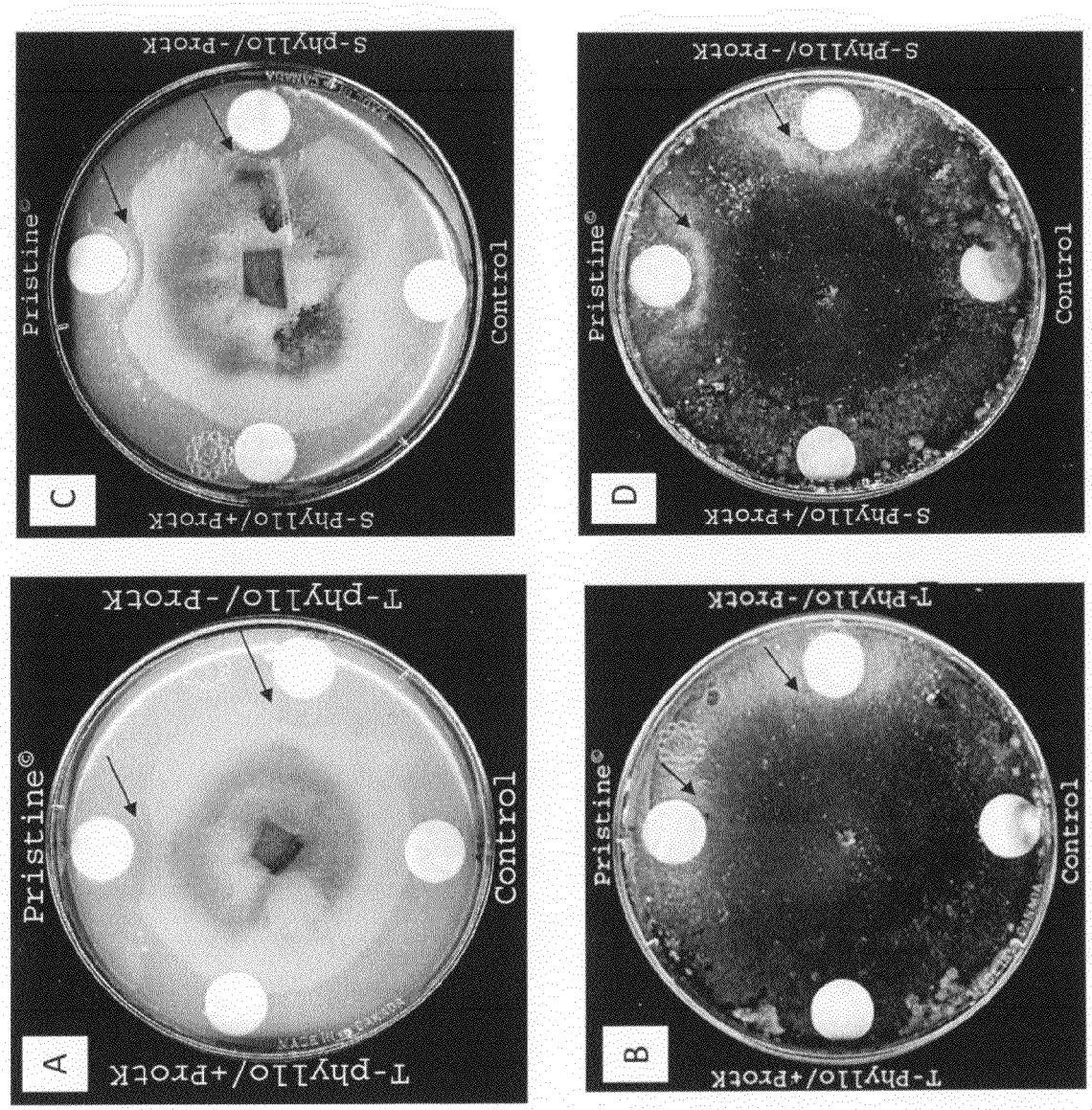

LWWs were prepared from sunflower and tobacco leaves as described above, i.e.,

The ability of the LWWs to inhibit diseases caused by the basidiomycete fungus *R. solani* (causes Brown Patch in annual rye grass (*Lolium multiflorum*), perennial rye grass (*Lolium perenne*), and creeping bentgrass (*Agrostis palustris*); Target Spot in tobacco; and *Rhizctonia* seedling blight in sunflower) and diseases caused by the ascomycete fungus *P. grisea* (causes Grey Leaf Spot in annual and perennial rye grasses) was assayed using on-plant-disease assays (FIGS. 10 and 11) and in vitro, petri plate assays (FIG. 12).

The inhibitory effects of LWW containing T-phylloplanin or S-Phylloplanins on the growth of *Pyricularia grisea* or *Rhizctonia solani* on grasses, in particular annual rye grass (*Lolium multiflorum*), perennial rye grass (*Lolium perenne*), and creeping bentgrass (*Agrostis palustris*) was assayed by spraying the grasses with a Proteinase K solution without phylloplanins, with LWW containing T-phylloplanin, or with LWW containing T-Phylloplanin treated with Proteinase K prior to inoculation with mycelia of *Pyricularia grisea* or *Rhizctonia solani*. The results, presented in FIG. 10, demonstrate the healthy growth of T-Phylloplanin treated grasses (the left most pots of each set), and deterioration of the grasses in the center and right situated pots where phylloplanin was ProteinaseK pre-treated, or the ProteinaseK control was applied. Insets show symptoms of diseases on leaf blades of pot c, and healthy leaf blades in pot a.

Petri Plate Assay: We also assayed the ability of S-, D-, and T-phylloplanins to inhibit hyphal growth of a basidiomycete and ascomycete fungi, in vitro. Sterile disks were soaked with 4 ul LWWs containing T-phylloplanin or S-phylloplanin and placed on agar plates. The agar was inoculated with a sample of *Pyricularia grisea* or *Rhizctonia solani* (approximately 400 spores) and stored a dark moist environment at room temperature for 72 h ad 96 h respectively and then assayed for growth of *Pyricularia grisea* or *Rhizctonia solani*. The results, presented in FIG. 12, demonstrate that the disks soaked in the LWWs containing S-Phylloplanins or T-Phylloplanins inhibited growth of both *Pyricularia grisea* or *Rhizctonia solani*.

Treatment of LWWs with ProteinaseK to destroy LWW proteins prior to their application to leaves of potted plants (subsequently inoculated with live fungus culture), destroyed inhibition. Control treatments with a ProteinaseK preparation lacking LWWs had no inhibitory effect. These results demonstrate the well-characterized tobacco phylloplanin and the newly characterized sunflower phylloplanin (and to a lesser extent *Datura metel* phylloplanin) share common properties e.g.:

a) Inhibition of a basidiomycete, *R. solani*, an ascomycete, *P. grisea*, and an oomycete, *Peronospora tabacina*,
b) The proteinaceous nature of phylloplanins in tobacco, sunflower and *Datura* LWWs,
c) The high degree of glycosylation of tobacco and sunflower phylloplanins, and
d) That tobacco and sunflower (and *Datura*) possess short procumbent trichomes that are shown to produce tobacco phylloplanin.

Overall, our results indicate that tobacco, sunflower and *Datura* phylloplanins have broad specificity for different fungi and fungal-like pathogens in that they inhibit members of three of the four major classes of fungi and fungal-like organisms.

The examples set forth above are provided to give those of ordinary skill in the art with a complete disclosure and description of how to make and use the various embodiments of the invention, and are not intended to limit the scope of what the inventors regard as their invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

We claim:

1. A method for inhibiting proliferation of a microbe in or on a plant comprising overexpressing a phylloplanin in the plant wherein the phylloplanin comprises an amino acid sequence that is at least 95% identical to SEQ ID NO: 18, wherein the polypeptide is a disease- or pest-resistance conferring protein.

2. The method of claim 1, wherein the phylloplanin comprises an amino acid sequence selected from the group consisting of SEQ ID NO: 18, amino acids 22-150 of SEQ ID NO: 18, amino acids 23-150 of SEQ ID NO: 18, amino acids 24-150 of SEQ ID NO: 18.

3. The method of claim 1, wherein the microbe is an oomycetes, a basidiomycetes or a ascomycetes.

4. A method according to claim 1, wherein the plant is selected from the group consisting of a corn, a soybean, a tobacco, a potato, a tomato, a pepper, a *Datura*, an alfalfa, a cucumber, *vitis* sp, a *medicago* and a grass, optionally a turfgrass.

5. A method of inhibiting proliferation of a microbe in an organism in need thereof comprising administering a therapeutically effective amount of an isolated phylloplanin polypeptide to the organism wherein the phylloplanin comprises an amino acid sequence that is at least 95% identical to SEQ ID NO: 18, wherein the polypeptide is a disease or pest-resistance conferring protein, and wherein the microbe is an oomycetes, a basidiomycetes or an ascomycetes.

6. A method of inhibiting proliferation of a microbe in an organism in need thereof comprising administering a therapeutically effective amount of an isolated phylloplanin polypeptide to the organism wherein the phylloplanin comprises an amino acid sequence that is at least 95% identical to SEQ ID NO: 18, wherein the polypeptide is a disease or pest-resistance conferring protein, and wherein the phylloplanin polypeptide is expressed on the surface of a tobacco leaf, a sunflower leaf or a *Datura* leaf.

7. A method of inhibiting proliferation of a microbe in an organism in need thereof comprising administering a therapeutically effective amount of an isolated phylloplanin polypeptide to the organism wherein the phylloplanin comprises an amino acid sequence that is at least 95% identical to SEQ ID NO: 18, wherein the polypeptide is a disease or pest-resistance conferring protein, and wherein the phylloplanin polypeptide comprises an amino acid sequence selected from the group consisting of SEQ ID NO: 18, amino acids 22-150 of SEQ ID NO: 18, amino acids 23-150 of SEQ ID NO: 18, amino acids 24-150 of SEQ ID NO: 18.

8. The method of claim 5, wherein the organism is a plant or an animal.

9. The method according to claim 8, wherein the plant is selected from the group consisting of a corn, a soybean, a tobacco, a potato, a tomato, a pepper, a *Datura*, an alfalfa, a cucumber, *Vitis* sp, a *medicago* and a grass.

10. The method according to claim 9, wherein the grass is a turfgrass.

11. A method of inhibiting proliferation of a microbe in an organism in need thereof comprising administering a therapeutically effective amount of an isolated phylloplanin polypeptide to the organism wherein the phylloplanin comprises an amino acid sequence that is at least 95% identical to SEQ ID NO: 18, wherein the polypeptide is a disease or pest-resistance conferring protein, and wherein the phylloplanin polypeptide is administered to plant parts or plant tissue, growth medium surrounding the roots of the plants, or to seed of the plant before it is sown, using standard agricultural techniques.

12. A method of inhibiting proliferation of a microbe in an organism in need thereof comprising administering a therapeutically effective amount of an isolated phylloplanin polypeptide to the organism wherein the phylloplanin comprises an amino acid sequence that is at least 95% identical to SEQ ID NO: 18, wherein the polypeptide is a disease or pest-resistance conferring protein, and wherein the phylloplanin polypeptide is administered to plants or to plant growth medium in the form of a composition comprising the phylloplanin polypeptide in admixture with a solid or liquid diluent and optionally various adjuvants such as surface-active agents.

13. The method of claim 12, wherein the solid composition may be in the form of dispersible powders, granules, or grains.

14. A method for treating a fungal disease in a plant comprising treating a plant in need thereof with a composition comprising a phylloplanin, and wherein the plants are turfgrass or tobacco and wherein the phylloplanin comprises an amino acid sequence selected from the group consisting of SEQ ID NO: 18, amino acids 22-150 of SEQ ID NO: 18, amino acids 23-150 of SEQ ID NO: 18, amino acids 24-150 of SEQ ID NO: 18.

15. The method of claim 11, wherein the standard agricultural technique is spraying.

16. A method for inhibiting proliferation of a microbe in or on a plant comprising overexpressing a phylloplanin in the plant wherein the phylloplanin polypeptide comprises an amino acid sequence that is a conservative variant, wherein the conservative variant has an amino acid sequence selected from the group consisting of SEQ ID NO: 18, amino acids 22-150 of SEQ ID NO: 18, amino acids 23-150 of SEQ ID NO: 18, and amino acids 24-150 of SEQ ID NO: 18 having conservative amino acid substitutions in said sequences.

17. A method of inhibiting proliferation of a microbe in an organism in need thereof comprising administering a therapeutically effective amount of an isolated phylloplanin polypeptide to the organism wherein the phylloplanin polypeptide comprises an amino acid sequence that is a conservative variant, wherein the conservative variant has an amino acid sequence selected from the group consisting of SEQ ID NO: 18, amino acids 22-150 of SEQ ID NO: 18, amino acids 23-150 of SEQ ID NO: 18, amino acids 24-150 of SEQ ID NO: 18 having conservative amino acid substitutions in said sequences.

18. The method of claim 12 wherein the microbe is a *Peronospora tabacina*, a *Pyricularia grisea*, or a *Rhizctonia solani*.

19. The method of claim 1 wherein the microbe is a fungus.

20. A method of inhibiting proliferation of a microbe in an organism in need thereof comprising administering a therapeutically effective amount of an isolated phylloplanin polypeptide to the organism wherein the phylloplanin comprises an amino acid sequence that is at least 95% identical to SEQ ID NO: 18, wherein the polypeptide is a disease or pest-resistance conferring protein, and wherein the microbe is a fungus.

21. A method for inhibiting proliferation of a microbe on a surface comprising contacting a surface with an isolated phylloplanin wherein the phylloplanin comprises an amino acid sequence that is at least 95% identical to SEQ ID NO: 18, wherein the polypeptide is a disease- or pest-resistance conferring protein.

\* \* \* \* \*

SEQUENCE LISTING

```
<160> NUMBER OF SEQ ID NOS: 50

<210> SEQ ID NO 1
<211> LENGTH: 38
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(38)
<223> OTHER INFORMATION: n= inosine
<220> FEATURE:
<221> NAME/KEY: misc_feature
<222> LOCATION: (1)..(38)
<223> OTHER INFORMATION: w = a or t
<220> FEATURE:
<221> NAME/KEY: misc_feature
<222> LOCATION: (1)..(38)
<223> OTHER INFORMATION: y = c or t
<220> FEATURE:
<221> NAME/KEY: misc_feature
<222> LOCATION: (1)..(38)
<223> OTHER INFORMATION: r = a or g

<400> SEQUENCE: 1
acwttngtnt cnacwcatat ytcnggnctn gtyttttg                                 38

<210> SEQ ID NO 2
<211> LENGTH: 32
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(32)
<223> OTHER INFORMATION: n = inosine
<220> FEATURE:
<221> NAME/KEY: misc_feature
<222> LOCATION: (1)..(32)
<223> OTHER INFORMATION: r = a or g
<220> FEATURE:
<221> NAME/KEY: misc_feature
<222> LOCATION: (1)..(32)
<223> OTHER INFORMATION: y = c or t

<400> SEQUENCE: 2
aaraanccng tnggngcnar nccnacycta at                                       32

<210> SEQ ID NO 3
<211> LENGTH: 31
<212> TYPE: DNA
<213> ORGANISM: Artificial sequence
<220> FEATURE:
```

<223> OTHER INFORMATION: primer

<400> SEQUENCE: 3
ctcagtcccc aagttttcc taatgcatca g                                    31

<210> SEQ ID NO 4
<211> LENGTH: 29
<212> TYPE: DNA
<213> ORGANISM: Artificial sequence
<220> FEATURE:
<223> OTHER INFORMATION: primer

<400> SEQUENCE: 4
ggccaagaaa gttaactagc tgatgcata                                      29

<210> SEQ ID NO 5
<211> LENGTH: 28
<212> TYPE: DNA
<213> ORGANISM: Artificial sequence
<220> FEATURE:
<223> OTHER INFORMATION: primer

<400> SEQUENCE: 5
tggaacaagt atggcaaatg cagcgggg                                       28

<210> SEQ ID NO 6
<211> LENGTH: 32
<212> TYPE: DNA
<213> ORGANISM: Artificial sequence
<220> FEATURE:
<223> OTHER INFORMATION: primer

<400> SEQUENCE: 6
gggggttgcg attaatgcag ccaaaaggaa aa                                  32

<210> SEQ ID NO 7
<211> LENGTH: 30
<212> TYPE: DNA
<213> ORGANISM: Artificial sequence
<220> FEATURE:
<223> OTHER INFORMATION: primer

<400> SEQUENCE: 7
agcttctaga catatttcgg ggctggtttt                                     30

<210> SEQ ID NO 8
<211> LENGTH: 31
<212> TYPE: DNA
<213> ORGANISM: Artificial sequence
<220> FEATURE:
<223> OTHER INFORMATION: primer

<400> SEQUENCE: 8
agctctgcag ttagccggtg ggggcgaggc c                                   31

<210> SEQ ID NO 9
<211> LENGTH: 27
<212> TYPE: DNA
<213> ORGANISM: Artificial sequence
<220> FEATURE:
<223> OTHER INFORMATION: primer

<400> SEQUENCE: 9
agcttctaga atacttgttc caacact                                        27

<210> SEQ ID NO 10

```
<211> LENGTH: 26
<212> TYPE: DNA
<213> ORGANISM: Artificial sequence
<220> FEATURE:
<223> OTHER INFORMATION: primer

<400> SEQUENCE: 10
agctctgcag ttaattgatg ttaaga                                    26

<210> SEQ ID NO 11
<211> LENGTH: 23
<212> TYPE: DNA
<213> ORGANISM: Artificial sequence
<220> FEATURE:
<223> OTHER INFORMATION: primer

<400> SEQUENCE: 11
tgctcccacc actagaatca cca                                       23

<210> SEQ ID NO 12
<211> LENGTH: 27
<212> TYPE: DNA
<213> ORGANISM: Artificial sequence
<220> FEATURE:
<223> OTHER INFORMATION: primer

<400> SEQUENCE: 12
agcttctaga tgttggaaca agtatgg                                   27

<210> SEQ ID NO 13
<211> LENGTH: 34
<212> TYPE: DNA
<213> ORGANISM: Artificial sequence
<220> FEATURE:
<223> OTHER INFORMATION: primer

<400> SEQUENCE: 13
agcttctaga atgttacgtc ctgtagaaac ccca                           34

<210> SEQ ID NO 14
<211> LENGTH: 30
<212> TYPE: DNA
<213> ORGANISM: Artificial sequence
<220> FEATURE:
<223> OTHER INFORMATION: primer

<400> SEQUENCE: 14
agctctcgag tcattgtttg cctccctgct                                30

<210> SEQ ID NO 15
<211> LENGTH: 30
<212> TYPE: DNA
<213> ORGANISM: Artificial sequence
<220> FEATURE:
<223> OTHER INFORMATION: primer

<400> SEQUENCE: 15
agcttctaga atggtgagca agggcgagga                                30

<210> SEQ ID NO 16
<211> LENGTH: 30
<212> TYPE: DNA
<213> ORGANISM: Artificial sequence
<220> FEATURE:
<223> OTHER INFORMATION: primer

<400> SEQUENCE: 16
```

-continued

```
agctctcgag gctttacttg tacagctcgt                                          30
```

<210> SEQ ID NO 17
<211> LENGTH: 666
<212> TYPE: DNA
<213> ORGANISM: N. tabacum

<400> SEQUENCE: 17

```
aacacaattt cttacagcaa taactatcac atataacaat aactgccatg gcttcagcaa          60
aaattttctt gattttcctt ttggctgcat taatcgcaac ccccgctgca tttgccatac         120
ttgttccaac acttgtttca acacatataa gtgggcttgt attttgcagc gttaacggca         180
atttagatgt catcaacgga ctcagtcccc aagttttcc taatgcatca gtgcaattgc          240
ggtgtggagc aacaaatgtg atatcaagta caataacaaa tggatcggga gcattttcct         300
tggcggtgaa tactttccca ctgctaaact gcaatttagt ggttgcaact ccactatcaa         360
catgtaacgc gaccttacaa tcggttgggc gtttggcgtc atccttgaga cttgtaaata         420
tcactcttgg cagtggcacc ggtcttatta gagtcggttt agctcctact ggttttatac         480
ttaatcttaa catcaattaa tattgaacga gctagcctgc tggttcttaa ttagtactac         540
tactatgcat cagctagtta actttcttgg ccagctgctt actgcaagaa taaggactgt         600
tgtttccact agtgaataaa gtgcaaatca tatttgcaag tctaaaaaaa aaaaaaaaaa         660
aaaaaa                                                                   666
```

<210> SEQ ID NO 18
<211> LENGTH: 150
<212> TYPE: PRT
<213> ORGANISM: N. tabacum

<400> SEQUENCE: 18

```
Met Ala Ser Ala Lys Ile Phe Leu Ile Phe Leu Ala Ala Leu Ile
1               5                   10                  15

Ala Thr Pro Ala Ala Phe Ala Ile Leu Val Pro Thr Leu Val Ser Thr
            20                  25                  30

His Ile Ser Gly Leu Val Phe Cys Ser Val Asn Gly Asn Leu Asp Val
        35                  40                  45

Ile Asn Gly Leu Ser Pro Gln Val Phe Pro Asn Ala Ser Val Gln Leu
    50                  55                  60

Arg Cys Gly Ala Thr Asn Val Ile Ser Ser Thr Ile Thr Asn Gly Ser
65                  70                  75                  80

Gly Ala Phe Ser Leu Ala Val Asn Thr Phe Pro Leu Leu Asn Cys Asn
                85                  90                  95

Leu Val Val Ala Thr Pro Leu Ser Thr Cys Asn Ala Thr Leu Gln Ser
            100                 105                 110

Val Gly Arg Leu Ala Ser Ser Leu Arg Leu Val Asn Ile Thr Leu Gly
        115                 120                 125

Ser Gly Thr Gly Leu Ile Arg Val Gly Leu Ala Pro Thr Gly Phe Ile
    130                 135                 140

Leu Asn Leu Asn Ile Asn
145                 150
```

<210> SEQ ID NO 19
<211> LENGTH: 211
<212> TYPE: PRT
<213> ORGANISM: Arabidopsis thaliana

<400> SEQUENCE: 19

```
Met Gly Glu Asp Thr Leu Ser His Pro Lys Pro Lys Ala Thr Gln Thr
1               5                   10                  15

His Thr Pro Lys Lys Lys Lys Ala Phe Thr Phe Asn Ser Ser Met
            20              25                  30

Ala Met Leu Lys Asn Lys His Met Thr Val Ser Leu Ile Leu Val Cys
            35              40                  45

Leu Val Val Val Ser Pro Met Ala Glu Ala Gln Leu Gly Leu Gly Gly
        50              55                  60

Ser Gly Gly Leu Gly Gly Leu Ile Gly Gly Leu Val Gly Gly Leu Gly
65              70                  75                  80

Gly Leu Val Gly Gly Leu Val Gly Gly Ile Leu Asn Leu Val Asn Ile
                85                  90                  95

Asn Gly Val Val Phe Cys Ser Leu Asn Gly Ala Pro Ser Gly Thr Ser
            100                 105                 110

Thr Pro Ala Phe Ala Asn Ala Gly Val Glu Leu Gln Cys Gly Arg Gln
            115                 120                 125

Asn Arg Val Val Ser Thr Ala Thr Thr Asn Ala Ala Gly Leu Phe Ser
        130                 135                 140

Leu Pro Thr Asp Ser Ile Gln Met Leu Leu Ser Thr Leu Leu Ser Asp
145                 150                 155                 160

Cys Arg Val Val Val Thr Thr Pro Leu Ser Thr Cys Asn Ala Asn Leu
                165                 170                 175

Pro Ser Val Gly Asn Leu Val Ser Arg Leu Ala Met Ile Gly Asn Ser
                180                 185                 190

Leu Thr Gly Leu Leu Asn Ile Ile Ser Ile Ile Pro Ala Gly Phe Gly
                195                 200                 205

Leu Leu Asn
    210
```

<210> SEQ ID NO 20
<211> LENGTH: 145
<212> TYPE: PRT
<213> ORGANISM: Oryza sativa

<400> SEQUENCE: 20

```
Met Ala Ser Lys Ile Leu Leu Val Val Ile Gly Val Ala Val Val Ser
1               5                   10                  15

Val Val Ala Ser Ala Ala Pro Pro Ala Gln Pro Pro Arg Ile Gln Ala
            20              25                  30

Asp Val Val Val Met Gly Tyr Val Pro Cys Asn Asn Gly Thr Ser Met
            35              40                  45

Lys Ser Gly Ser Ala Pro Gly Phe Pro Asn Ala Val Val Gln Leu Gln
        50              55                  60

Cys Ala Gly Asp Ala Val Ala Ala Val Ala Ala Gly Ser Ala Thr Thr
65              70                  75                  80

Asp Gly Lys Gly Trp Phe Arg Met Ala Met Asn Thr Thr Ala Ala Leu
                85                  90                  95

Ser Ser Val Ala Ser Gly Cys Ser Leu Val Thr Thr Pro Leu Ala
            100                 105                 110

Thr Cys Asp Ala Ala Leu Pro Ala Thr Gly Thr Leu Gln Ser Gly Leu
            115                 120                 125

Arg Leu Leu Val Ser Met Val Phe Phe Pro Arg Gly Phe Ser Tyr Val
        130                 135                 140

Val
145
```

```
<210> SEQ ID NO 21
<211> LENGTH: 9
<212> TYPE: PRT
<213> ORGANISM: N. tabacum

<400> SEQUENCE: 21

Ile Leu Val Pro Thr Leu Val Ser Thr
1               5

<210> SEQ ID NO 22
<211> LENGTH: 19
<212> TYPE: PRT
<213> ORGANISM: N. tabacum

<400> SEQUENCE: 22

Ile Leu Val Pro Thr Leu Val Ser Thr His Ile Ser Gly Leu Val Phe
1               5                   10                  15

Cys Ser Val

<210> SEQ ID NO 23
<211> LENGTH: 19
<212> TYPE: PRT
<213> ORGANISM: N. tabacum

<400> SEQUENCE: 23

Ile Leu Val Pro Thr Leu Val Ser Thr His Ile Ser Gly Leu Val Phe
1               5                   10                  15

Cys Ser Val

<210> SEQ ID NO 24
<211> LENGTH: 19
<212> TYPE: PRT
<213> ORGANISM: N. tabacum

<400> SEQUENCE: 24

Ile Leu Val Pro Thr Leu Val Ser Thr His Ile Ser Gly Leu Val Phe
1               5                   10                  15

Cys Ser Val

<210> SEQ ID NO 25
<211> LENGTH: 6
<212> TYPE: PRT
<213> ORGANISM: N. tabacum

<400> SEQUENCE: 25

Ala Ser Val Gln Leu Arg
1               5

<210> SEQ ID NO 26
<211> LENGTH: 6
<212> TYPE: PRT
<213> ORGANISM: N. tabacum

<400> SEQUENCE: 26

Ile Leu Asn Leu Asn Ile
1               5

<210> SEQ ID NO 27
<211> LENGTH: 12
<212> TYPE: PRT
<213> ORGANISM: N. tabacum

<400> SEQUENCE: 27
```

```
Cys Gly Ala Thr Asn Val Ile Ser Ser Thr Ile Thr
1               5                  10
```

<210> SEQ ID NO 28
<211> LENGTH: 18
<212> TYPE: PRT
<213> ORGANISM: N. tabacum
<220> FEATURE:
<221> NAME/KEY: Xaa
<222> LOCATION: (11)..(11)
<223> OTHER INFORMATION: Xaa= any naturally occurring amino acid
<220> FEATURE:
<221> NAME/KEY: Xaa
<222> LOCATION: (15)..(15)
<223> OTHER INFORMATION: Xaa= any naturally occurring amino acid

<400> SEQUENCE: 28

```
Leu Val Val Ala Thr Pro Leu Ser Thr Cys Xaa Ala Thr Leu Xaa Ser
1               5                  10                  15
Val Gly
```

<210> SEQ ID NO 29
<211> LENGTH: 6
<212> TYPE: PRT
<213> ORGANISM: N. tabacum

<400> SEQUENCE: 29

```
Ile Leu Asn Leu Asn Ile
1               5
```

<210> SEQ ID NO 30
<211> LENGTH: 12
<212> TYPE: PRT
<213> ORGANISM: N. tabacum
<220> FEATURE:
<221> NAME/KEY: Xaa
<222> LOCATION: (5)..(5)
<223> OTHER INFORMATION: Xaa= any naturally occuring amino acid
<220> FEATURE:
<221> NAME/KEY: Xaa
<222> LOCATION: (7)..(7)
<223> OTHER INFORMATION: Xaa= any naturally occuring amino acid

<400> SEQUENCE: 30

```
Cys Gly Ala Thr Xaa Val Xaa Ser Ser Thr Ile Thr
1               5                  10
```

<210> SEQ ID NO 31
<211> LENGTH: 9
<212> TYPE: PRT
<213> ORGANISM: N. tabacum

<400> SEQUENCE: 31

```
Ile Arg Val Gly Leu Ala Pro Thr Gly
1               5
```

<210> SEQ ID NO 32
<211> LENGTH: 31
<212> TYPE: DNA
<213> ORGANISM: Artificial sequence
<220> FEATURE:
<223> OTHER INFORMATION: primer

<400> SEQUENCE: 32
atgggggaag acactttatc acatccaaaa c                                    31

<210> SEQ ID NO 33
<211> LENGTH: 27

```
<212> TYPE: DNA
<213> ORGANISM: Artificial sequence
<220> FEATURE:
<223> OTHER INFORMATION: primer

<400> SEQUENCE: 33
tcagttaaga agaccaaagc cggcagg                                          27

<210> SEQ ID NO 34
<211> LENGTH: 35
<212> TYPE: DNA
<213> ORGANISM: Artificial sequence
<220> FEATURE:
<223> OTHER INFORMATION: primer

<400> SEQUENCE: 34
gacgacgaca agatggggga agacacttta tcaca                                 35

<210> SEQ ID NO 35
<211> LENGTH: 35
<212> TYPE: DNA
<213> ORGANISM: Artificial sequence
<220> FEATURE:
<223> OTHER INFORMATION: primer

<400> SEQUENCE: 35
gaggagaagc ccggtcagtt aagaagacca aagcc                                 35

<210> SEQ ID NO 36
<211> LENGTH: 145
<212> TYPE: PRT
<213> ORGANISM: S. rebaudiana

<400> SEQUENCE: 36
```

Gln Ile Leu Pro Pro Ile Leu Pro Pro Thr Ile Ile Arg Pro Pro
1               5                   10                  15

Pro Ile Leu Pro Pro Ile Val Leu Pro Pro Ile Val Leu Asn Pro
            20                  25                  30

Val Leu Asn Val Thr Gly Ile Val Ser Cys Ser Val Asn Ala Thr Val
        35                  40                  45

Asn Thr Thr Thr Ala Pro Pro Phe Pro Asn Ala Gln Val Gln Leu Arg
    50                  55                  60

Cys Gly Gly Leu Val Val Gly Ala Ala Thr Thr Asn Gln Ser Gly Ala
65                  70                  75                  80

Phe Asn Ile Val Val Asn Pro Phe Leu Ser Thr Val Ala Asn Leu Leu
                85                  90                  95

Ser Cys Arg Val Val Val Thr Thr Pro Leu Ala Thr Cys Asn Val Ile
            100                 105                 110

Leu Pro Ser Thr Gly Thr Leu Gln Ala Pro Leu Gln Ile Val Gly Asn
        115                 120                 125

Ile Leu Asn Ile Leu Phe Ala Ile Pro Gly Gln Phe Leu Tyr Leu Gln
    130                 135                 140

Val
145

```
<210> SEQ ID NO 37
<211> LENGTH: 142
<212> TYPE: PRT
<213> ORGANISM: B. rapa

<400> SEQUENCE: 37
```

Gln Leu Gly Gly Leu Gly Gly Gly Leu Gly Gly Leu Gly Met Leu Leu

```
                1               5                  10                 15
Gly Gly Leu Thr Asn Ile Phe Asn Ile Gln Gly Leu Leu Met Cys Ser
                20                 25                 30

Val Thr Gly Thr Val Ser Thr Asn Asn Ala Thr Ala Val Pro Pro Phe
                35                 40                 45

Pro Asn Ala Gly Ile Val Phe Gln Cys Thr Gly Gln Asn Val Ser Ser
    50                 55                 60

Thr Thr Thr Asn Ala Asn Gly Val Phe Ser Ile Pro Thr Ile Gly Leu
65                  70                 75                     80

Pro Phe Ser Pro Ser Thr Leu Leu Ser Ser Gly Cys Arg Leu Val Val
                85                 90                 95

Thr Thr Pro Leu Thr Ala Cys Asn Val Ser Leu Pro Ala Ala Gly Leu
                100                105                110

Leu Met Ala Pro Leu Ser Leu Val Gly Thr Ala Ala Gly Asp Gly Leu
                115                120                125

Asn Ile Phe Ser Leu Val Pro Ser Ala Phe Gly Leu Val Gly
                130                135                140
```

<210> SEQ ID NO 38
<211> LENGTH: 132
<212> TYPE: PRT
<213> ORGANISM: H. annuus

<400> SEQUENCE: 38

```
Val Leu Ile Ala Ala Gln Ala Asp Glu Ala Gln Gly Leu Pro Pro Ile
1               5                   10                  15

Thr Ala Ala Val Asn Ile Ser Gly Ile Val Thr Cys Ser Val Asn Gly
                20                  25                  30

Ser Ala Asn Ala Pro Pro Phe Ala Asn Ala Leu Val Glu Leu Ser Cys
                35                  40                  45

Gly Gly Asn Val Ile Ala Ser Ala Val Thr Asn Ala Gln Gly Val Phe
                50                  55                  60

Asn Ile Thr Val Asn Pro Leu Arg Val Thr Leu Asn Asn Leu Leu Ser
65                  70                  75                  80

Ser Cys Arg Ile Ile Val Ala Thr Pro Leu Ser Asn Cys Asn Ala Thr
                85                  90                  95

Leu Pro Thr Ala Gly Thr Leu Gln Ser Ala Leu Gln Val Ala Gly Thr
                100                 105                 110

Phe Ile Arg Gly Ile Leu Asn Asn Val Asn Leu Val Pro Ile Arg Phe
                115                 120                 125

Arg Leu Val Val
    130
```

<210> SEQ ID NO 39
<211> LENGTH: 153
<212> TYPE: PRT
<213> ORGANISM: A. thaliana

<400> SEQUENCE: 39

```
Gln Leu Gly Leu Gly Gly Ser Gly Gly Leu Gly Leu Ile Gly Gly
1               5                   10                  15

Leu Val Gly Gly Leu Gly Gly Leu Val Gly Gly Leu Gly Gly Ile
                20                  25                  30

Leu Asn Leu Val Asn Ile Asn Gly Val Val Phe Cys Ser Leu Asn Gly
                35                  40                  45

Ala Pro Ser Gly Thr Ser Thr Pro Ala Phe Ala Asn Ala Gly Val Glu
    50                  55                  60
```

Leu Gln Cys Gly Arg Gln Asn Arg Val Val Ser Thr Ala Thr Thr Asn
65                  70                  75                  80

Ala Ala Gly Leu Phe Ser Leu Pro Thr Asp Ser Ile Gln Met Leu Leu
                85                  90                  95

Ser Thr Leu Leu Ser Asp Cys Arg Val Val Thr Thr Pro Leu Ser
            100                 105                 110

Thr Cys Asn Ala Asn Leu Pro Ser Val Gly Asn Leu Val Ser Arg Leu
            115                 120                 125

Ala Met Ile Gly Asn Ser Leu Thr Gly Leu Leu Asn Ile Ile Ser Ile
        130                 135                 140

Ile Pro Ala Gly Phe Gly Leu Leu Asn
145                 150

<210> SEQ ID NO 40
<211> LENGTH: 128
<212> TYPE: PRT
<213> ORGANISM: A. thaliana

<400> SEQUENCE: 40

Gln Ser Gly Leu Gly Gly Ile Asn Val Pro Ile Ile Asn Gly Val Leu
1               5                   10                  15

Phe Cys Thr Ile Asn Gly Ala Pro Leu Asn Gly Thr Pro Ala Pro Ala
            20                  25                  30

Phe Ala Asn Ala Val Val Gln Leu Gln Cys Gly Asn Leu Asn Arg Val
        35                  40                  45

Val Ala Glu Thr Ile Ile Asn Ile Ala Gly Leu Phe Thr Phe Ser Thr
    50                  55                  60

Asn Gly Ile Gln Ile Ser Leu Pro Thr Leu Leu Asn Asp Cys Arg Ile
65                  70                  75                  80

Val Val Pro Thr Pro Arg Ser Ser Cys Asp Ala Thr Leu Pro Ser Thr
                85                  90                  95

Gly Gln Leu Ile Ser Gln Leu Asn Leu Val Gly Ser Ile Val Ser Gly
            100                 105                 110

Leu Leu Asn Ile Val Ala Ile Leu Pro Thr Gly Phe Ile Pro Thr Ile
            115                 120                 125

<210> SEQ ID NO 41
<211> LENGTH: 124
<212> TYPE: PRT
<213> ORGANISM: O. sativa

<400> SEQUENCE: 41

Ala Pro Pro Ala Gln Pro Pro Arg Ile Gln Ala Asp Val Val Val Met
1               5                   10                  15

Gly Tyr Val Pro Cys Asn Asn Gly Thr Ser Met Lys Ser Gly Ser Ala
            20                  25                  30

Pro Gly Phe Pro Asn Ala Val Val Gln Leu Gln Cys Ala Gly Asp Ala
        35                  40                  45

Val Ala Ala Val Ala Ala Gly Ser Ala Thr Thr Asp Gly Lys Gly Trp
    50                  55                  60

Phe Arg Met Ala Met Asn Thr Thr Ala Ala Leu Ser Ser Val Ala Ser
65                  70                  75                  80

Gly Cys Ser Leu Val Val Thr Thr Pro Leu Ala Thr Cys Asp Ala Ala
                85                  90                  95

Leu Pro Ala Thr Gly Thr Leu Ser Gly Leu Arg Leu Leu Val Ser
            100                 105                 110

-continued

Met Val Phe Phe Pro Arg Gly Phe Ser Tyr Val Val
            115                 120

<210> SEQ ID NO 42
<211> LENGTH: 118
<212> TYPE: PRT
<213> ORGANISM: O. sativa

<400> SEQUENCE: 42

Lys Leu Gly Arg Leu Val Val Thr Gly Val Val Pro Cys Asn Thr Gly
1               5                   10                  15

Ser Leu Ile Asp Ile Ala Thr Ser Pro Ala Phe Pro Asn Ala Asp Val
            20                  25                  30

Glu Leu Arg Cys Ala Gly Lys Leu Val Ala Gly Ala Thr Thr Asn Ser
        35                  40                  45

Asn Gly Ser Phe Ala Met Glu Ala Asp Leu Thr Ser Gly Leu Ala Met
    50                  55                  60

Leu Ile Gly Gly Cys Lys Leu Val Val Asp Thr Pro Leu Ile Lys Cys
65                  70                  75                  80

Asp Ala Asn Leu Pro Ala Ala Gly Ser Leu Val Ser Tyr Leu Gln Gly
                85                  90                  95

Pro Leu Thr Arg Leu Leu Gly Gly Ile Phe Arg Leu Phe Pro Ala Gly
            100                 105                 110

Phe Ser Phe His Ala His
            115

<210> SEQ ID NO 43
<211> LENGTH: 132
<212> TYPE: PRT
<213> ORGANISM: S. tuberosum

<400> SEQUENCE: 43

Gln Leu Gly Gly Leu Leu Gly Gly Leu Leu Gly Pro Ile Ser Ile Asp
1               5                   10                  15

Gly Val Leu Phe Cys Ser Leu Asn Gly Lys Ile Asp Val Leu Asn Gly
            20                  25                  30

Ala Thr Thr Pro Ile Phe Pro Asn Ala Ser Val Gln Leu Arg Cys Gly
        35                  40                  45

Ala Gly Asn Val Val Ser Ser Thr Thr Thr Asn Gly Ser Gly Ala Phe
    50                  55                  60

Ser Leu Val Leu Asn Pro Val Gln Asn Ile Leu Ser Ser Leu Leu Ser
65                  70                  75                  80

Asn Cys Asn Ile Val Val Thr Thr Pro Leu Ser Thr Cys Asn Ala Ser
                85                  90                  95

Leu Pro Ser Val Gly Val Leu Gln Ala Pro Leu Gln Ile Val Gly Arg
            100                 105                 110

Thr Thr Gly Gly Leu Val Asn Leu Val Ile Gly Val Phe Gln Leu Ile
            115                 120                 125

Pro Leu Leu Asn
    130

<210> SEQ ID NO 44
<211> LENGTH: 133
<212> TYPE: PRT
<213> ORGANISM: L. esculentum

<400> SEQUENCE: 44

Gln Leu Gly Gly Leu Leu Gly Gly Leu Leu Ala Pro Thr Ser Ile Glu
1               5                   10                  15

Gly Val Leu Phe Cys Ser Leu Asn Gly Lys Ile Asp Val Leu Asn Gly
            20                  25                  30

Ala Thr Thr Pro Ile Phe Pro Asp Ala Ser Val Gln Leu Arg Cys Gly
        35                  40                  45

Ala Gly Asn Val Val Ser Ser Thr Thr Thr Asn Gly Ser Gly Ala Phe
    50                  55                  60

Ser Leu Val Thr Ser Pro Val Gln Ser Leu Ser Ser Leu Leu Ser
65                  70                  75                  80

Asp Cys Asn Ile Val Val Ile Thr Pro Leu Ser Thr Cys Asn Ala Thr
                85                  90                  95

Leu Pro Ser Val Gly Val Leu Gln Ala Pro Leu Gln Ile Val Gly Lys
                100                 105                 110

Thr Ala Gly Gly Gly Leu Leu Asn Ile Val Lys Leu Val Thr Gly Ala
            115                 120                 125

Phe Gln Leu Ile Asn
    130

<210> SEQ ID NO 45
<211> LENGTH: 115
<212> TYPE: PRT
<213> ORGANISM: A. majus

<400> SEQUENCE: 45

Cys Thr Pro Asn Gly Asn Ile Gly Val Asn Gly Thr Ser Thr Pro Val
1               5                   10                  15

Phe Pro Asn Ala Ala Val Gln Leu Gln Cys Gly Gly Thr Val Val Ser
            20                  25                  30

Thr Thr Thr Thr Asn Gly Leu Gly Gln Phe Ser Met Leu Leu Asp Pro
        35                  40                  45

Leu Asn Phe Val Leu Ser Thr Leu Val Ser Gly Cys Arg Leu Ala Val
    50                  55                  60

Thr Thr Pro Leu Ala Thr Cys Asn Ala Ser Leu Pro Ser Ala Gly Gly
65                  70                  75                  80

Leu Ile Ser Thr Leu Gln Phe Val Gly Ser Thr Val Leu Gly Leu Leu
                85                  90                  95

Asn Val Gly Asn Ile Ile Pro Ser Gly Phe Asn Phe Ser Ala Asn Met
                100                 105                 110

Asn Leu Asn
    115

<210> SEQ ID NO 46
<211> LENGTH: 138
<212> TYPE: PRT
<213> ORGANISM: P. tremuloides

<400> SEQUENCE: 46

Ala Pro Val Ala Glu Ala Gln Leu Gly Leu Ile Gly Gly Leu Leu Gly
1               5                   10                  15

Leu Ile Arg Ile Gln Gly Thr Leu Phe Cys Thr Ala Asp Gly Asn Ile
            20                  25                  30

Gly Ala Asn Gly Thr Ala Thr Pro Val Phe Pro Asn Ala Leu Val Gln
        35                  40                  45

Leu Gln Cys Gly Gly Asn Val Val Ser Thr Ser Thr Thr Asn Gly Ser
    50                  55                  60

Gly Met Phe Ser Ile Leu Leu Asp Pro Leu Ser Tyr Ile Leu Ser Ser
65                  70                  75                  80

```
Ile Leu Ser Asp Cys Asn Leu Lys Val Asp Thr Pro Leu Ile Ser Cys
                85                  90                  95

Asn Ser Ser Leu Pro Ala Val Gly Gly Leu Leu Ser Pro Leu Arg Phe
            100                 105                 110

Ile Gly Asn Thr Ala Leu Gly Ala Val Leu Ser Val Ala Asn Ile Ile
        115                 120                 125

Pro Ala Gly Phe Arg Phe Val Pro Ser Asn
    130                 135

<210> SEQ ID NO 47
<211> LENGTH: 132
<212> TYPE: PRT
<213> ORGANISM: Soybean clone

<400> SEQUENCE: 47

Gln Leu Gly Ile Leu Ser Gly Leu Leu Gly Ser Val Ser Asn Ile Gln
1               5                   10                  15

Gly Thr Val Phe Cys Thr Ser Lys Asp Asn Met Gly Val Lys Gly Ala
            20                  25                  30

Ser Val Pro Val Phe Pro Asn Ala Gln Val Gln Leu Val Cys Gly Gly
        35                  40                  45

Lys Glu Leu Ser Asn Ala Lys Thr Asn Asp Asp Gly Thr Phe Ser Met
 50                 55                  60

Met Met Asp Pro Leu Leu Leu Asp Leu Ala Ser Leu Leu Ser Gly Cys
65                  70                  75                  80

Asn Leu Val Val Ala Thr Pro Leu Ser Asn Cys Asn Ala Lys Leu Pro
                85                  90                  95

Ser Thr Gly Gly Leu Ile Ser Thr Leu Asn Phe Ala Gly Ile Thr Ser
            100                 105                 110

Val Gly Thr Gln Thr Met Ala Asn Ile Ile Pro Ser Gly Phe His Phe
        115                 120                 125

Leu Pro Ser Ile
    130

<210> SEQ ID NO 48
<211> LENGTH: 118
<212> TYPE: PRT
<213> ORGANISM: H. vulgare

<400> SEQUENCE: 48

Lys Leu Gly Arg Leu Val Val Ser Gly Val Ala Pro Cys Asn Thr Gly
1               5                   10                  15

Ser Leu Ile Asp Ile Ala Thr Ser Pro Ala Phe Pro Asn Ala Glu Val
            20                  25                  30

Glu Leu Arg Cys Ala Gly Gln Val Val Ala Gly Ala Thr Thr Asn Thr
        35                  40                  45

Asn Gly Ser Phe Thr Met Glu Ala Asp Leu Thr Ser Ala Leu Ala Ala
 50                 55                  60

Phe Ile Gly Arg Cys Ser Leu Val Val Asp Thr Pro Leu Ile Lys Cys
65                  70                  75                  80

Asp Ala Gln Leu Pro Pro Ala Gly Arg Leu Val Ser Tyr Leu Gln Gly
                85                  90                  95

Pro Leu Thr Arg Leu Leu Gly Gly Ile Phe His Leu Phe Pro Ala Gly
            100                 105                 110

Phe Ser Phe His Ser Arg
    115
```

```
<210> SEQ ID NO 49
<211> LENGTH: 1249
<212> TYPE: DNA
<213> ORGANISM: Unknown
<220> FEATURE:
<223> OTHER INFORMATION: promoter sequence

<400> SEQUENCE: 49
cccattccac tatgaacttc ccggaattca attctgacta tgcgtacaag tcataatgaa      60
gctgcacata gccttcatat cgctaaacga cgtgctaggt ctcaaaacga cctgtcgggg     120
tcgttacatt agaggtgatt aacttcgtgt atacttgtgc aagtgttcta taacaatttc     180
aggccaacct agtaagagta gaaatagtga atggcacata acaaacgatc accacgaaat     240
gtacatgata taactcacac aaggtaggca cgctactaga caattaccaa taacaacaat     300
gcctaggaca tcacaagata tgaaaaatca atccttacta tcacggttga gttgtaacgt     360
gtaagaatat ttcacacttt ttagggcact aagatcactc caccaacatt tcaagagaat     420
cactggcact gccaaaaagc cctctacact gtagtgaatt tttgttagtt atctaaagtt     480
aattattcac ttagtattct ttacattagg ttccccccct ctaggtcctg cacgtaacta     540
gattgaatgg attggtccac tctattatta cagagtaatt attaaatttt tatttgacta     600
ggcaacacta attgcactat caacaaagta ttagttctag ccttctgggt acttcatacc     660
tatgcaaatg ataattttat ttaaaacaat agatgtacat ggatataaat acctatgaaa     720
attaaataaa atataactaa gaaaaaaaat ttaaagttca ctcctaagat atcgggttat     780
tacatgacca aacacaattt gtttatcaaa tactttcaaa agaatttgtc aaacgtaaat     840 tattttctc caaagtgact tatgaattac tatgttgata aaatactttt caaagtaact     900
aatgtttaga agtcaaggat gggcttcttt tgattattga agtttgtagc aattgtatgt     960
agttatagtc agggtgacca ccagcatctc atatagcaat acacaagtgg gttagcgtat    1020
ttgaaatttc aattagttca ttcaaatata cacgtaatag cattataagc cactttcaca    1080
acagatagat tagggttttt aaaatttcaa ccaatgatat ttactataaa ttgatcatgc    1140 acaaaccta attgagcaac acaatttctt acagcaataa ctatcacata taacaataac    1200
tgccatggct tcagcaaaaa ttttcttgat tttccttttg gctgcatta                1249

<210> SEQ ID NO 50
<211> LENGTH: 15
<212> TYPE: PRT
<213> ORGANISM: Unknown
<220> FEATURE:
<223> OTHER INFORMATION: promoter sequence

<400> SEQUENCE: 50

Met Ala Ser Ala Lys Ile Phe Leu Ile Phe Leu Leu Ala Ala Leu
 1               5                  10                  15
```